United States Patent
Bravi et al.

(10) Patent No.: US 11,254,671 B2
(45) Date of Patent: Feb. 22, 2022

(54) CHEMICAL COMPOUNDS

(71) Applicant: GLAXOSMITHKLINE INTELLECTUAL PROPERTY DEVELOPMENT LIMITED, Middlesex (GB)

(72) Inventors: Gianpaolo Bravi, Stevenage (GB); Heather Hobbs, Stevenage (GB); Graham George Adam Inglis, Stevenage (GB); Simon Nicolle, Stevenage (GB); Simon Peace, Stevenage (GB)

(73) Assignee: GLAXOSMITHKLINE INTELLECTUAL PROPERTY DEVELOPMENT LIMITED, Brentford (GB)

( * ) Notice: Subject to any disclaimer, the term of this patent is extended or adjusted under 35 U.S.C. 154(b) by 67 days.

(21) Appl. No.: 16/770,673

(22) PCT Filed: Dec. 12, 2018

(86) PCT No.: PCT/EP2018/084618
§ 371 (c)(1),
(2) Date: Jun. 8, 2020

(87) PCT Pub. No.: WO2019/115640
PCT Pub. Date: Jun. 20, 2019

(65) Prior Publication Data
US 2021/0163472 A1 Jun. 3, 2021

(30) Foreign Application Priority Data
Dec. 15, 2017 (GB) ..................... 1720989

(51) Int. Cl.
*C07D 471/04* (2006.01)
*C07D 519/00* (2006.01)
*A61P 11/00* (2006.01)

(52) U.S. Cl.
CPC ............ *C07D 471/04* (2013.01); *A61P 11/00* (2018.01); *C07D 519/00* (2013.01)

(58) Field of Classification Search
CPC ...... C07D 471/04; C07D 519/00; A61P 11/00
USPC ....................................... 514/230.5
See application file for complete search history.

(56) References Cited

FOREIGN PATENT DOCUMENTS

| WO | 2009/007751 | * | 1/2009 |
| WO | 2009/007751 A2 | | 1/2009 |

* cited by examiner

*Primary Examiner* — Niloofar Rahmani
(74) *Attorney, Agent, or Firm* — Robert J. Smith

(57) ABSTRACT

The invention relates to compounds of formula (I):

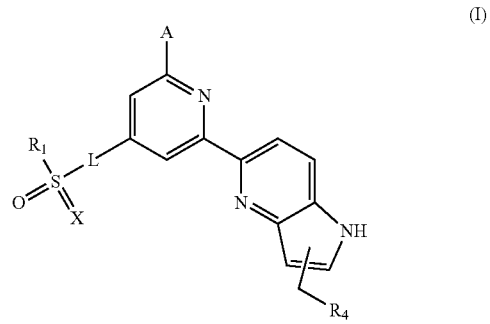

wherein $R_1$, $R_2$, $R_3$, $R_4$, L and A are as defined in the description and claims, or pharmaceutically acceptable salts thereof having mTOR kinase inhibitor activity. The invention also relates to pharmaceutical compositions including a compound of formula (I) or a pharmaceutically acceptable salt thereof, and to the use of a compound of formula (I) or a pharmaceutically acceptable salt thereof in therapy, including in the treatment of a disease or condition for which an mTOR kinase inhibitor activity is indicated, and in particular the treatment of idiopathic pulmonary fibrosis.

15 Claims, 1 Drawing Sheet

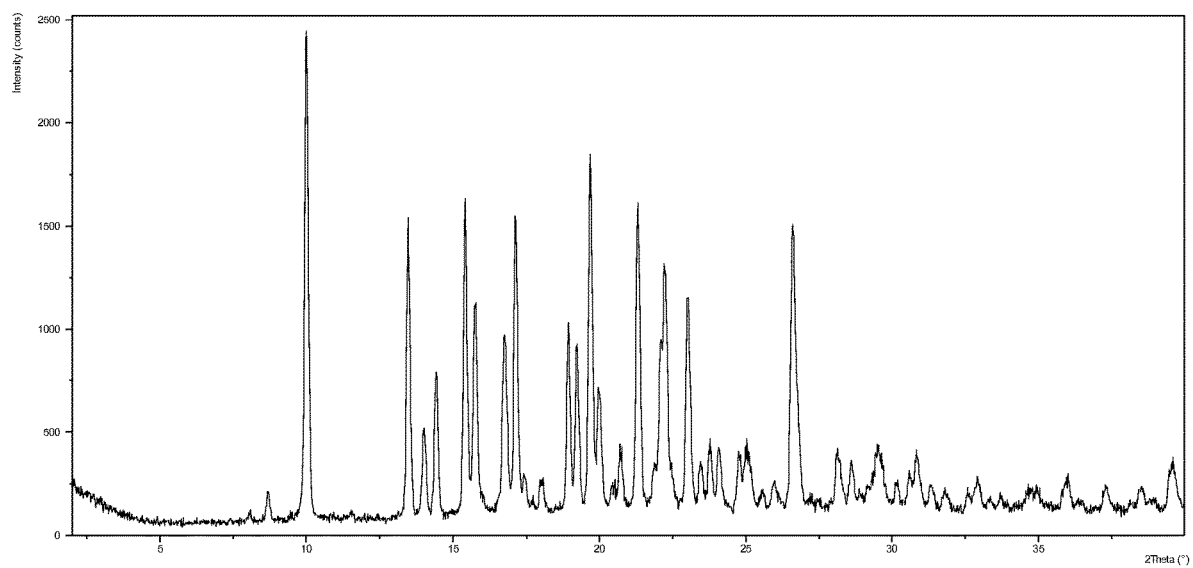

CHEMICAL COMPOUNDS

CROSS-REFERENCE TO RELATED APPLICATIONS

This application is filed pursuant to 35 U.S.C. § 371 as a United States National Phase Application of International Application No. PCT/EP2018/084618 filed Dec. 12, 2018 which claims priority from GB Application No. 1720989.1 filed Dec. 15, 2017.

FIELD OF THE INVENTION

The invention relates to mTOR kinase inhibitors, to pharmaceutical compositions containing them, and the use in therapy of such compounds and compositions.

BACKGROUND TO THE INVENTION

The mammalian target of rapamycin (mTOR) is an evolutionarily conserved serine/threonine kinase and functionally regulates a diverse range of cellular activities. The target of rapamycin (TOR), mammalian TOR (mTOR), also known as the FKBP-12-rapamycin associated protein (FRAP) or rapamycin and FKBP target (RAFT)1 and rapamycin target (RAPT) controls diverse cellular processes ranging from protein translation in response to amino acids or growth factors, autophagy, metabolism, inflammation, lipid synthesis and cytoskeletal rearrangements. Within the cell, mTOR exists as two distinct protein complexes known as mTORC1 (mTOR, RAPTOR, mLST8, PRAS40 and DEPTOR) and mTORC2 (mTOR, RICTOR, mLST8, mSIN1 and PROTOR) each complex consisting of the protein kinase domain, mTOR and complex specific accessory proteins. Both complexes share two common components; mLST8 and Deptor but other components are distinct. mTORC1 uniquely consists of PRAS40 and Raptor whilst mTORC2 requires Rictor, Protor and Sin1. mLST8, Raptor, Rictor and Sin1 are critical for complex assembly and/or link mTOR kinase to its substrate Upstream and downstream effectors of mTORC1 have been characterised much more extensively than for mTORC2. mTORC1 is activated by insulin, amino acids and repressed by AMP-activated protein kinase (AMPK). mTORC1 can promote mRNA translation and protein synthesis via two substrates; ribosomal protein S6 kinases (S6Ks) and eukaryotic translation initiation factor 4E-binding protein (4E-BP)1. In addition, mTORC1 represses autophagy, regulates glucose metabolism and mitochondrial function. mTORC1 has been confirmed as a central regulator of longevity as the allosteric mTORC1 inhibitor, rapamycin has been shown to extend lifespan in yeast, nematodes, fruit flies and mice (reviewed in Johnson et al., 2013).

The downstream substrates and signalling pathways for mTORC2 have not been fully elucidated. mTORC2 inhibits FOXO3A via S6K1 and AKT leading to increased longevity and regulates actin cytoskeleton assembly. Rictor and Sin1 are the two unique, essential mTORC2 components and Sin1 phosphorylation disassociates Sin1 from the complex suppressing mTORC2 kinase activity (Liu et al., 2013).

mTOR has been implicated in age-related pathologies and is considered a master regulator of cell growth and metabolism in response to nutrient cues. Rapamycin (Sirolimus) inhibits mTORC1 by binding to an abundant, intracellular protein, FKBP12 (FK506-binding protein) and disrupting the interaction between mTOR and raptor to decrease activity. Rapamycin does not directly inhibit mTORC2 but chronic exposure under some circumstances can lead to mTOR sequestration from mTORC2, inhibiting mTORC2 complex assembly. In addition to rapamycin, two mTOR compounds with the same mechanism of action are approved for clinical use, everolimus and temsirolimus for renal cell carcinoma and organ transplant rejection. Small molecule, dual inhibitors of mTORC1 and mTORC2 are in clinical development for a diverse range of oncology indications.

Idiopathic Pulmonary Fibrosis (IPF) is characterized by extracellular matrix (ECM) accumulation leading to structural distortion of lung architecture resulting in impaired gaseous exchange and death due to respiratory failure. Emerging evidence suggests cellular metabolic reprogramming may contribute to the pathogenesis of IPF including the observation of reproducibly increased $^{18}$fluorodeoxyglucose (FDG) pulmonary uptake in honeycombed lesion (Groves et al., 2009) elevated lung lactic acid levels promoting activation of the central profibrotic mediator, transforming growth factor (TGF)-β (Kottmann et al., 2012) and metabolic changes associated with fibroblast-to-myofibroblast transdifferentiation (Bernard et al., 2015). Energetic adaption maybe modulated by mTOR. In addition, inhibition of class I PI3k and mTOR has been shown to arrest fibroblast proliferation and collagen deposition in cells and tissue derived from patients with IPF (Mercer et al., 2015). mTOR is a critical effector of TGF-β in fibroblasts (Rahimi et al., 2009) and TGF-β has been implicated in diversefibrotic conditions affecting the lung, kidney, skin and liver (for a review see Nanthakumar et al., 2015). More recently, TGF-β was shown to promote cardiac fibrosis (Khalil et al., 2017). Myofibroblasts are considered the primary pathogenic cell type during the development of a fibroproliferative response and subsequent organ fibrosis. Comparative studies using control and fibrotic myofibroblasts revealed aberrant translational regulation with dysregulated mTOR activity in disease-derived cells (Larsson et al., 2009).

Currently, two drugs are approved for the treatment of IPF, Esbriet (pirfenidone) and Ofev (nintedanib) but not all patients qualify for these treatments depending on the severity of decline in lung function. Both drugs are associated with significant side effects and tolerability issues. The mechanism of action for Esbriet remains unknown and patients are titrated with increasing doses but many patients fail to tolerate the recommended clinical dose. Clinical data to date suggests both drugs slow disease progression.

SUMMARY OF THE INVENTION

In one aspect, the invention relates to a compound according to formula (I),

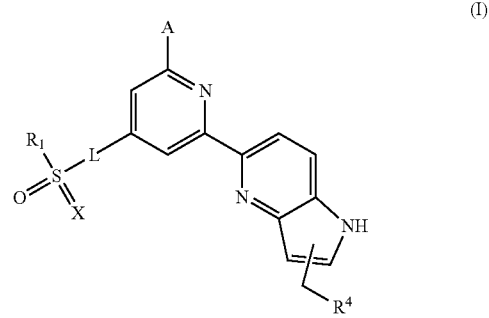

wherein:

A is

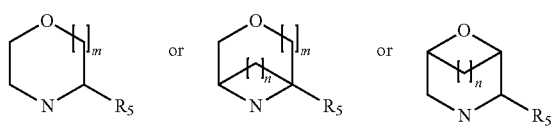

where ring A is attached via the N atom;

X is O or NH;

L is $(C_1-C_3)$alkylene, $(C_1-C_3)$haloalkylene, $(C_3-C_5)$cycloalkylene or $(C_2-C_5)$heterocycloalkylene;

$R_1$ is $(C_1-C_3)$alkyl, $(C_3-C_5)$cycloalkyl, $(C_1-C_3)$alkoxy, or $NR_2R_3$, which $(C_1-C_3)$alkyl, $(C_3-C_5)$cycloalkyl or $(C_1-C_3)$alkoxy is optionally substituted with $NR_2R_3$;

$R_2$ and $R_3$ are each independently $CH_3$ or H;

$R_4$ is $NH(C_1-C_3)$alkyl, $N((C_1-C_3)$alkyl$)_2$, $(C_1-C_3)$alkyl, $NH_2$ or OH;

$R_5$ is $(C_1-C_3)$alkyl or H;

m is 1 or 2; and n is 1, 2 or 3;

or a pharmaceutically acceptable salt thereof.

In another aspect, the invention relates to a pharmaceutical composition comprising a compound according to formula (I) or pharmaceutically acceptable salt thereof, and a pharmaceutically acceptable carrier, diluent or excipient.

In a further aspect, the invention relates to a method of treating a disease in which an mTOR kinase inhibitor is indicated, in a subject in need thereof, in particular a human subject in need thereof, comprising administering to said subject a therapeutically amount of a compound according to formula (I), or pharmaceutically acceptable salt thereof.

In a further aspect, the invention relates to a compound according to formula (I), or pharmaceutically acceptable salt thereof, for use in therapy.

In a further aspect, the invention relates to a compound according to formula (I), or pharmaceutically acceptable salt thereof, for use in the treatment of a disease in which an mTOR kinase inhibitor is indicated.

In a further aspect, the invention relates to a compound according to formula (I), or pharmaceutically acceptable salt thereof, for use in the manufacture of a medicament for the treatment of a disease in which an mTOR kinase inhibitor is indicated.

In a further aspect, the invention relates to a pharmaceutical composition comprising a compound according to formula (I), or pharmaceutically acceptable salt thereof, and an additional therapeutic agent.

FIGURES

FIG. 1 XRPD of (S)-1-(5-(6-(3-ethylmorpholino)-4-(4-(methylsulfonyl)tetrahydro-2H-pyran-4-yl)pyridin-2-yl)-1H-pyrrolo[3,2-b]pyridin-2-yl)-N-methylmethanamine

DETAILED DESCRIPTION OF THE INVENTION

In one aspect, the invention relates to a compound according to formula (I),

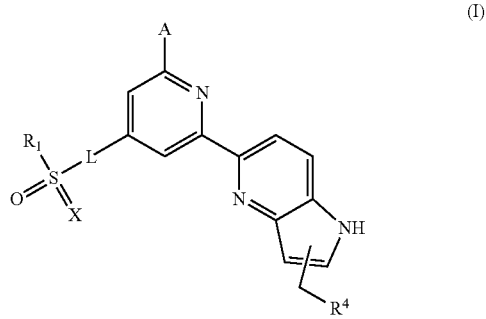

wherein:

A is

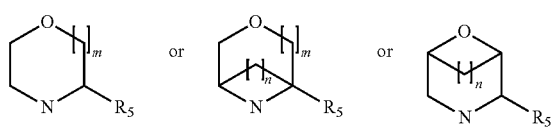

where ring A is attached via N;

X is O or NH;

L is $(C_1-C_3)$alkylene, $(C_1-C_3)$haloalkylene, $(C_3-C_5)$cycloalkylene or $(C_2-C_5)$heterocycloalkylene;

$R_1$ is $(C_1-C_3)$alkyl, $(C_3-C_5)$ cycloalkyl, $(C_1-C_3)$alkoxy, or $NR_2R_3$, which $(C_1-C_3)$alkyl, $(C_3-C_5)$cycloalkyl or $(C_1-C_3)$alkoxy is optionally substituted with $NR_2R_3$;

$R_2$ and $R_3$ are each independently $CH_3$ or H;

$R_4$ is $NH(C_1-C_3)$alkyl, $N((C_1-C_3)$alkyl$)_2$, $(C_1-C_3)$alkyl, $NH_2$ or OH;

$R_5$ $(C_1-C_3)$alkyl or H;

m is 1 or 2; and n is 1, 2 or 3;

or a pharmaceutically acceptable salt thereof.

In one aspect, the invention relates to a compound or pharmaceutically acceptable salt thereof, according to formula (I'),

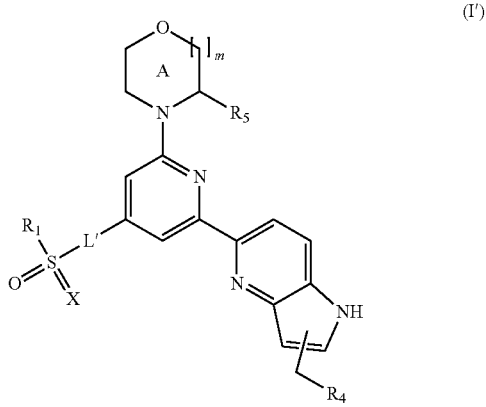

wherein:
A is

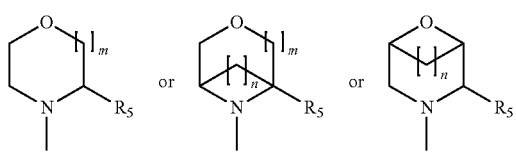

X is O or NH;
L' is (C$_1$-C$_3$)alkyl, (C$_1$-C$_3$)haloalkyl, (C$_3$-C$_5$) cycloalkyl or (C$_2$-C$_5$) heterocycloalkyl,
R$_1$ is (C$_1$-C$_3$)alkyl, (C$_3$-C$_5$) cycloalkyl, (C$_1$-C$_3$)alkoxy, or NR$_2$R$_3$,
  which (C$_1$-C$_3$)alkyl, (C$_3$-C$_5$)cycloalkyl or (C$_1$-C$_3$)alkoxy is optionally substituted with NR$_2$R$_3$;
R$_2$ and R$_3$ are each independently CH$_3$ or H;
R$_4$ is NH(C$_1$-C$_3$)alkyl, N((C$_1$-C$_3$)alkyl)$_2$, (C$_1$-C$_3$)alkyl, NH$_2$ or OH;
R$_5$ (C$_1$-C$_3$)alkyl or H;
m is 1 or 2;
n is 1, 2 or 3.

In one aspect, the invention relates to a compound according to formula (Ia),

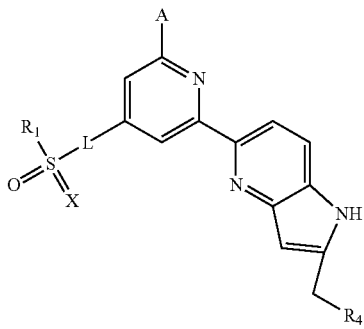

(Ia)

wherein:
A is

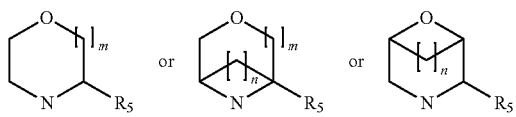

where ring A is attached via N;
X is O or NH;
L is (C$_1$-C$_3$)alkylene, (C$_1$-C$_3$)haloalkylene, (C$_3$-C$_5$)cycloalkylene or (C$_2$-C$_5$)heterocycloalkylene;
R$_1$ is (C$_1$-C$_3$)alkyl, (C$_3$-C$_5$) cycloalkyl, (C$_1$-C$_3$)alkoxy, or NR$_2$R$_3$,
  which (C$_1$-C$_3$)alkyl, (C$_3$-C$_5$)cycloalkyl or (C$_1$-C$_3$)alkoxy is optionally substituted with NR$_2$R$_3$;
R$_2$ and R$_3$ are each independently CH$_3$ or H;
R$_4$ is NH(C$_1$-C$_3$)alkyl, N((C$_1$-C$_3$)alkyl)$_2$, (C$_1$-C$_3$)alkyl, NH$_2$ or OH;
R$_5$ (C$_1$-C$_3$)alkyl or H;
m is 1 or 2; and
n is 1, 2 or 3;
or a pharmaceutically acceptable salt thereof.

In one embodiment, the invention relates to a compound or pharmaceutically acceptable salt thereof, according to formula (I'a),

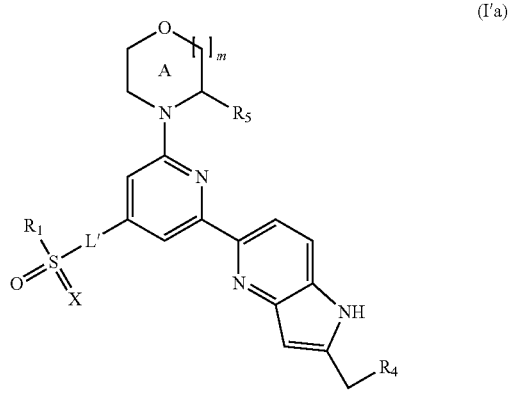

(I'a)

wherein:
A is

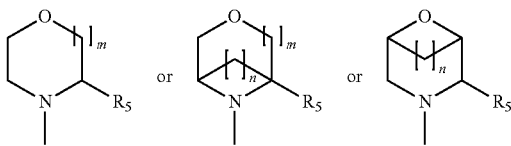

X is O or NH;
L' is (C$_1$-C$_3$)alkyl, (C$_1$-C$_3$)haloalkyl, (C$_3$-C$_5$)cycloalkyl or (C$_2$-C$_5$)heterocycloalkyl,
R$_1$ is (C$_1$-C$_3$)alkyl, (C$_3$-C$_5$) cycloalkyl, (C$_1$-C$_3$)alkoxy, or NR$_2$R$_3$,
  which (C$_1$-C$_3$)alkyl, (C$_3$-C$_5$)cycloalkyl or (C$_1$-C$_3$)alkoxy is optionally substituted with NR$_2$R$_3$;
R$_2$ and R$_3$ are each independently CH$_3$ or H;
R$_4$ is NH(C$_1$-C$_3$)alkyl, N((C$_1$-C$_3$)alkyl) (C$_1$-C$_3$)alkyl, NH$_2$ or OH;
R$_5$ is (C$_1$-C$_3$)alkyl or H;
m is 1 or 2;
n is 1, 2 or 3.

In one aspect, the invention relates to a compound according to formula (Ib),

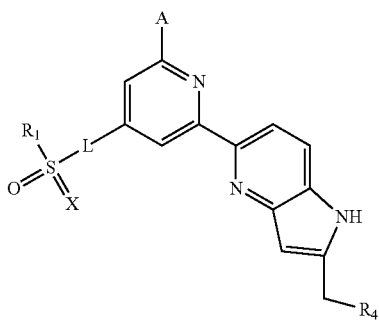

(Ib)

wherein:
A is

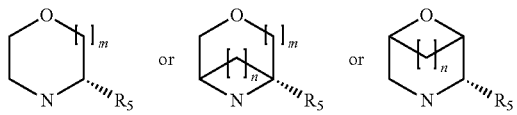

where ring A is attached via N;
X is O or NH;
L is (C₁-C₃)alkylene, (C₁-C₃)haloalkylene, (C₃-C₅)cycloalkylene or (C₂-C₅) heterocycloalkylene;
R₁ is (C₁-C₃)alkyl, (C₃-C₅) cycloalkyl, (C₁-C₃)alkoxy, or NR₂R₃,
which (C₁-C₃)alkyl, (C₃-C₅)cycloalkyl or (C₁-C₃)alkoxy is optionally substituted with NR₂R₃;
R₂ and R₃ are each independently CH₃ or H;
R₄ is NH(C₁-C₃)alkyl, N((C₁-C₃)alkyl)₂, (C₁-C₃)alkyl, NH₂ or OH;
R₅ is (C₁-C₃)alkyl or H;
m is 1 or 2; and
n is 1, 2 or 3;
or a pharmaceutically acceptable salt thereof.

In one embodiment, the invention relates to a compound or pharmaceutically acceptable salt thereof, according to formula (I'b),

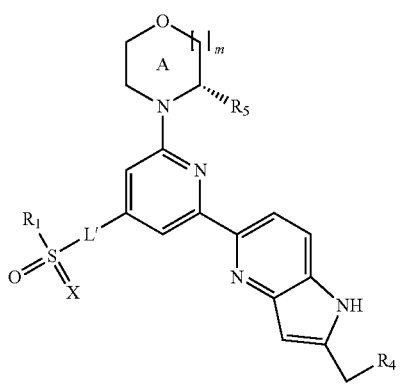

(I'b)

wherein:
A is

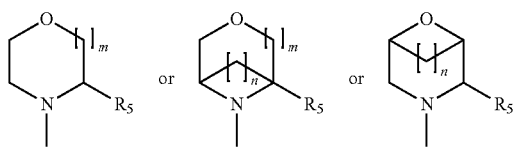

X is O or NH;
L' is (C₁-C₃)alkyl, (C₁-C₃)haloalkyl, (C₃-C₅) cycloalkyl or (C₃-C₅) heterocycloalkyl,
R₁ is (C₁-C₃)alkyl, (C₃-C₅) cycloalkyl, (C₁-C₃)alkoxy, or NR₂R₃,
which (C₁-C₃)alkyl, (C₃-C₅)cycloalkyl or (C₁-C₃)alkoxy is optionally substituted with NR₂R₃;
R₂ and R₃ are each independently CH₃ or H;
R₄ is NH(C₁-C₃)alkyl, N((C₁-C₃)alkyl)₂, (C₁-C₃)alkyl, NH₂ or OH;
R₅ is (C₁-C₃)alkyl or H;
m is 1 or 2;
n is 1, 2 or 3.

In one embodiment of the invention A is

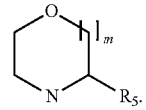

In another embodiment of the invention A is

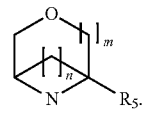

In a further embodiment of the invention A is

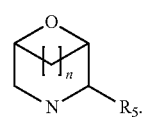

In one embodiment of the invention X is O. In one embodiment of the invention X is NH.

In one embodiment of the invention L' is (C₁-C₃)alkyl. In another embodiment of the invention L' is (C₁-C₃)haloalkyl. In a further embodiment of the invention L' is (C₃-C₅) cycloalkyl. In a still further embodiment of the invention L' is (C₂-C₅) heterocycloalkyl. In a yet further embodiment of the invention, L' is methyl, 2,2-propanyl, 1,1-cyclopropyl, difluoromethyl or tetrahydro-2H-pyran-4-yl. In further embodiment of the invention, L' is 2,2-propanyl.

In one embodiment of the invention L is (C₁-C₃)alkylene. In another embodiment of the invention L is (C₁-C₃)haloalkylene. In a further embodiment of the invention L is (C₃-C₅) cycloalkylene. In a still further embodiment of the invention L is (C₂-C₅) heterocycloalkylene. In a further embodiment of the invention, L links to the sulphur atom and the pyridine ring from the same carbon atom. In a yet further embodiment of the invention, L is methandiyl, propan-2,2-diyl, cyclopropan-1,1-diyl, difluoromethandiyl, tetrahydro-2H-pyran-4,4-diyl or piperidin-4,4-diyl. In a further embodiment of the invention, L is propan-2,2-diyl. In a further embodiment of the invention, L is tetrahydro-2H-pyran-4,4-diyl.

In one embodiment of the invention R is (C₁-C₃)alkyl, optionally substituted with NR₂R₃. In a further embodiment of the invention R₁ is (C₃-C₅) cycloalkyl, optionally substituted with NR₂R₃. In a still further embodiment of the invention R₁ is (C₁-C₃)alkoxy optionally substituted with NR₂R₃. In a yet embodiment of the invention R₁ is NR₂R₃. In another embodiment of the invention, R₁ is (C₁-C₃)alkyl, (C₃)cycloalkyl, or NR₂R₃. In further embodiment of the invention, R₁ is methyl, ethyl, cyclopropyl or N(CH₃)₂. In a further embodiment of the invention, R₁ is NH₂ or NHCH₃. In a still further embodiment of the invention R₁ is methyl.

In one embodiment of the invention R₄ is NHCH₃, N(CH₂)(CH₃), NH₂ or OH. In another embodiment of the invention R₄ is NHCH₃ or N(CH₂)(CH₃). In a further embodiment of the invention $R_4$ is $NHCH_3$. In another embodiment of the invention $R_4$ is $N(CH_2CH_3)(CH_3)$.

In one embodiment of the invention $R_5$ is methyl. In another embodiment of the invention $R_5$ is ethyl. In a further embodiment of the invention $R_5$ is H.

In one embodiment of the invention A is

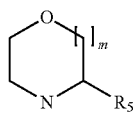

and $R_5$ is $(C_1-C_3)$alkyl.

In another embodiment of the invention A is

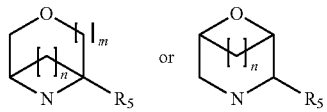

and $R_5$ is H.

In one embodiment of the invention m is 1. In another embodiment of the invention m is 2.

In one embodiment of the invention n is 1. In another embodiment of the invention n is 2. In further embodiment of the invention n is 3.

In one embodiment of the invention A is

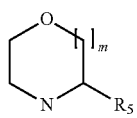

and m is 1.

In another embodiment of the invention A is

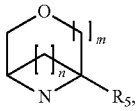

m is 1 and n is 2 or 3.

In another embodiment of the invention A is

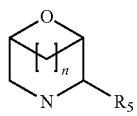

and n is 2.

In one embodiment, the invention relates to a compound or pharmaceutically acceptable salt thereof, according to formula (I'a),

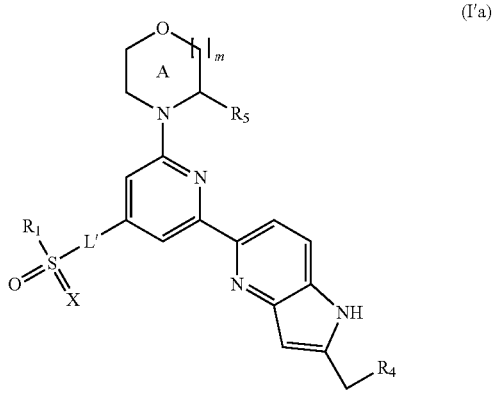

(I'a)

wherein
A is

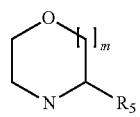

X is O;
L' is $(C_1-C_3)$ alkyl;
$R_1$ is $(C_1-C_3)$alkyl;
$R_4$ is $NHCH_3$;
$R_5$ is $(C_1-C_3)$alkyl; and
m is 1.

In one embodiment, the invention relates to a compound or pharmaceutically acceptable salt thereof, according to formula (I'a),

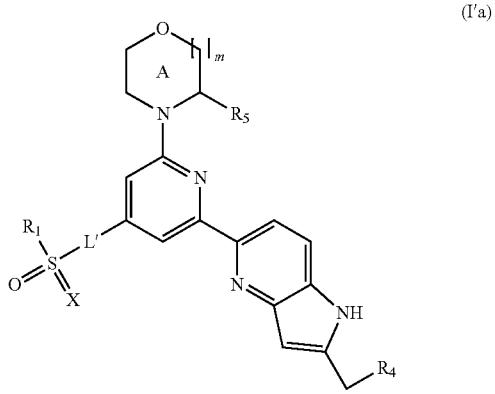

(I'a)

wherein
A is

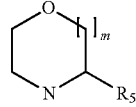

X is O;

L' is 2-propan-2-yl;

R₁ is methyl;

R₄ is NHCH₃;

R₅ is ethyl; and m is 1.

In one embodiment, the invention relates to a compound or pharmaceutically acceptable salt thereof, according to formula (Ia)

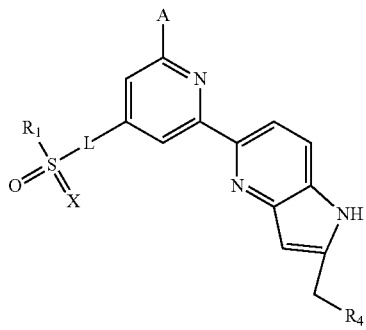

(Ia)

wherein

A is

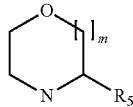

where ring A is attached via N;

X is O;

L is $(C_2-C_5)$heterocycloalkylene;

R₁ is $(C_1-C_3)$alkyl;

R₄ is NHCH₃;

R₅ is $(C_1-C_3)$alkyl; and m is 1.

In one embodiment, the invention relates to a compound or pharmaceutically acceptable salt thereof, according to formula (Ia)

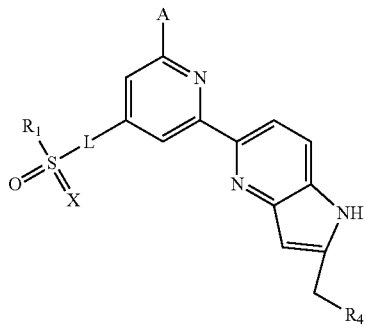

(Ia)

wherein

A is

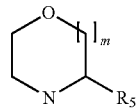

where ring A is attached via N;

X is O;

L is $(C_2-C_5)$heterocycloalkylene, containing 1 oxygen or nitrogen atom, linked to the sulphur atom and the pyridine ring from the same carbon atom;

R₁ is $(C_1-C_3)$alkyl;

R₄ is NHCH₃;

R₅ is $(C_1-C_3)$alkyl; and m is 1.

In one embodiment, the invention relates to a compound or pharmaceutically acceptable salt thereof, according to formula (Ia)

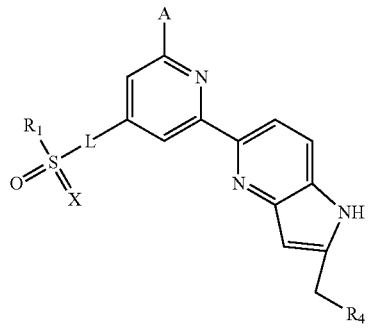

(Ia)

wherein

A is

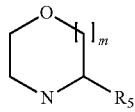

where ring A is attached via N;

X is O;

L is $(C_4-C_5)$heterocycloalkylene, containing 1 oxygen or nitrogen atom, linked to the sulphur atom and the pyridine ring from the same carbon atom;

R₁ is $(C_1-C_3)$alkyl;

R₄ is NHCH₃;

R₅ is $(C_1-C_3)$alkyl; and m is 1.

In one embodiment, the invention relates to a compound or pharmaceutically acceptable salt thereof, according to formula (Ia)

(Ia)

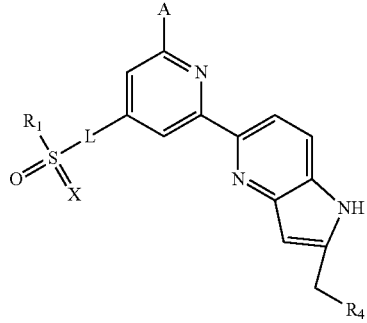

wherein
A is

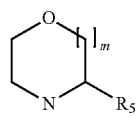

where ring A is attached via N;
X is O;
L is tetrahydro-2H-pyrandiyl linked to the sulphur atom and the pyridine ring from the same carbon atom;
$R_1$ is $(C_1\text{-}C_3)$alkyl;
$R_4$ is $NHCH_3$;
$R_5$ is $(C_1\text{-}C_3)$alkyl; and
m is 1.

In one embodiment, the invention relates to a compound or pharmaceutically acceptable salt thereof, according to formula (Ia)

(Ia)

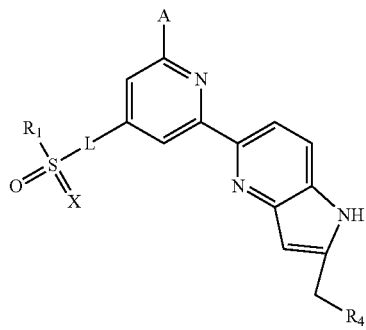

wherein
A is

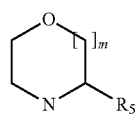

where ring A is attached via N;
X is O;
L is tetrahydro-2H-pyran-4,4-diyl;
$R_1$ is methyl;
$R_4$ is $NHCH_3$;
$R_5$ is ethyl; and
m is 1.

In one embodiment, the invention relates to a compound or pharmaceutically acceptable salt thereof, according to formula (Ib)

(Ib)

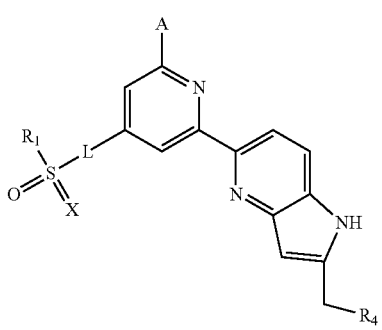

wherein
A is

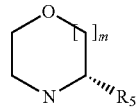

where ring A is attached via N;
X is O;
L is $(C_2\text{-}C_5)$heterocycloalkylene;
$R_1$ is $(C_1\text{-}C_3)$alkyl;
$R_4$ is $NHCH_3$;
$R_5$ is $(C_1\text{-}C_3)$alkyl; and
m is 1.

In one embodiment, the invention relates to a compound or pharmaceutically acceptable salt thereof, according to formula (Ib)

(Ib)

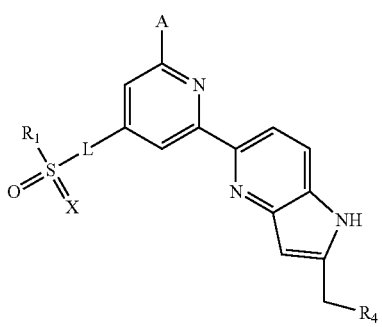

wherein
A is

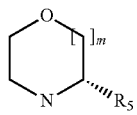

where ring A is attached via N;
X is O;
L is (C$_2$-C$_5$)heterocycloalkylene, containing 1 oxygen or nitrogen atom, linked to the sulphur atom and the pyridine ring from the same carbon atom;
R$_1$ is (C$_1$-C$_3$)alkyl;
R$_4$ is NHCH$_3$;
R$_5$ is (C$_1$-C$_3$)alkyl; and
m is 1.

In one embodiment, the invention relates to a compound or pharmaceutically acceptable salt thereof, according to formula (Ib)

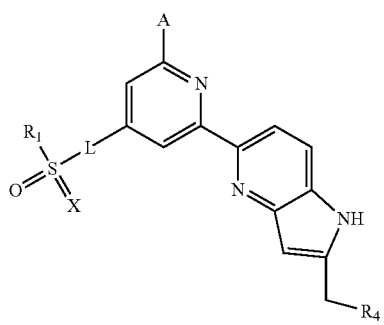

(Ib)

wherein
A is

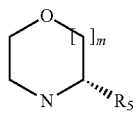

where ring A is attached via N;
X is O;
L is (C$_4$-C$_5$)heterocycloalkylene, containing 1 oxygen or nitrogen atom, linked to the sulphur atom and the pyridine ring from the same carbon atom;
R$_1$ is (C$_1$-C$_3$)alkyl;
R$_4$ is NHCH$_3$;
R$_5$ is (C$_1$-C$_3$)alkyl; and
m is 1.

In one embodiment, the invention relates to a compound or pharmaceutically acceptable salt thereof, according to formula (Ib)

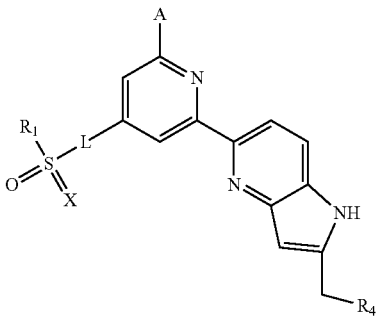

(Ib)

wherein
A is

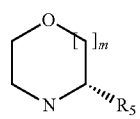

where ring A is attached via N;
X is O;
L is tetrahydro-2H-pyran-4,4-diyl;
R$_1$ is (C$_1$-C$_3$)alkyl;
R$_4$ is NHCH$_3$;
R$_5$ is (C$_1$-C$_3$)alkyl; and
m is 1.

In one embodiment, the invention relates to a compound or pharmaceutically acceptable salt thereof, according to formula (Ib)

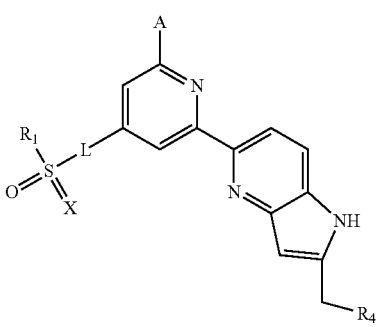

(Ib)

wherein
A is

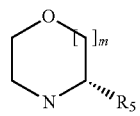

where ring A is attached via N;
X is O;
L is tetrahydro-2H-pyran-4,4-diyl;
R$_1$ is methyl;
R$_4$ is NHCH$_3$;
R$_5$ is ethyl; and
m is 1.

In one embodiment, the invention relates to a compound or pharmaceutically acceptable salt thereof, according to formula (I), which is selected from the group consisting of:

[(5-{6-[(3S)-3-ethylmorpholin-4-yl]-4-(2-methanesulfonylpropan-2-yl)pyridin-2-yl}-1H-pyrrolo[3,2-b]pyridin-2-yl)methyl](methyl)amine;

(S)—N-methyl-1-(5-(6-(3-methylmorpholino)-4-(2-(methylsulfonyl)propan-2-yl)pyridin-2-yl)-1H-pyrrolo[3,2-b]pyridin-2-yl)methanamine;

1-(5-(6-((1R,5S)-3-oxa-8-azabicyclo[3.2.1]octan-8-yl)-4-(2-(methylsulfonyl)propan-2-yl)pyridin-2-yl)-1H-pyrrolo[3,2-b]pyridin-2-yl)-N-methylmethanamine;

1-(5-(6-(8-oxa-3-azabicyclo[3.2.1]octan-3-yl)-4-(2-(methylsulfonyl)propan-2-yl)pyridin-2-yl)-1H-pyrrolo[3,2-b]pyridin-2-yl)-N-methylmethanamine;

1-(5-(6-(3-oxa-9-azabicyclo[3.3.1]nonan-9-yl)-4-(2-(methylsulfonyl)propan-2-yl)pyridin-2-yl)-1H-pyrrolo[3,2-b]pyridin-2-yl)-N-methylmethanamine;

(S)—N-methyl-1-(5-(6-(3-methylmorpholino)-4-((methylsulfonyl)methyl)pyridin-2-yl)-1H-pyrrolo[3,2-b]pyridin-2-yl)methanamine;

(S)—N-methyl-1-(5-(6-(3-(S)-1-(5-(4-(2-(ethylsulfonyl)propan-2-yl)-6-(3-methylmorpholino)pyridin-2-yl)-1H-pyrrolo[3,2-b]pyridin-2-yl)-N-methylmethanamine;

(S)-1-(5-(4-((cyclopropylsulfonyl)methyl)-6-(3-methylmorpholino)pyridin-2-yl)-1H-pyrrolo[3,2-b]pyridin-2-yl)-N-methylmethanamine;

(S)-1-(5-(4-(2-(cyclopropylsulfonyl)propan-2-yl)-6-(3-ethylmorpholino)pyridin-2-yl)-1H-pyrrolo[3,2-b]pyridin-2-yl)-N-methylmethanamine;

(S)-1-(5-(4-((cyclopropylsulfonyl)methyl)-6-(3-ethylmorpholino)pyridin-2-yl)-1H-pyrrolo[3,2-b]pyridin-2-yl)-N-methylmethanamine;

(S)-1-(5-(4-(1-(cyclopropylsulfonyl)cyclopropyl)-6-(3-ethylmorpholino)pyridin-2-yl)-1H-pyrrolo[3,2-b]pyridin-2-yl)-N-methylmethanamine;

(S)-1-(5-(4-(difluoro(methylsulfonyl)methyl)-6-(3-methylmorpholino)pyridin-2-yl)-1H-pyrrolo[3,2-b]pyridin-2-yl)-N-methylmethanamine;

(S)-1-(5-(6-(3-ethylmorpholino)-4-((methylsulfonyl)methyl)pyridin-2-yl)-1H-pyrrolo[3,2-b]pyridin-2-yl)-N-methylmethanamine;

(S)—N-((5-(6-(3-ethylmorpholino)-4-((methylsulfonyl)methyl)pyridin-2-yl)-1H-pyrrolo[3,2-b]pyridin-2-yl)methyl)-N-methylethanamine;

(S)-1-(5-(6-(3-ethylmorpholino)-4-(4-(methylsulfonyl)tetrahydro-2H-pyran-4-yl)pyridin-2-yl)-1H-pyrrolo[3,2-b]pyridin-2-yl)-N-methylmethanamine;

(S)—N-((5-(6-(3-ethylmorpholino)-4-(4-(methylsulfonyl)tetrahydro-2H-pyran-4-yl)pyridin-2-yl)-1H-pyrrolo[3,2-b]pyridin-2-yl)methyl)-N-methylethanamine; and (S)-1-(2-(3-ethylmorpholino)-6-(2-((methylamino)methyl)-1H-pyrrolo[3,2-b]pyridin-5-yl)pyridin-4-yl)-N,N-dimethylmethanesulfonamide.

In one embodiment, the invention relates to a compound or pharmaceutically acceptable salt thereof, according to formula (I), which is selected from the group consisting of:

[(5-{6-[(3S)-3-ethylmorpholin-4-yl]-4-(1-methanesulfonylcyclopropyl)pyridin-2-yl}-1H-pyrrolo[3,2-b]pyridin-2-yl)methyl](methyl)amine;

({5-[4-(1-methanesulfonylcyclopropyl)-6-[(3S)-3-methylmorpholin-4-yl]pyridin-2-yl]-1H-pyrrolo[3,2-b]pyridin-2-yl}methyl)(methyl)amine;

1-(5-{6-[(3S)-3-ethylmorpholin-4-yl]-4-(2-methanesulfonylpropan-2-yl)pyridin-2-yl}-1H-pyrrolo[3,2-b]pyridin-2-yl)methanamine;

1-(5-{6-[(3S)-3-ethylmorpholin-4-yl]-4-(4-methanesulfonyloxan-4-yl)pyridin-2-yl}-1H-pyrrolo[3,2-b]pyridin-2-yl)methanamine;

[(5-{6-[(3S)-3-ethylmorpholin-4-yl]-4-(4-methanesulfonylpiperidin-4-yl)pyridin-2-yl}-1H-pyrrolo[3,2-b]pyridin-2-yl)methyl](methyl)amine;

({5-[4-(methanesulfonylmethyl)-6-{8-oxa-3-azabicyclo[3.2.1]octan-3-yl}pyridin-2-yl]-1H-pyrrolo[3,2-b]pyridin-2-yl}methyl)(methyl)amine;

({5-[4-(methanesulfonylmethyl)-6-[(3R)-3-methylmorpholin-4-yl]pyridin-2-yl]-1H-pyrrolo[3,2-b]pyridin-2-yl}methyl)(methyl)amine;

4-{2-[(3S)-3-ethylmorpholin-4-yl]-6-{2-[(methylamino)methyl]-1H-pyrrolo[3,2-b]pyridin-5-yl}pyridin-4-yl}oxane-4-sulfonamide;

2-{2-[(3S)-3-ethylmorpholin-4-yl]-6-{2-[(methylamino)methyl]-1H-pyrrolo[3,2-b]pyridin-5-yl}pyridin-4-yl}propane-2-sulfonamide;

{2-[(3S)-3-ethylmorpholin-4-yl]-6-{2-[(methylamino)methyl]-1H-pyrrolo[3,2-b]pyridin-5-yl}pyridin-4-yl}methanesulfonamide;

1-{2-[(3S)-3-ethylmorpholin-4-yl]-6-{2-[(methylamino)methyl]-1H-pyrrolo[3,2-b]pyridin-5-yl}pyridin-4-yl}-N-methylmethanesulfonamide;

4-{2-[(3S)-3-ethylmorpholin-4-yl]-6-{2-[(methylamino)methyl]-1H-pyrrolo[3,2-b]pyridin-5-yl}pyridin-4-yl}-N,N-dimethyloxane-4-sulfonamide;

(5-{6-[(3S)-3-ethylmorpholin-4-yl]-4-(2-methanesulfonylpropan-2-yl)pyridin-2-yl}-1H-pyrrolo[3,2-b]pyridin-2-yl)methanol;

(5-{6-[(3S)-3-ethylmorpholin-4-yl]-4-(4-methanesulfonyloxan-4-yl)pyridin-2-yl}-1H-pyrrolo[3,2-b]pyridin-2-yl)methanol;

(5-{6-[(3S)-3-ethylmorpholin-4-yl]-4-(methanesulfonylmethyl)pyridin-2-yl}-1H-pyrrolo[3,2-b]pyridin-2-yl)methanol;

1-{2-[(3S)-3-ethylmorpholin-4-yl]-6-[2-(hydroxymethyl)-1H-pyrrolo[3,2-b]pyridin-5-yl]pyridin-4-yl}-N,N-dimethylmethanesulfonamide;

(5-{6-[(3S)-3-ethylmorpholin-4-yl]-4-(4-methanesulfonylpiperidin-4-yl)pyridin-2-yl}-1H-pyrrolo[3,2-b]pyridin-2-yl)methanol; and ({5-[4-(4-methanesulfonyloxan-4-yl)-6-{8-oxa-3-azabicyclo[3.2.1]octan-3-yl}pyridin-2-yl]-1H-pyrrolo[3,2-b]pyridin-2-yl}methyl)(methyl)amine.

In one embodiment, the invention relates to a compound or pharmaceutically acceptable salt thereof, according to formula (I), which is selected from the group consisting of:

(5-{6-[(3R)-3-ethylmorpholin-4-yl]-4-(methanesulfonylmethyl)pyridin-2-yl}-1H-pyrrolo[3,2-b]pyridin-2-yl)methyl](methyl)amine;

1-(4-{2-[(3S)-3-ethylmorpholin-4-yl]-6-{2-[(methylamino)methyl]-1H-pyrrolo[3,2-b]pyridin-5-yl}pyridin-4-yl}-4-methanesulfonylpiperidin-1-yl)ethan-1-one;

({5-[4-(4-methanesulfonyloxan-4-yl)-6-{3-oxa-8-azabicyclo[3.2.1]octan-8-yl}pyridin-2-yl]-1H-pyrrolo[3,2-b]pyridin-2-yl}methyl)(methyl)amine;

[(5-{6-[(3R)-3-ethylmorpholin-4-yl]-4-(4-methanesulfonyloxan-4-yl)pyridin-2-yl}-1H-pyrrolo[3,2-b]pyridin-2-yl)methyl](methyl)amine;

(5-{6-[(3R)-3-ethylmorpholin-4-yl]-4-(methanesulfonylmethyl)pyridin-2-yl}-1H-pyrrolo[3,2-b]pyridin-2-yl)methanol;

(5-{6-[(3R)-3-ethylmorpholin-4-yl]-4-(4-methanesulfonyloxan-4-yl)pyridin-2-yl}-1H-pyrrolo[3,2-b]pyridin-2-yl)methanol;

({5-[4-(methanesulfonylmethyl)-6-{6-oxa-3-azabicyclo [3.1.1]heptan-3-yl}pyridin-2-yl]-1H-pyrrolo[3,2-b]pyridin-2-yl}methyl)(methyl)amine;

({5-[4-(methanesulfonylmethyl)-6-(1,4-oxazepan-4-yl)pyridin-2-yl]-1H-pyrrolo[3,2-b]pyridin-2-yl}methyl)(methyl) amine;

({5-[4-(methanesulfonylmethyl)-6-(morpholin-4-yl)pyridin-2-yl]-1H-pyrrolo[3,2-b]pyridin-2-yl}methyl)(methyl) amine;

({5-[4-(methanesulfonylmethyl)-6-{3-oxa-8-azabicyclo [3.2.1]octan-8-yl}pyridin-2-yl]-1H-pyrrolo[3,2-b]pyridin-2-yl}methyl)(methyl)amine;

({5-[4-(methanesulfonylmethyl)-6-(3-propylmorpholin-4-yl)pyridin-2-yl]-1H-pyrrolo[3,2-b]pyridin-2-yl}methyl)(methyl)amine; and {5-[4-(methanesulfonylmethyl)-6-[3-(propan-2-yl)morpholin-4-yl]pyridin-2-yl]-1H-pyrrolo[3,2-b]pyridin-2-yl}methyl)(methyl)amine.

In one embodiment, the invention relates to a compound or pharmaceutically acceptable salt thereof, according to formula (Ia) which is [(5-{6-[(3S)-3-ethylmorpholin-4-yl]-4-(2-methanesulfonylpropan-2-yl)pyridin-2-yl}-1H-pyrrolo [3,2-b]pyridin-2-yl)methyl](methyl)amine.

In one embodiment, the invention relates to a compound or pharmaceutically acceptable salt thereof, according to formula (Ia) which is (S)-1-(5-(6-(3-ethylmorpholino)-4-(4-(methylsulfonyl)tetrahydro-2H-pyran-4-yl)pyridin-2-yl)-1H-pyrrolo[3,2-b]pyridin-2-yl)-N-methylmethanamine.

In one embodiment, the invention relates to a compound according to formula (Ia) which is [(5-{6-[(3S)-3-ethylmorpholin-4-yl]-4-(2-methanesulfonylpropan-2-yl)pyridin-2-yl}-1H-pyrrolo[3,2-b]pyridin-2-yl)methyl](methyl)amine.

In one embodiment, the invention relates to a compound according to formula (Ia) which is (S)-1-(5-(6-(3-ethylmorpholino)-4-(4-(methylsulfonyl)tetrahydro-2H-pyran-4-yl) pyridin-2-yl)-1H-pyrrolo[3,2-b]pyridin-2-yl)-N-methylmethanamine.

The compounds of formula (I) or formula (I') may contain one or more chiral centres, for example when X is NH, so that optical isomers, e.g. diastereoisomers may be formed. Accordingly, the present invention encompasses such isomers of the compounds of formula (I) or formula (I') whether as individual isomers isolated such as to be substantially free of the other isomer (i.e. pure) or as mixtures. An individual isomer isolated such as to be substantially free of the other isomer (i.e. pure) may be isolated such that less than 10%, particularly less than about 1%, for example less than about 0.1% of the other isomer is present.

Separation of isomers may be achieved by conventional techniques known to those skilled in the art, e.g. by fractional crystallisation, chromatography, HPLC or a combination of these techniques.

It is to be understood that the references herein to a compound of formula (I) or formula (I') or a pharmaceutically acceptable salt thereof includes a compound of formula (I) or formula (I') as a free base, or as a pharmaceutically acceptable salt thereof. Thus, in one embodiment, the invention is directed to a compound of formula (I). In one embodiment, the invention is directed to a compound of formula (I'). In another embodiment, the invention is directed to a pharmaceutically acceptable salt of a compound of formula (I). In another embodiment, the invention is directed to a pharmaceutically acceptable salt of a compound of formula (I').

'Pharmaceutically acceptable' refers to those compounds (including salts), materials, compositions, and dosage forms which are, within the scope of sound medical judgment, suitable for use in contact with the tissues of human beings and animals without excessive toxicity, irritation, or other problem or complication, commensurate with a reasonable benefit/risk ratio.

Pharmaceutically acceptable salts include, amongst others, those described in Berge, J. Pharm. Sci., 1977, 66, 1-19, or those listed in P H Stahl and C G Wermuth, editors, Handbook of Pharmaceutical Salts; Properties, Selection and Use, Second Edition Stahl/Wermuth: Wiley-VCH/VHCA, 2011 (see http://www.wiley.com/WileyCDA/WileyTitle/productCd-3906390519.html).

Non-pharmaceutically acceptable salts are within the scope of the present invention, for example for use as intermediates in the preparation of a compound of Formula (I) or formula (I') or a pharmaceutically acceptable salt thereof.

Suitable pharmaceutically acceptable salts can include acid addition salts.

Such acid addition salts can be formed by reaction of a compound of formula (I) or formula (I') (which, for example contains a basic amine or other basic functional group) with the appropriate acid, optionally in a suitable solvent such as an organic solvent, to give the salt which can be isolated by a variety of methods, including crystallisation and filtration.

Salts may be prepared in situ during the final isolation and purification of a compound of formula (I) or formula (I'). If a basic compound of formula (I) or formula (I') is isolated as a salt, the corresponding free base form of that compound may be prepared by any suitable method known to the art, including treatment of the salt with an inorganic or organic base.

It will be understood that if a compound of formula (I) or formula (I') contains two or more basic moieties, the stoichiometry of salt formation may include 1, 2 or more equivalents of acid. Such salts would contain 1, 2 or more acid counterions, for example, a dihydrochloride salt.

Stoichiometric and non-stoichiometric forms of a pharmaceutically acceptable salt of a compound of formula (I) or formula (I') are included within the scope of the invention, including sub-stoichiometric salts, for example where a counterion contains more than one acidic proton.

Representative pharmaceutically acceptable acid addition salts include, but are not limited to, 4-acetamidobenzoate, acetate, adipate, alginate, ascorbate, aspartate, benzenesulfonate (besylate), benzoate, bisulfate, bitartrate, butyrate, calcium edetate, camphorate, camphorsulfonate (camsylate), caprate (decanoate), caproate (hexanoate), caprylate (octanoate), cinnamate, citrate, cyclamate, digluconate, 2,5-dihydroxybenzoate, disuccinate, dodecylsulfate (estolate), edetate (ethylenediaminetetraacetate), estolate (lauryl sulfate), ethane-1,2-disulfonate (edisylate), ethanesulfonate (esylate), formate, fumarate, galactarate (mucate), gentisate (2,5-dihydroxybenzoate), glucoheptonate (gluceptate), gluconate, glucuronate, glutamate, glutarate, glycerophosphorate, glycolate, hexylresorcinate, hippurate, hydrabamine (N,N'-di(dehydroabietyl)-ethylenediamine), hydrobromide, hydrochloride, hydroiodide, hydroxynaphthoate, isobutyrate, lactate, lactobionate, laurate, malate, maleate, malonate, mandelate, methanesulfonate (mesylate), methylsulfate, mucate, naphthalene-1,5-disulfonate (napadisylate), naphthalene-2-sulfonate (napsylate), nicotinate, nitrate, oleate, palmitate, p-aminobenzenesulfonate, p-aminosalicylate, pamoate (embonate), pantothenate, pectinate, persulfate, phenylacetate, phenylethylbarbiturate, phosphate, polygalacturonate, propionate, p-toluenesulfonate (tosylate), pyroglutamate, pyruvate, salicylate, sebacate, stearate, subacetate, succinate, sulfamate, sulfate, tannate, tartrate, teoclate (8-chlorotheophyllinate), thiocyanate, triethiodide, undecanoate, undecylenate, and valerate.

The compounds of formula (I) or (I') may exist in a crystalline or non crystalline form, or as a mixture thereof. Pharmaceutically acceptable solvates may be formed for crystalline or non-crystalline compounds. In crystalline solvates, solvent molecules are incorporated into the crystalline lattice during crystallisation. Solvates may include non-aqueous solvents such as, but not limited to, ethanol, isopropanol, DMSO, acetic acid, ethanolamine, ethyl acetate, MeOH/TBME, MeCN/TBME or MeCN/Heptane or that may involve water as the solvent that is incorporated into the crystalline lattice. Solvates wherein water is the solvent incorporated into the crystalline lattice are typically referred to as "hydrates". Hydrates include stoichiometric hydrates as well as compositions containing variable amounts of water.

Compounds of the invention that exist in crystalline form, including the various solvates thereof, may exhibit polymorphism (i.e. the capacity to occur in different crystalline structures). These different crystalline forms are typically known as "polymorphs". Polymorphs have the same chemical composition, but differ in packing, geometrical arrangement, and other descriptive properties of the crystalline solid state. Polymorphs, therefore, may have different physical properties such as shape, density, hardness, deformability, stability and dissolution properties. Polymorphs typically exhibit different melting points, IR spectra, and X-ray diffraction patterns, which may be used for identification. Different polymorphs may be produced, for example, by changing or adjusting the reaction conditions or reagents used in making the compound. For example, changes in temperature, pressure, or solvent may result in polymorphs. In addition, one polymorph may spontaneously convert to another polymorph under certain conditions.

The present invention is further directed to certain crystalline forms of (S)-1-(5-(6-(3-ethylmorpholino)-4-(4-(methylsulfonyl)tetrahydro-2H-pyran-4-yl)pyridin-2-yl)-1H-pyrrolo[3,2-b]pyridin-2-yl)-N-methylmethanamine.

In one embodiment, a crystalline form of (S)-1-(5-(6-(3-ethylmorpholino)-4-(4-(methylsulfonyl)tetrahydro-2H-pyran-4-yl)pyridin-2-yl)-1H-pyrrolo[3,2-b]pyridin-2-yl)-N-methylmethanamine is characterised by a X-ray power diffraction (XRPD) pattern comprising at least nine diffraction angles, when measured using Cu Kα radiation, selected from a group consisting of about 8.7, 10.0, 13.5, 14.0, 14.4, 15.4, 15.7, 19.7, 21.3, 23.0 and 26.6. In another embodiment, (S)-1-(5-(6-(3-ethylmorpholino)-4-(4-(methylsulfonyl)tetrahydro-2H-pyran-4-yl)pyridin-2-yl)-1H-pyrrolo[3,2-b]pyridin-2-yl)-N-methylmethanamine is characterised by a X-ray power diffraction (XRPD) pattern comprising at least eight diffraction angles, or at least seven diffraction angles or at least six diffraction angles or at least five diffraction angles or at least four diffraction angles when measured using Cu Kα radiation, selected from a group consisting of about 8.7, 10.0, 13.5, 14.0, 14.4, 15.4, 15.7, 19.7, 21.3, 23.0 and 26.6. In one embodiment, a crystalline form of (S)-1-(5-(6-(3-ethylmorpholino)-4-(4-(methylsulfonyl)tetrahydro-2H-pyran-4-yl)pyridin-2-yl)-1H-pyrrolo[3,2-b]pyridin-2-yl)-N-methylmethanamine is characterised by a X-ray power diffraction (XRPD) pattern comprising at least three diffraction angles, when measured using Cu Kα radiation, selected from a group consisting of about 8.7, 10.0, 13.5, 14.0, 14.4, 15.4, 15.7, 19.7, 21.3, 23.0 and 26.6.

In still another embodiment, a crystalline form of (S)-1-(5-(6-(3-ethylmorpholino)-4-(4-(methylsulfonyl)tetrahydro-2H-pyran-4-yl)pyridin-2-yl)-1H-pyrrolo[3,2-b]pyridin-2-yl)-N-methylmethanamine is characterised by a X-ray power diffraction (XRPD) pattern comprising, measured using Cu Kα radiation, about 8.7, 10.0, 13.5, 14.0, 14.4, 15.4, 15.7, 19.7, 21.3, 23.0 and 26.6. In a further embodiment, a crystalline form of (S)-1-(5-(6-(3-ethylmorpholino)-4-(4-(methylsulfonyl)tetrahydro-2H-pyran-4-yl)pyridin-2-yl)-1H-pyrrolo[3,2-b]pyridin-2-yl)-N-methylmethanamine is characterised by a X-ray power diffraction (XRPD), substantially in accordance with FIG. 1.

Definitions

As used herein, the term "alkyl" represents a saturated, straight or branched hydrocarbon moiety having the specified number of carbon atoms. The term "($C_1$-$C_3$)alkyl" refers to an unsubstituted alkyl moiety containing 1, 2 or 3 carbon atoms; exemplary alkyls include methyl, ethyl and propyl. When present as a linking group (for example in the definition L'), this term may represent —$CH_2$—, —$CH_2$—$CH_2$—, —CH($CH_3$)—, —$CH_2$—$CH_2$—$CH_2$—, —CH($C_2H_5$)—, or —C($CH_3$)$_2$—.

As used herein, the term "alkylene" represents a saturated, straight or branched hydrocarbon moiety having the specified number of carbon atoms, with two points of attachment. The two points of attachment can be from the same or different carbon atoms. Suitably both points of attachment are from the same carbon atom. The term "($C_1$-$C_3$)alkylene" refers to an unsubstituted alkyl moiety containing 1, 2 or 3 carbon atoms with two points of attachment; exemplary ($C_1$-$C_3$)alkylene groups include methylene, ethylene and propylene.

As used herein, the term "($C_1$-$C_3$)haloalkyl" refers to a ($C_1$-$C_3$)alkyl as described above, substituted with 1, 2 or 3 halogen atoms per carbon. "Halo" means fluoro, chloro, bromo or iodo. Suitably, that halogen is fluoro or chloro.

As used herein, the term "($C_1$-$C_3$)haloalkylene" refers to a ($C_1$-$C_3$)alkylene moiety as described above, substituted with 1, 2 or 3 halogen atoms per carbon. In an embodiment, the ($C_1$-$C_3$)alkylene moiety is substituted with 1 or 2 halogen atoms per carbon. "Halo" means fluoro, chloro, bromo or iodo. Suitably, the halogen atom is fluoro or chloro. Exemplary ($C_1$-$C_3$)haloalkylene groups include fluoromethyldiyl and difluoromethyldiyl. As used herein, the term ($C_3$-$C_5$)cycloalkyl refers to unsubstituted cycloalkyl moiety containing 3, 4 or 5 carbon atoms; exemplary cycloalkyl groups include cyclopropyl, cyclobutyl or cyclopentyl.

As used herein, the term ($C_3$-$C_5$)cycloalkylene refers to an unsubstituted cycloalkylene moiety containing 3, 4 or 5 carbon atoms with two points of attachment. The two points of attachment can be from the same or different carbon atoms. Suitably both points of attachment are from the same carbon atom. Exemplary cycloalkylene groups include cyclopropan-1,1-diyl, cyclobutan-1,1-diyl or cyclopentane-1,1-diyl.

As used herein, the term ($C_2$-$C_5$)heteroalkyl refers to a cyclic moiety containing 2, 3, 4 or 5 carbon atoms in addition to 1 or 2 oxygen, sulphur or nitrogen atoms; exemplary ($C_2$-$C_5$) heteroalkyl groups include oxetane, tetrahydrofuran or tetrahydropyran.

As used herein, the term ($C_2$-$C_5$)heterocycloalkylene refers to a 3- to 7-membered cyclic moiety containing 2, 3, 4 or 5 carbon atoms in addition to 1 or 2 oxygen, sulphur or nitrogen atoms, with two points of attachment from the same or different carbon atoms. Suitably, the ($C_2$-$C_5$)heterocyclyalkylene group contains 1 oxygen or nitrogen atom. Suitably such group contains 3 carbon atoms and 1 oxygen or nitrogen atom, such as azetidindiyl or oxetandiyl. Suitably such group contains 4 or 5 carbon atoms and 1 oxygen or nitrogen atom, such as tetrahydrofurandiyl, tetrahydropyrandiyl, pyrrolidinyl or piperidindiyl. Suitably for such groups both points of attachment are from the same carbon atom. Exemplary ($C_2$-$C_5$)heterocyclylalkyl groups include azetidine-3,3-diyl, oxetan-3,3-diyl, tetrahydrofuran-3,3-diyl, tetrahydrofuran-4,4-diyl, piperidin-4,4-diyl or tetrahydro-2H-pyran-4,4-diyl.

As used herein, the term "optionally" means that the subsequently described event(s) may or may not occur, and includes both event(s) that occur and event(s) that do not occur.

As used herein, the term "treatment" refers to alleviating the specified condition, eliminating or reducing one or more symptoms of the condition, slowing or eliminating the progression of the condition, and delaying the reoccurrence of the condition in a previously afflicted or diagnosed patient or subject.

As used herein, the term "effective amount" means that amount of a drug or pharmaceutical agent that will elicit the biological or medical response of a tissue, system, animal, or human that is being sought, for instance, by a researcher or clinician.

The term "therapeutically effective amount" means any amount which, as compared to a corresponding subject who has not received such amount, results in improved treatment, healing, or amelioration of a disease, disorder, or side effect, or a decrease in the rate of advancement of a disease or disorder. The term also includes within its scope amounts effective to enhance normal physiological function.

Statement of Use

The compounds of formula (I) or formula (I') and pharmaceutically acceptable salts thereof are believed to be inhibitors of mTOR kinase, and thus have potential utility in the treatment of diseases or conditions for which an mTOR kinase inhibitor is indicated.

Thus, in one aspect of the invention, there is provided a compound of formula (I) or formula (I') or a pharmaceutically acceptable salt thereof for use in therapy. The compound of Formula (I) or formula (I') or a pharmaceutically acceptable salt thereof can be for use in the treatment of a disease or condition for which an mTOR kinase inhibitor is indicated.

In one aspect of the invention, there is provided a compound of formula (I) or formula (I') or a pharmaceutically acceptable salt thereof for the manufacture of a medicament for the treatment of a disease or condition for which an mTOR kinase inhibitor is indicated.

In one aspect of the invention, there is provided a method of treating a disease in which an mTOR kinase inhibitor is indicated in a subject in need thereof comprising administering to said subject a therapeutically amount of a compound according to formula (I) or formula (I'), or pharmaceutically acceptable salt thereof. In one embodiment of the invention, the subject in need thereof is a human subject.

Fibrotic diseases involve the formation of excess fibrous connective tissue in an organ or tissue in a reparative or reactive process. Inhibitors of mTOR are believed to be useful in the treatment of a variety of such diseases or conditions including those dependent on mTOR function. Diseases may include, but are not limited to lung fibrosis e.g. Idiopathic pulmonary fibrosis (IPF), Non-specific interstitial pneumonia (NSIP), Hypersensitivity pneumonitis (HP), Usual interstitial pneumonitis (UIP), Interstitial lung disease (ILD), progressive massive fibrosis, coal workers' pneumoconiosis, pigeon fancier's lung, familial pulmonary fibrosis, pulmonary fibrosis, connective tissue-interstitial lung disease (RA-ILD, SSc-ILD), Hermansky-Pudlak syndrome, airway fibrosis in asthma, airway fibrosis in COPD, ARDS associated fibrosis, acute lung injury, radiation-induced fibrosis, drug-induced fibrosis and pulmonary hypertension. Other pulmonary indications in which inhibitors of mTOR may be useful include COPD, lymphangioleiomyomatosis (LAM), obliterative bronchiolitis, asthma and granulomatous diseases such as sarcoidosis.

Non-lung fibrosis conditions in which inhibitors of mTOR may be useful include renal fibrosis (chronic kidney disease (CKD), end-stage renal disease (ESRD), diabetic nephropathy, IgA nephropathy, lupus nephritis, focal segmental glomerulosclerosis (FSGS), tubulointerstitial fibrosis, transplant nephropathy, autoimmune nephropathy, drug-induced nephropathy, hypertension-related nephropathy, nephrogenic systemic fibrosis); hepatic fibrosis (virally-induced fibrosis (e.g. hepatitis C or B), autoimmune hepatitis, primary biliary cirrhosis, alcoholic liver disease, non-alcoholic fatty liver disease (NAFLD) including non-alcoholic steatohepatitis (NAS H), congenital hepatic fibrosis, primary sclerosing cholangitis, drug-induced hepatitis, hepatic cirrhosis); skin fibrosis (hypertrophic scars, scleroderma, keloid scarring, dermatomyositis, eosinophilic fasciitis, Dupytrens contracture, Ehlers-Danlos syndrome, Peyronie's disease, epidermolysis bullosa dystrophica, oral submucous fibrosis); ocular fibrosis (age-related macular degeneration (AMD), diabetic macular oedema, dry eye, glaucoma) corneal scarring, corneal injury and corneal wound healing, prevention of filter bleb scarring post trabeculectomy surgery; cardiac fibrosis (congestive heart failure, atherosclerosis, myocardial infarction, endomyocardial fibrosis, hypertrophic cardiomyopathy (HCM)) and other miscellaneous fibrotic conditions (mediastinal fibrosis, myelofibrosis, retroperitoneal fibrosis, Crohn's disease, neurofibromatosis, uterine leiomyomas (fibroids), chronic organ transplant rejection.

In addition, oncology indications in which inhibitors of mTOR may be useful include Pre-cancerous lesions or cancers associated with mTOR (endometrial, basal cell, liver, colon, cervical, oral, pancreas, breast and ovarian cancers, Kaposi's sarcoma, giant cell tumours and cancer associated stroma); non-small cell lung cancer; non-hodgkins lymphoma, relapsed or refractory advanced solid tumours, advanced malignant solid neoplasm, locally advanced or metastatic solid tumours and soft tissue sarcomas.

Furthermore, diseases characterized by mutations in PI3k/mTOR including tuberous sclerosis, Smith-Kingsmore syndrome, focal cortical dysplasia and oncology indications, those conditions where the treatment of rapalogues such as sirolimus and everolimus are permitted (transplant recipients, rescue immunosuppression and chronic graft versus host disease) and diseases related to obesity (adipose tissue inflammation) and metabolic disorders (diabetes) or diseases related to ageing.

The term "disease or condition for which an mTOR kinase inhibitor is indicated" is intended to include any or all of the above disease states.

In one embodiment the disease or condition for which an mTOR kinase inhibitor is indicated is pulmonary fibrosis including idiopathic pulmonary fibrosis and any condition characterised by excessive tissue scarring affecting the skin, liver, kidney or heart. In a further embodiment the disease or condition for which an mTOR kinase inhibitor is indicated is idiopathic pulmonary fibrosis.

Biomarkers

Clinically, mTOR activity may be assessed in combination with recently identified biomarkers shown to correlate with disease severity (BGM, C1M, C3A, C3M, C6M, CRPM) in a cohort of patients with IPF or NSIP (Jenkins et al., 2015).

In one embodiment, there is provided a method for treating a subject suffering from idiopatic pulmonary fibrosis, the method comprising:
a) detecting an amount of one, two, three, four, five or six biomarkers selected from the group consisting of BGM, C1M, C3A, C3M, C6M, or CRPM in a sample of the subject;
b) comparing the amount of the one, two, three, four, five or six biomarkers to a reference amount of the one, two, three, four, five or six biomarkers;
c) identifying the subject as having an increased risk for disease progression if the amount of the one, two, three, four, five or six biomarkers in the sample is greater than the reference amount of the one, two, three, four, five or six biomarkers; and
d) treating the subject with a compound of the invention or a pharmaceutical acceptable salt thereof if the subject is identified as having an increased risk for disease progression.

Additional biomarkers of collagen synthesis (PRO-C3, PRO-C6, P1NP) may also be used to measure a therapeutic response to mTOR modulation in patients. Serum levels of PRO-C3 and PRO-C6 correlate with disease progression in patients with IPF (conference poster ICLAF 2018).

Therefore, in one embodiment, there is provided an in vitro method for monitoring statement of a subject diagnosed with idiopathic pulmonary fibrosis, comprising:
 a) Determining the amount of one, two or three biomarkers, selected from the group consisting of PRO-C3, PRO-C6, and P1NP in a first baseline biological sample of a patient
 b) Treating the subject with a compound of the invention
 c) Determining the amount of one, two or three biomarkers, selected from the group consisting of PRO-C3, PRO-C6, and P1NP in a second biological sample of a patient, taken on a separate occasion
 d) Comparing the levels of the biomarkers obtained in step a with the levels of the biomarkers obtained in step c, and classifying the treatment as effective if the levels have not risen further over time or have declined with treatment.

Pharmaceutical Compositions/Routes of Administration/Dosages

While it is possible that for use in therapy, a compound of formula (I) or formula (I') as well as pharmaceutically acceptable salts thereof may be administered as the raw chemical, it is common to present the active ingredient as a pharmaceutical composition.

The present invention therefore provides in a further aspect a pharmaceutical composition comprising a compound of formula (I) or formula (I') or a pharmaceutically acceptable salt thereof and a pharmaceutically acceptable carrier, diluents or excipient. The compound of formula (I) or formula (I') and pharmaceutically acceptable salts thereof are as described above. The carrier, diluent or excipient must be acceptable in the sense of being compatible with the other ingredients of the composition and not deleterious to the recipient thereof.

In accordance with another aspect of the invention there is also provided a process for the preparation of a pharmaceutical composition including admixing a compound of the formula (I) or formula (I'), or a pharmaceutically acceptable salt thereof, with a pharmaceutically acceptable carrier, diluent or excipient. The pharmaceutical composition can be for use in the treatment of any of the conditions described herein.

Further provided is a pharmaceutical composition for the treatment of diseases or conditions for which an mTOR kinase inhibitor is indicated, comprising a compound of formula (I) or formula (I') or a pharmaceutically acceptable salt thereof.

Further provided is a pharmaceutical composition comprising 0.05 to 1000 mg of a compound of formula (I) or formula (I') or a pharmaceutical salt thereof and 0.1 to 2 g of a pharmaceutically acceptable carrier, diluent or excipient.

Since the compounds of formula (I) or formula (I') are intended for use in pharmaceutical compositions it will be readily understood that they are each preferably provided in substantially pure form, for example, at least 60% pure, more suitably at least 75% pure and preferably at least 85% pure, especially at least 98% pure (% in a weight for weight basis).

Pharmaceutical compositions may be presented in unit dose forms containing a predetermined amount of active ingredient per unit dose. Preferred unit dosage compositions are those containing a daily dose or sub-dose, or an appropriate fraction thereof, of an active ingredient. Such unit doses may therefore be administered more than once a day. Preferred unit dosage compositions are those containing a daily dose or sub-dose (for administration more than once a day), as herein above recited, or an appropriate fraction thereof, of an active ingredient.

Pharmaceutical compositions may be adapted for administration by any appropriate route, for example by the oral (including buccal or sublingual), rectal, inhaled, intranasal, topical (including buccal, sublingual or transdermal), vagina, ocular or parenteral (including subcutaneous, intramuscular, intravenous or intradermal) route. Such compositions may be prepared by any method known in the art of pharmacy, for example by bringing into association the active ingredient with the carrier or excipient.

In one embodiment the pharmaceutical composition is adapted for oral administration.

Pharmaceutical compositions adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

For instance, for oral administration in the form of a tablet or capsule, the active drug component can be combined with an oral, non-toxic pharmaceutically acceptable inert carrier such as ethanol, glycerol, water and the like. Powders suitable for incorporating into tablets or capsules may be prepared by reducing the compound to a suitable fine particle size (e.g. by micronisation) and mixing with a similarly prepared pharmaceutical carrier such as an edible carbohydrate, as, for example, starch or mannitol. Flavoring, preservative, dispersing and coloring agent can also be present.

Capsules may be made by preparing a powder mixture, as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilising agent such as agaragar, calcium carbonate or sodium carbonate can also be added to improve the availability of the medicament when the capsule is ingested.

Moreover, when desired or necessary, suitable binders, glidants, lubricants, sweetening agents, flavours, disintegrating agents and coloring agents can also be incorporated into the mixture.

Oral fluids such as solution, syrups and elixirs can be prepared in dosage unit form so that a given quantity contains a predetermined amount of the compound. Syrups can be prepared by dissolving the compound in a suitably flavoured aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavour additive such as peppermint oil or natural sweeteners or saccharin or other artificial sweeteners, and the like can also be added.

Where appropriate, dosage unit compositions for oral administration can be microencapsulated. The formulation can also be prepared to prolong or sustain the release as for example by coating or embedding particulate material in polymers, wax or the like.

The compounds of the invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The compounds of the invention may also be prepared as an amorphous molecular dispersion in a polymer matrix, such as hydroxypropylmethyl cellulose acetate succinate, using a spray-dried dispersion (SDD) process to improve the stability and solubility of the drug substance.

The compounds of the invention may also be delivered using a liquid encapsulation technology to improve properties such as bioavailability and stability, in either liquid or semi-solid filled hard capsule or soft gelatin capsule formats.

Pharmaceutical compositions adapted for transdermal administration may be presented as discrete patches intended to remain in intimate contact with the epidermis of the recipient for a prolonged period of time.

Pharmaceutical compositions adapted for topical administration may be formulated as ointments, creams, suspensions, lotions, powders, solutions, pastes, gels, sprays, aerosols or oils.

In another aspect, the invention is directed to a dosage form adapted for administration to a patient by nasal or inhaled administration, for example, as a dry powder, an aerosol, a suspension, or a solution formulation.

Dry powder formulations for delivery to the lung by inhalation typically comprise a compound of formula (I) or formula (I') or a pharmaceutically acceptable salt thereof as a finely divided powder together with one or more pharmaceutically-acceptable excipients as finely divided powders. Pharmaceutically-acceptable excipients particularly suited for use in dry powders are known to those skilled in the art and include lactose, starch, mannitol, and mono-, di-, and polysaccharides. The finely divided powder may be prepared by, for example, micronisation and milling. Generally, the size-reduced (eg micronised) compound can be defined by a $D_{50}$ value of about 1 to about 10 microns (for example as measured using laser diffraction).

The dry powder may be administered to the patient via a reservoir dry powder inhaler (RDPI) having a reservoir suitable for storing multiple (un-metered doses) of medicament in dry powder form. RDPIs typically include a means for metering each medicament dose from the reservoir to a delivery position. For example, the metering means may comprise a metering cup, which is movable from a first position where the cup may be filled with medicament from the reservoir to a second position where the metered medicament dose is made available to the patient for inhalation.

The dry powder formulations for use in accordance with the present invention may be administered via inhalation devices. As an example, such devices can encompass capsules and cartridges of for example gelatin, or blisters of, for example, laminated aluminum foil. In various embodiments, each capsule, cartridge or blister may contain doses of formulation according to the teachings presented herein. Examples of inhalation devices may include those intended for unit dose or multi-dose delivery of formulation, including all of the devices set forth herein. As an example, in the case of multi-dose delivery, the formulation can be pre-metered (e.g., as in Diskus®, see GB2242134, U.S. Pat. Nos. 6,032,666, 5,860,419, 5,873,360, 5,590,645, 6,378,519 and 6,536,427 or Diskhaler, see GB 2178965, 2129691 and 2169265, U.S. Pat. Nos. 4,778,054, 4,811,731, 5,035,237) or metered in use (e.g. as in Turbuhaler, see EP 69715, or in the devices described in U.S. Pat. No. 6,321,747). An example of a unit-dose device is Rotahaler (see GB 2064336). In one embodiment, the Diskus® inhalation device comprises an elongate strip formed from a base sheet having a plurality of recesses spaced along its length and a lid sheet peelably sealed thereto to define a plurality of containers, each container having therein an inhalable formulation containing the compound optionally with other excipients and additive taught herein. The peelable seal is an engineered seal, and in one embodiment the engineered seal is a hermetic seal. Preferably, the strip is sufficiently flexible to be wound into a roll. The lid sheet and base sheet will preferably have leading end portions which are not sealed to one another and at least one of the leading end portions is constructed to be attached to a winding means. Also, preferably the engineered seal between the base and lid sheets extends over their whole width. The lid sheet may preferably be peeled from the base sheet in a longitudinal direction from a first end of the base sheet.

A dry powder formulation may also be presented in an inhalation device which permits separate containment of two different components of the formulation, Thus, for example, these components are administrable simultaneously but are stored separately, e.g. in separate pharmaceutical formulations, for example as described in WO 03/061743 A1 WO 2007/012871 A1, WO2007/068896, as well as U.S. Pat. Nos. 8,113,199, 8,161,968, 8,511,304, 8,534,281, 8,746,242 and 9,333,310.

In one embodiment an inhalation device permitting separate containment of components is an inhaler device having two peelable blister strips, each strip containing pre-metered doses in blister pockets arranged along its length, e.g., multiple containers within each blister strip, e.g., ELLIPTA®. Said device has an internal indexing mechanism which, each time the device is actuated, peels opens a pocket of each strip and positions the blisters so that each newly exposed dose of each strip is adjacent to the manifold which communicates with the mouthpiece of the device. When the patient inhales at the mouthpiece, each dose is simultaneously drawn out of its associated pocket into the manifold and entrained via the mouthpiece into the patient's respiratory tract. A further device that permits separate containment of different components is DUOHALER™ of Innovata. In addition, various structures of inhalation devices provide for the sequential or separate delivery of the pharmaceutical formulation(s) from the device, in addition to simultaneous delivery.

Alternatively, the dry powder may be presented in capsules (e.g. gelatin or plastic), cartridges, or blister packs for use in a multi-dose dry powder inhaler (MDPI). MDPIs are inhalers wherein the medicament is comprised within a multi-dose pack containing (or otherwise carrying) multiple defined doses (or parts thereof) of medicament. When the dry powder is presented as a blister pack, it comprises multiple blisters for containment of the medicament in dry powder form. The blisters are typically arranged in regular fashion for ease of release of the medicament therefrom. For example, the blisters may be arranged in a generally circular fashion on a disc-form blister pack, or the blisters may be elongate in form, for example comprising a strip or a tape. Each capsule, cartridge, or blister may, for example, contain between 200 µg-10 mg of the compound of formula (I) or formula (I') or a pharmaceutically acceptable salt thereof.

Aerosols may be formed by suspending or dissolving a compound of formula (I) or formula (I') or a pharmaceutically acceptable salt thereof in a liquified propellant. Suitable propellants include halocarbons, hydrocarbons, and other liquified gases. Representative propellants include: trichlorofluoromethane (propellant 11), dichlorofluoromethane (propellant 12), dichlorotetrafluoroethane (propellant 114), tetrafluoroethane (HFA-134a), 1,1-difluoroethane (HFA-152a), difluoromethane (HFA-32), pentafluoroethane (HFA-12), heptafluoropropane (HFA-227a), perfluoropropane, perfluorobutane, perfluoropentane, butane, isobutane, and pentane. Aerosols comprising a compound of formula (I) or formula (I') or a pharmaceutically acceptable salt thereof will typically be administered to a patient via a metered dose inhaler (MDI). Such devices are known to those skilled in the art.

A therapeutically effective amount of a compound of formula (I) or formula (I') or a pharmaceutically acceptable salt thereof (hereinafter a compound of the invention) will depend upon a number of factors including, for example, the age and weight of the subject, the precise condition requiring treatment and its severity, the nature of the formulation, and the route of administration, and will ultimately be at the discretion of the attendant physician or veterinarian.

In the pharmaceutical composition, each dosage unit for oral or parenteral administration may contain from 0.01 to 3000 mg, or 0.1 to 2000 mg, or more typically 0.5 to 1000 mg of a compound of the invention calculated as the parent compound.

Each dosage unit for nasal or inhaled administration preferably contains from 0.001 to 50 mg, more preferably 0.01 to 5 mg, yet more preferably 1 to 50 mg, of a compound of the invention.

For administration of a nebulised solution or suspension, a dosage unit typically contains from 1 to 15 mg which may suitably be delivered once daily, twice daily or more than twice daily. The compound of the invention may be provided in a dry or lyophilised powder for reconstitution in the pharmacy or by the patient, or may, for example, be provided in an aqueous saline solution.

The compounds of the invention can be administered in a daily dose (for an adult patient) of, for example, an oral or parenteral dose of 0.01 mg to 3000 mg per day, or 0.5 to 1000 mg per day or 0.5 to 300 mg per day, or 2 to 300 mg per day, or a nasal or inhaled dose of 0.001 to 50 mg per day or 0.01 to 50 mg per day, or 1 to 50 mg per day, of the compound of the invention. This amount may be given in a single dose per day or more usually in a number (such as two, three, four, five or six) of sub-doses per day such that the total daily dose is the same. An effective amount of a salt thereof may be determined as a proportion of the effective amount of the compound of formula (I) or formula (I') per se.

The compounds of the invention may be employed alone or in combination with other therapeutic agents. Combination therapies according to the present invention thus comprise the administration of at least one compound of formula (I) or formula (I') or a pharmaceutically acceptable salt thereof, and the use of at least one other pharmaceutically active agent. Preferably, combination therapies according to the present invention comprise the administration of at least one compound of formula (I) or formula (I') or a pharmaceutically acceptable salt thereof, and at least one other pharmaceutically active agent. The compound(s) of the invention and the other pharmaceutically active agent(s) may be administered together in a single pharmaceutical composition or separately and, when administered separately this may occur simultaneously or sequentially in any order. The amounts of the compound(s) of the invention and the other pharmaceutically active agent(s) and the relative timings of administration will be selected in order to achieve the desired combined therapeutic effect.

Thus in a further aspect, there is provided a combination comprising a compound of the invention and at least one other pharmaceutically active agent.

Thus in one aspect, the compound and pharmaceutical compositions according to the invention may be used in combination with or include one or more other therapeutic agents, including therapies for allergic disease, inflammatory disease, autoimmune disease, anti-fibrotic therapies and therapies for obstructive airway disease, therapies for diabetes and related diseases, ocular diseases, and therapies for corneal scarring, corneal injury and corneal wound healing.

Anti-allergic therapies include antigen immunotherapy (such as components and fragments of bee venom, pollen, milk, peanut, CpG motifs, collagen, other components of extracellular matrix which may be administered as oral or sublingual antigens), anti-histamines (such as cetirizine, loratidine, acrivastine, fexofenidine, chlorphenamine), and corticosteroids (such as fluticasone propionate, fluticasone furoate, beclomethasone dipropionate, budesonide, ciclesonide, mometasone furoate, triamcinolone, flunisolide, prednisolone, hydrocortisone).

Anti-inflammatory therapies include NSAIDs (such as aspirin, ibuprofen, naproxen), leukotriene modulators (such as montelukast, zafirlukast, pranlukast), and other anti-inflammatory therapies (such as iNOS inhibitors, tryptase inhibitors, IKK2 inhibitors, p38 inhibitors (losmapimod, dilmapimod), elastase inhibitors, beta2 agonists, DPi antagonists, DP2 antagonists, pI3K delta inhibitors, ITK inhibitors, LP (lysophosphatidic) inhibitors or FLAP (5-lipoxygenase activating protein) inhibitors (such as sodium 3-(3-(tert-butylthio)-1-(4-(6-ethoxypyridin-3-yl)benzyl)-5-((5-methylpyridin-2-yl)methoxy)-1H-indol-2-yl)-2,2-dimethylpropanoate); adenosine a2a agonists (such as adenosine and regadenoson), chemokine antagonists (such as CCR3 antagonists or CCR4 antagonists), mediator release inhibitors.

Therapies for autoimmune disease include DMARDS (such as methotrexate, leflunomide, azathioprine), biopharmaceutical therapies (such as anti-IgE, anti-TNF, anti-interleukins (such as anti-IL-1, anti-IL-6, anti-IL-12, anti-IL-17, anti-IL-18), receptor therapies (such as etanercept and similar agents); antigen non-specific immunotherapies (such as interferon or other cytokines/chemokines, cytokine/chemokine receptor modulators, cytokine agonists or antagonists, TLR agonists and similar agents).

Other anti-fibrotic therapies includes inhibitors of TGFβ synthesis (such as pirfenidone), tyrosine kinase inhibitors targeting the vascular endothelial growth factor (VEGF), platelet-derived growth factor (PDGF) and fibroblast growth factor (FGF) receptor kinases (such as Nintedanib (BIBF-1120) and imatinib mesylate (Gleevec)), endothelin receptor antagonists (such as ambrisentan or macitentan), antioxidants (such as N-acetylcysteine (NAC); broad-spectrum antibiotics (such as cotrimoxazole, tetracyclines (minocycline hydrochloride)), phosphodiesterase 5 (PDE5) inhibitors (such as sildenafil), anti-avpx antibodies and drugs (such as anti-αvβ6 monoclonal antibodies such as those described in WO2003100033A2 may be used in combination, intetumumab, cilengitide) may be used in combination.

Therapies for obstructive airway diseases include bronchodilators such as short-acting 32-agonists, such as salbutamol), long-acting β2-agonists (such as salmeterol, formoterol and vilanterol), short-acting muscarinic antagonists (such as ipratropium bromide), long-acting muscarinic antagonists, (such as tiotropium, umeclidinium).

In some embodiments, treatment can also involve combination of a compound of this invention with other existing modes of treatment, for example existing agents for treatment of diabetic ocular diseases, such as anti VEGF therapeutics e.g. Lucentis, Avastin, and Aflibercept and steroids, e.g., triamcinolone, and steroid implants containing fluocinolone acetonide.

In some embodiments, treatment can also involve combination of a compound of this invention with other existing modes of treatment, for example existing agents for treatment of corneal scarring, corneal injury or corneal wound healing, such as Gentel, calf blood extract, Levofloxacin, and Ofloxacin.

The compounds and compositions of the invention may be used to treat cancers alone or in combination with cancer therapies including chemotherapy, radiotherapy, targeted agents, immunotherapy and cell or gene therapy.

Rapamycin (sirolimus) and analogues of rapamycin (everolimus, ridaforolimus, temsirolimus, zotarolimus) may be used in combination with mTOR kinase inhibitors to augment mTOR modulation as described for an everolimus combination with a pan PI3k/mTOR inhibitor (Nyfeler et al., 2012)

Therefore, in one embodiment, there is provided a combination of
 a) a compound or pharmaceutically acceptable salt of the invention; and
 b) Rapaycin or an analogue of rapamycin.

In another embodiment, there is provided a combination of
 a) a compound or pharmaceutically acceptable salt of the invention; and
 b) A compound selected from the group consisting of Sirolimus, Everolimus, Ridaforolimus, Temsirolimus, Zotarolimus and pharmaceutically acceptable salts thereof.

In one embodiment there is provided a composition comprising
 a) a compound or pharmaceutically acceptable salt of the invention; and
 b) Rapaycin or an analogue of rapamycin.

In another embodiment there is provided a composition comprising
 a) a compound or pharmaceutically acceptable salt of the invention; and
 b) A compound selected from the group consisting of Sirolimus, Everolimus, Ridaforolimus, Temsirolimus, Zotarolimus and pharmaceutically acceptable salts thereof.

In one embodiment there is provided a method for treatment of idiopathic pulmonary fibrosis in a human in need thereof comprising administering to said human a therapeutically effective amount of:
 a) a compound or pharmaceutically acceptable salt of the invention; and
 b) Rapaycin or an analogue of rapamycin.

In another embodiment there is provided a method for treatment of idiopathic pulmonary fibrosis in a human in need thereof comprising administering to said human a therapeutically effective amount of:
 a) a compound or pharmaceutically acceptable salt of the invention; and
 b) A compound selected from the group consisting of Sirolimus, Everolimus, Ridaforolimus, Temsirolimus, Zotarolimus and pharmaceutically acceptable salts thereof.

The combinations referred to above may conveniently be presented for use in the form of a pharmaceutical composition and thus pharmaceutical compositions comprising a combination as defined above together with a pharmaceutically acceptable diluent or carrier represent a further aspect of the invention. The individual compounds of such combinations may be administered either sequentially or simultaneously in separate or combined pharmaceutical compositions. Preferably, the individual compounds will be administered simultaneously in a combined pharmaceutical composition. Appropriate doses of known therapeutic agents will be readily appreciated by those skilled in the art.

It will be appreciated that when the compound of the present invention is administered in combination with one or more other therapeutically active agents normally administered by the inhaled, intravenous, oral, intranasal, ocular topical or other route that the resultant pharmaceutical composition may be administered by the same route. Alternatively, the individual components of the composition may be administered by different routes.

General Synthetic Routes

General Scheme a)

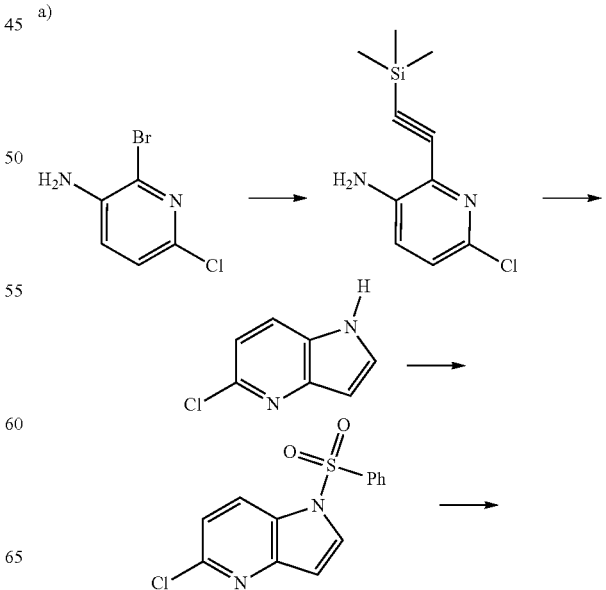

33

-continued

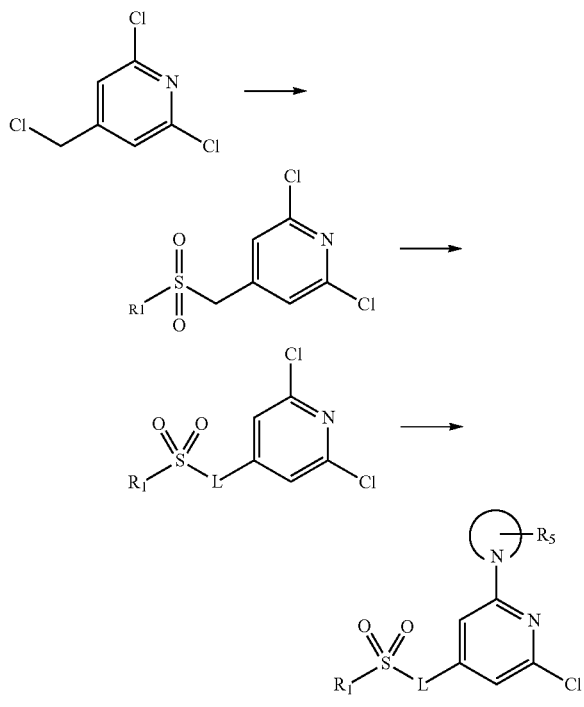

b)

c)

34

-continued

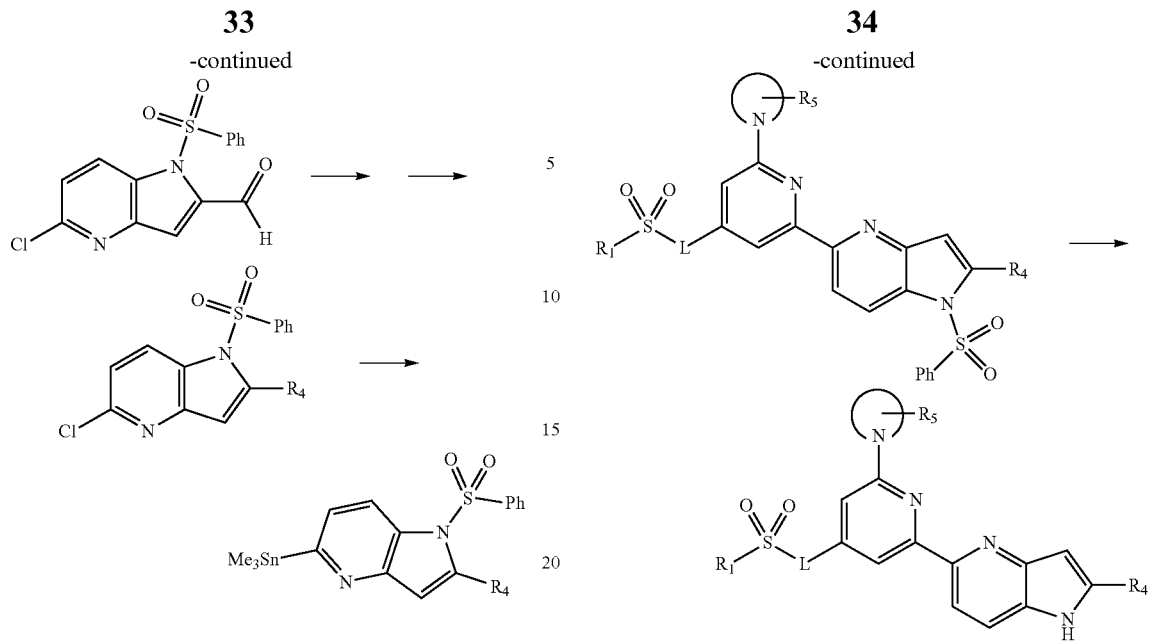

General Scheme

Part a) Sonagashira reaction of a suitably substituted 2-bromopyridine with trimethylsilyl acetylene followed by treatment with base may be used to prepare the 4-aza-indole. Protection of the indazole nitrogen with benzenesulfonamide provides an intermediate suitable for ortho-lithiation with a strong base such as lithium diisopropylamide and treatment with a relevant electrophile to install R1. The trimethylstannane derivative can then be made via metal catalysed cross coupling, for example with hexamethyl distannane.

Part b) The sulfone group may be installed by treating the trichloro intermediate with an appropriate sulfinic acid. Deprotonation and reaction with the relevant alkyl halide followed by installation of the appropriate secondary amine generates the 2-choloropyridyl intermediate Part c) The 2-chloropyridine and 5-trimethyltannyl azaindole may be coupled by palladium catalysis. The example compounds may then be prepared by removal of the protecting groups under standard conditions, for example though the use acidic or alkali conditions.

General Scheme II a)

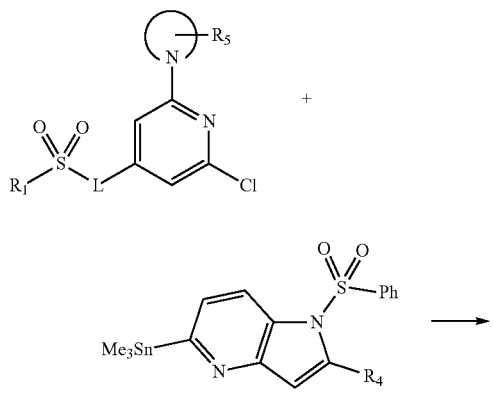

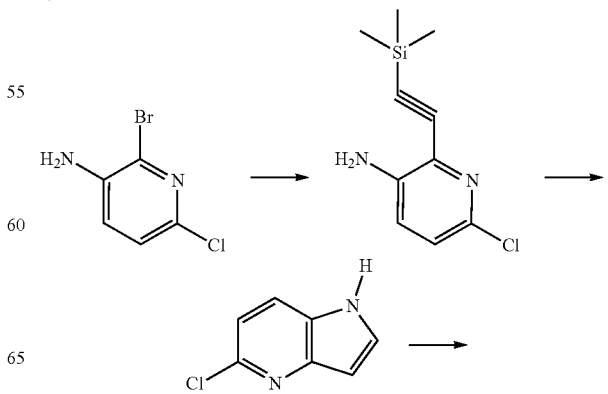

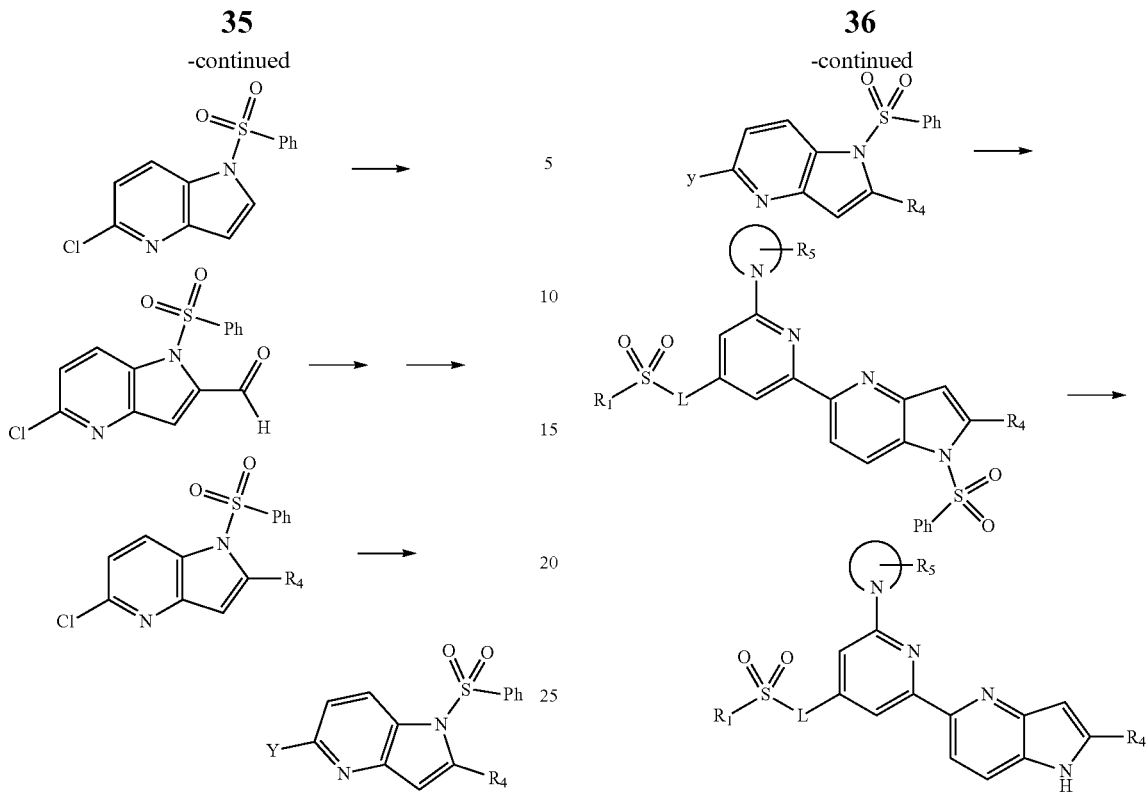

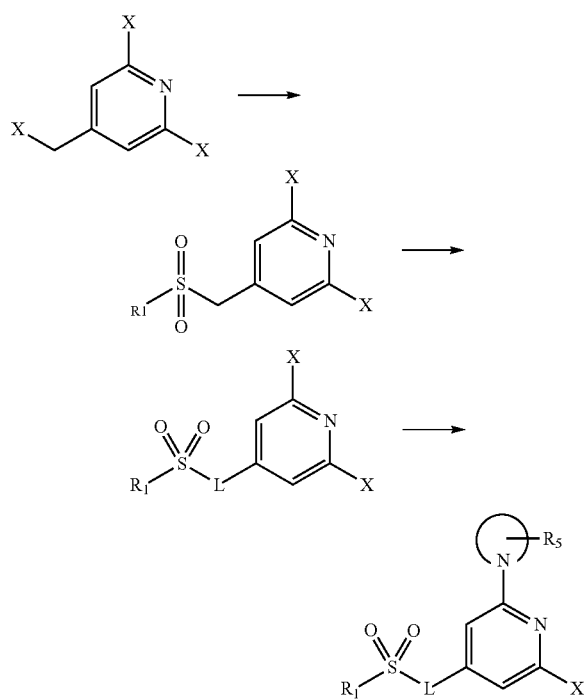

General Scheme II

Part a) Sonagashira reaction of a suitably substituted 2-bromopyridine with trimethylsilyl acetylene followed by treatment with base may be used to prepare the 4-aza-indole. Protection of the indazole nitrogen with benzenesulfonamide provides an intermediate suitable for ortho-lithiation with a strong base such as lithium diisopropylamide and treatment with a relevant electrophile to install R1. Either Y=SnMe$_3$ or SO2$^-$Na$^-$. The trimethylstannane derivative can be made via metal catalysed cross coupling, for example with hexamethyl distannane or the sodium sulfinate can be made by metal catalysed coupling followed by deprotection on treatment with base.

Part b) The sulfone group may be installed by treating the trihalo intermediate with an appropriate sulfinic acid. Deprotonation and reaction with the relevant alkyl halide followed by installation of the appropriate secondary amine generates the 2-halopyridyl intermediate Part c) The 2-halopyridine and 5-trimethyltannyl azaindole may be coupled by palladium catalysis. The example compounds may then be prepared by removal of the protecting groups under standard conditions, for example though the use acidic or alkali conditions.

Route A to Example 1 a)

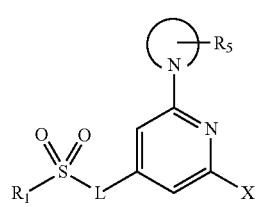

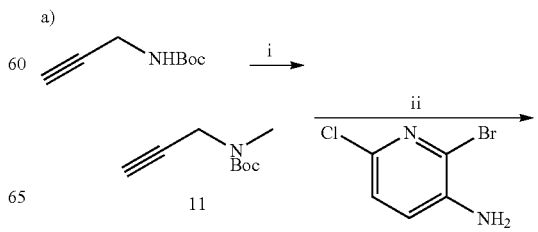

37
-continued
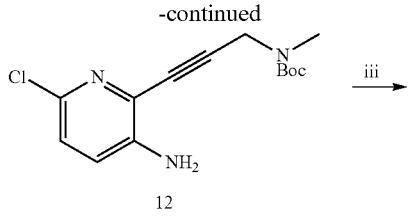
12
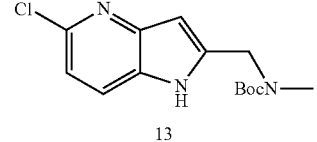
13
b)
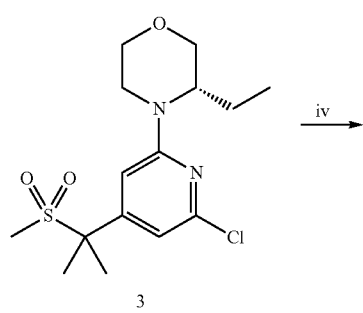
3
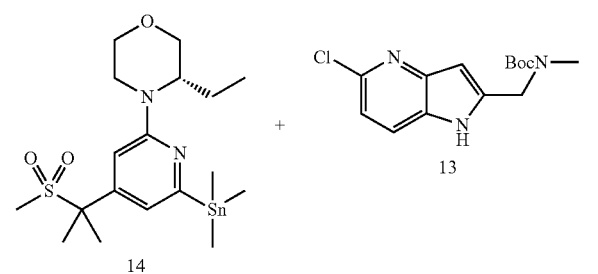
14 + 13
↓ v
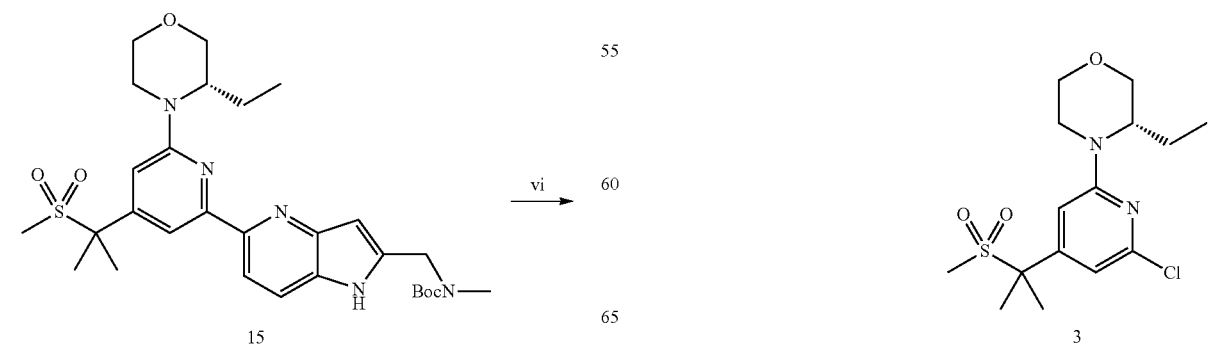
15
38
-continued
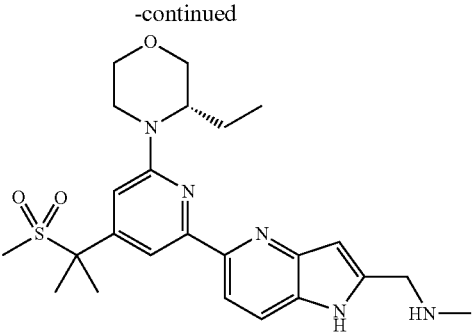
Example 1
i) MeI, NaH, DMF, 0° C. 17 h. ii) PdCl2dppf, CuI, TEA, THF, 70° C. 17 h. iii) KOBut, NMM 21° C. 3 h. iv) PdCl$_2$(dppf) cat., Sn$_2$Me$_6$ (1.8 eq)Toluene 3 h v) PdCl$_2$(dppf) cat., LiCl, Tol, 100° C., 16 h. vi) HCl, dioxane, rt, 5.5 hr
Route B to Example 1
a)
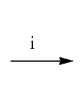
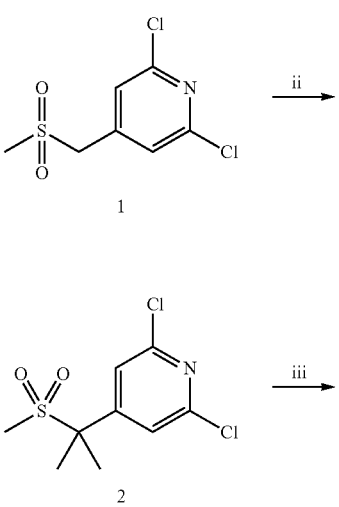
↓ vi
3

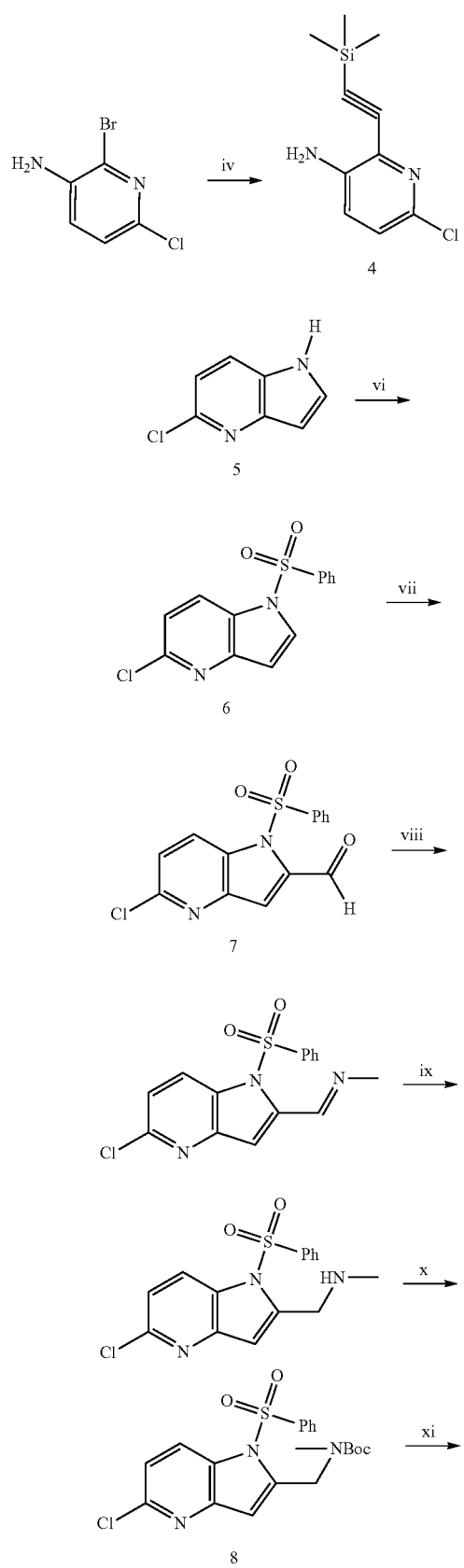
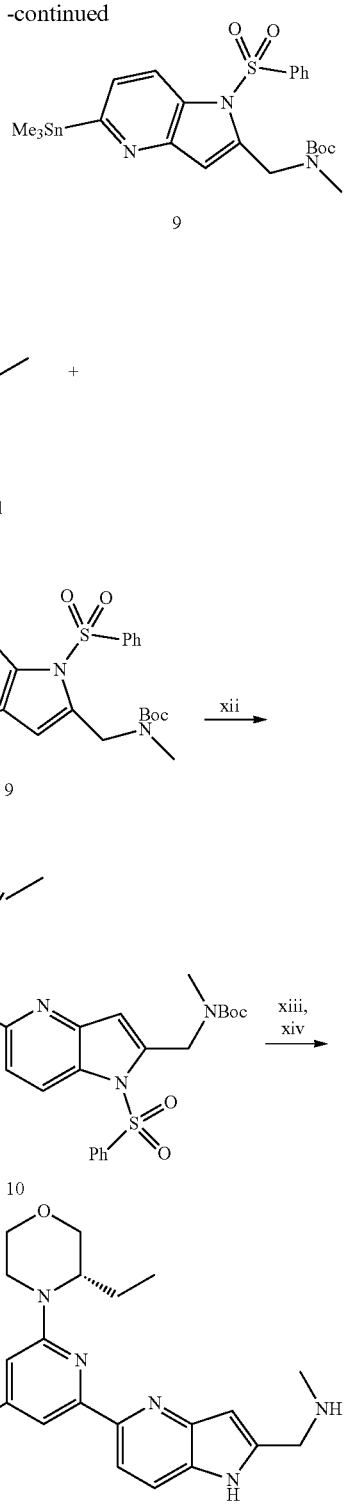

Example 1 i) NaSO₂Me, CH3CN, 85° C., 24 h. ii) NAOtBu(2 eq), MeI(2 eq.), DMF(20 V), 0° C., 1 h. iii) 3-S-ethylmorpholine, DMSO, 130° C., sealed tube, 72 h. iv) ethynyltrimethylsilane, CuI(0.04 eq), TEA(8 eq), Biskis(0.02 eq), 80° C., 1 h. v) KOtBu, NMM, RT, 2 h. vi) PhSO₂Cl (1.3 eq), DMAP (0.1 eq), TEA (1.6 eq), DCM, RT, 2 h. vii) LDA (1.6 eq) -78° C., THF, 1 h DMF (2 eq), -78° C., 40 min, quenched @ -78° C. viii) MeNH₂ (2 eq), AcOH (2 eq), THF 0° C. to RT 1 h. ix) Na(OAc)₃BH (2.5 eq), RT, 18 h. x) NaOH (2M, 3.0 eq), Boc₂O (3.0 eq). xi) Hexamethylditin, PdCl₂(dppf), Tolene, 110° C., MW, 3 h. xii) PdCl2(dppf), LiCl, Toluene, 100° C. 19 h. xiii) methanamine 2M in THF, 2M NaOH, RT 2 h. xiv) 4M HCl in dioxane, RT 1 h.

Route C to Example 22
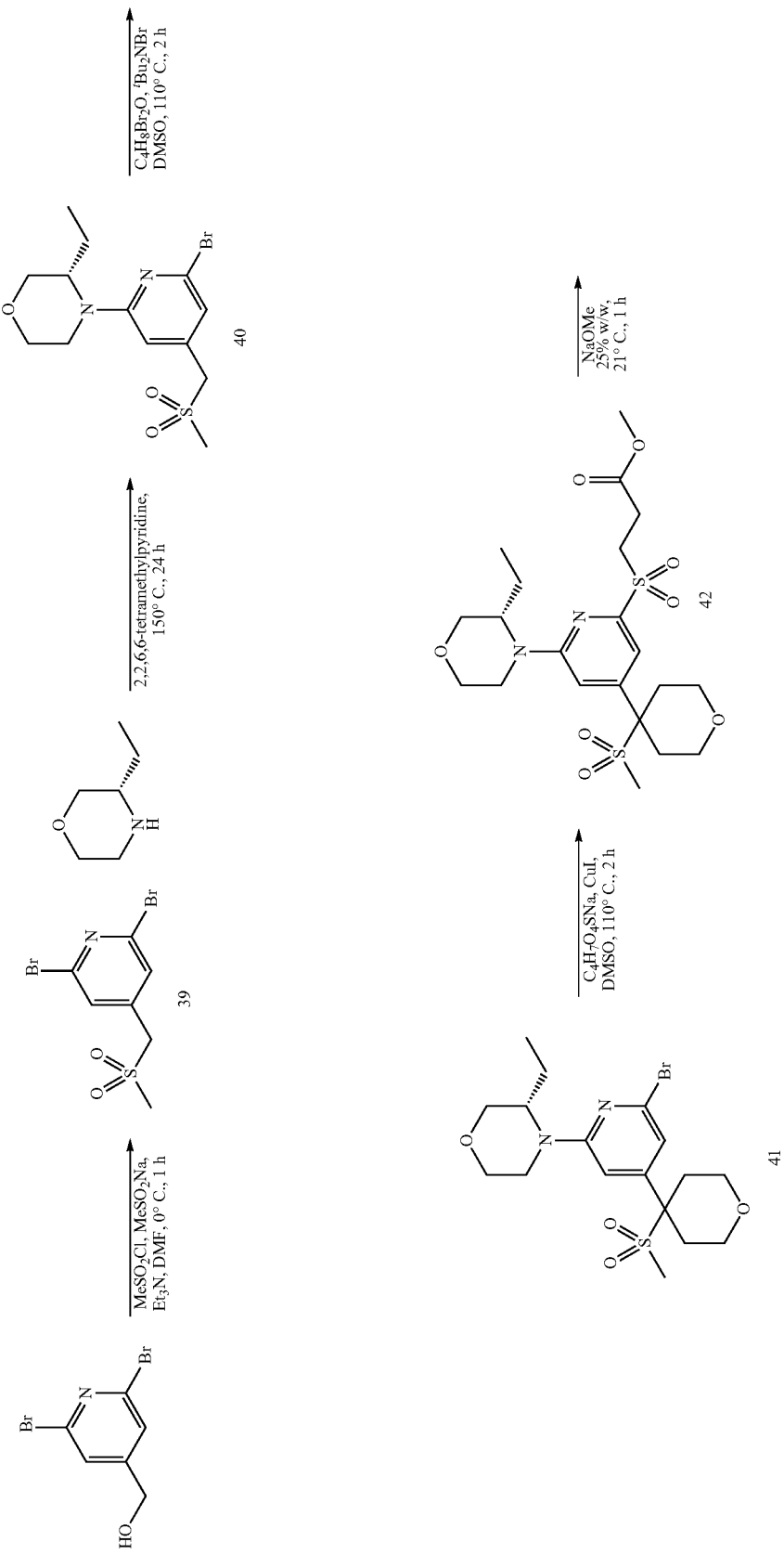

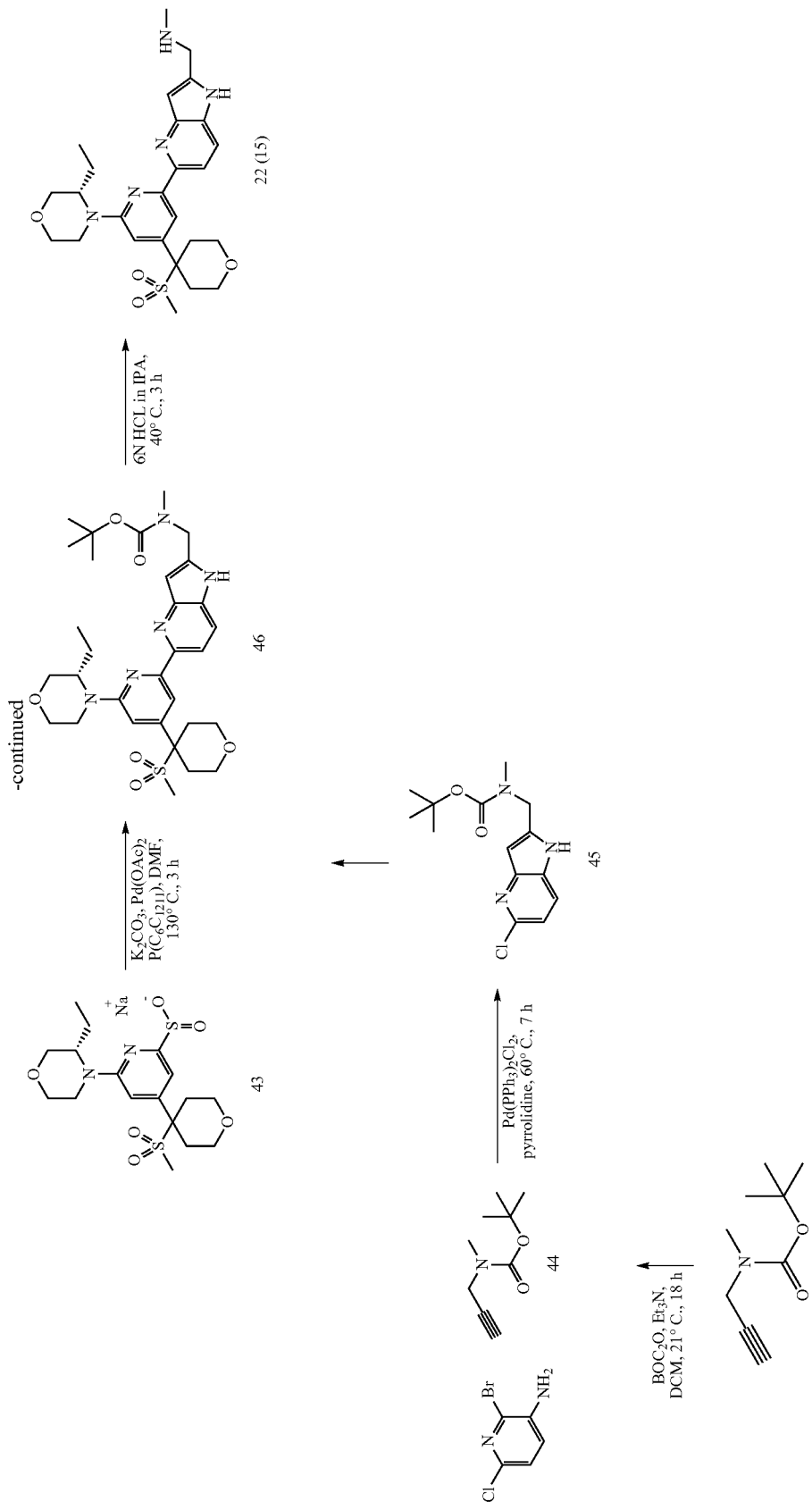

Additional Routes to Intermediates:
General Route to Sulphinate Coupling Partners:
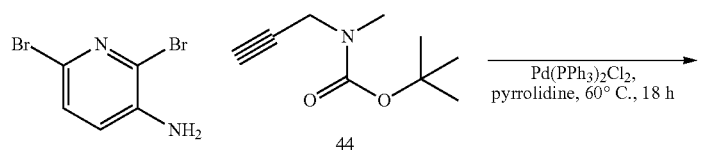
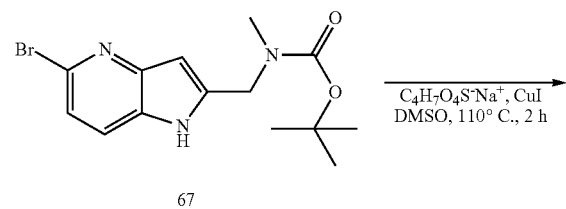
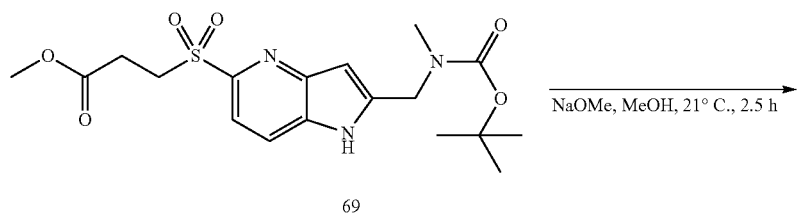
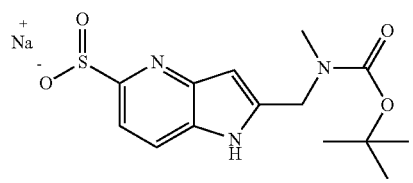
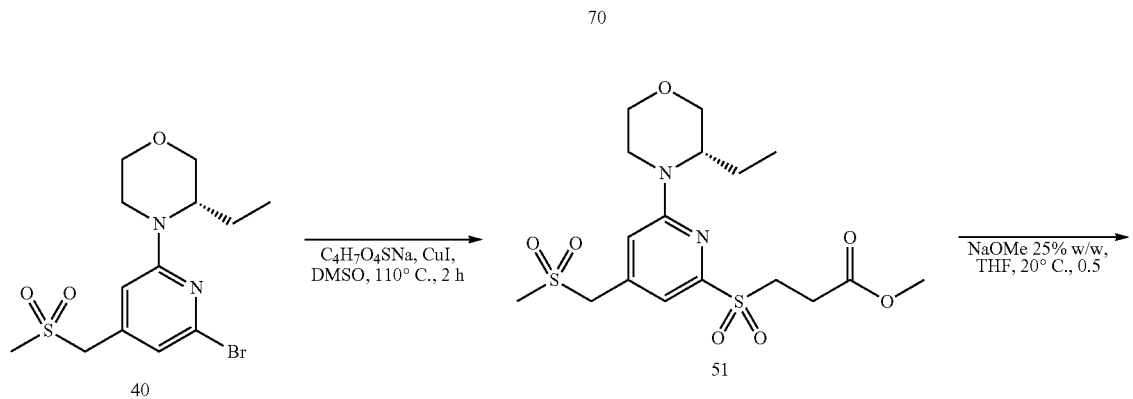
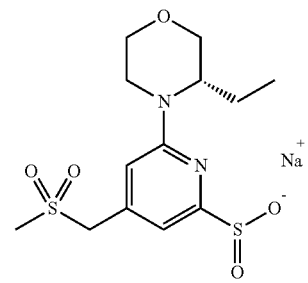

General Route to Sulfonamide Intermediates:

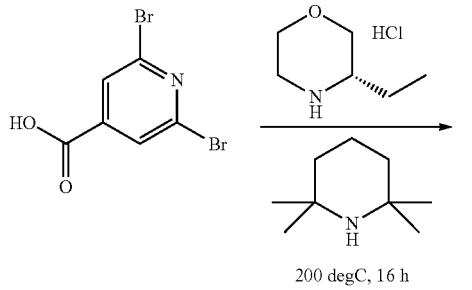

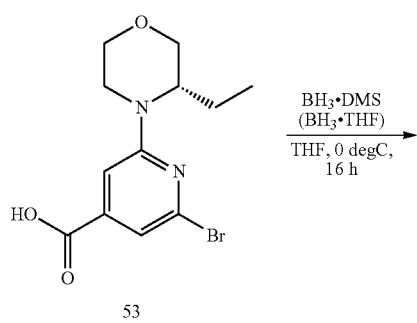

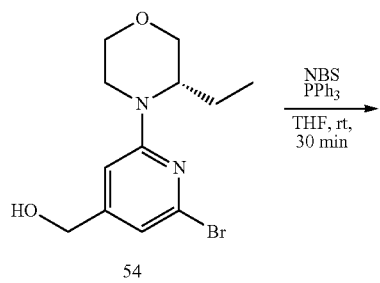

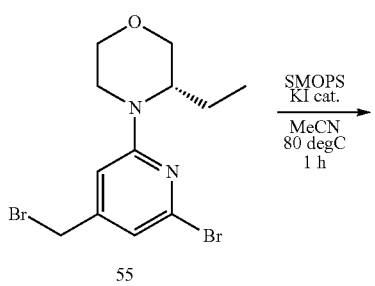

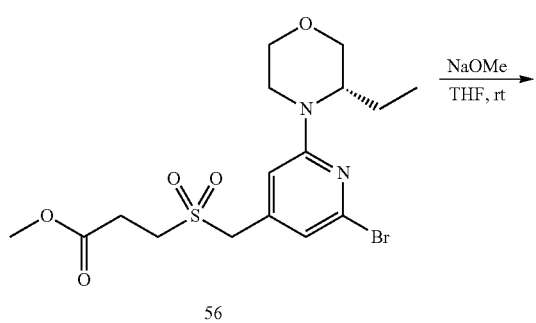

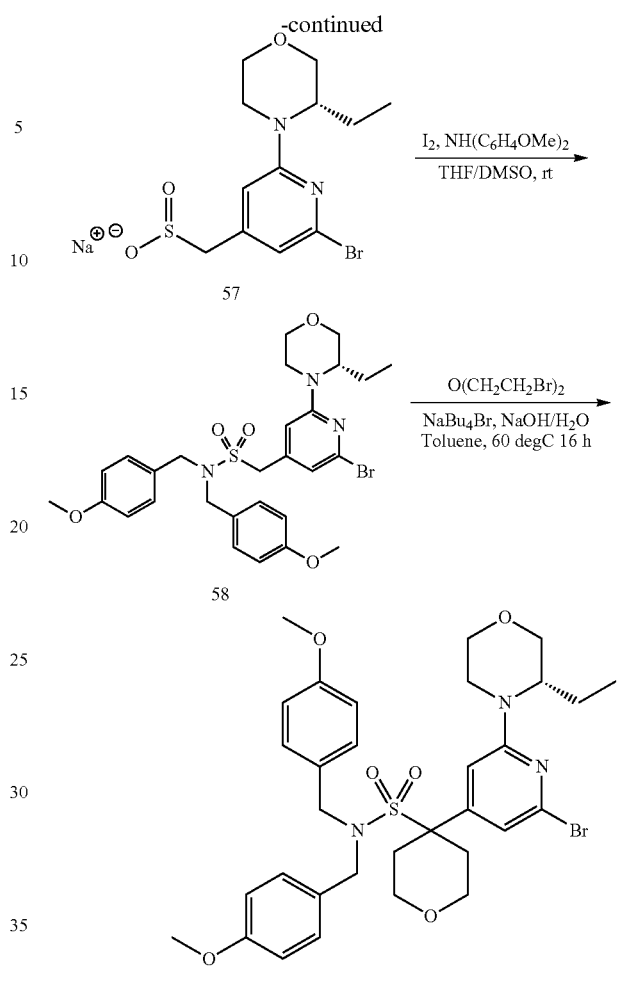

EXAMPLES

Abbreviations

The following list provides definitions of certain abbreviations as used herein. It will be appreciated that the list is not exhaustive, but the meaning of those abbreviations not herein below defined will be readily apparent to those skilled in the art.

Ac (acetyl)
Bu (butyl)
Chiralcel OD-H (cellulose tris(3,5-dimethylphenylcarbamate) coated on 5 μm silica gel)
Chiralpak AD-H (amylose tris(3,5-dimethylphenylcarbamate) coated on 5 μm silica gel)
Chiralpak ID (amylose tris(3-chlorophenylcarbamate) immobilised on 5 μm silica gel)
Chiralpak AS (amylose tris((S)-alpha-methylbenzylcarbamate) coated on 5 μm silica gel)
CSH (Charged Surface Hybrid Technology)
CV (column volume)
DCM (dichloromethane)
DMF (N, N-dimethylformamide)
DMSO (dimethylsulfoxide)
Et (ethyl)
EtOH (ethanol)
EtOAc (ethyl acetate)

h or hr (hour/hours)
MDAP (mass directed auto-preparative HPLC)
Me (methyl)
MeOH (methanol)
$Mg_2SO_4$ (Magnesium Sulphate)
min (minute/minutes)
Pd(dppf)$Cl_2$ (1,1'-[bis(diphenylphosphino)ferrocene]dichloropalladium (II))
Pet Ether (Petroleum Ether)
Ph (phenyl)
$^i$Pr (isopropyl)
room temp (room temperature)
Si (Silica)
SPE (solid phase extraction)
TBME (tert-butyl methyl ether)
TEA (triethylamine)
TFA (trifluoroacetic acid)
THF (tetrahydrofuran)
TLC (thin layer chromatography)
UPLC (Ultra Performance Liquid Chromatography)
References to brine refer to a saturated aqueous solution of sodium chloride.

Experimental Details
Analytical LCMS
Analytical LCMS was conducted on one of the following systems A or B.
The UV detection to all systems was an averaged signal from wavelength of 220 nm to 350 nm and mass spectra were recorded on a mass spectrometer using alternate-scan positive and negative mode electrospray ionization.
LCMS purity is derived from diode array detection.
Experimental details of LCMS systems A-B as referred to herein are as follows:

System A
Column: 50 mm×2.1 mm ID, 1.7 μm Acquity UPLC BEH $C_{18}$ column
Flow Rate: 1 mL/min.
Temp.: 40° C.
Solvents: A: 10 mM ammonium bicarbonate in water adjusted to pH10 with ammonia solution
B: Acetonitrile

| Gradient: | | |
|---|---|---|
| Time (min) | A % | B % |
| 0 | 99 | 1 |
| 1.5 | 3 | 97 |
| 1.9 | 3 | 97 |
| 2.0 | 99 | 1 |

System B
Column: 50 mm×2.1 mm ID, 1.7 μm Acquity UPLC BEH $C_{18}$ column
Flow Rate: 1 mL/min
Temp.: 40° C.
Solvents: A: 0.1% v/v solution of formic acid in water
B: 0.1% v/v solution of formic acid in acetonitrile

| Gradient: | | |
|---|---|---|
| Time (min) | A % | B % |
| 0 | 97 | 3 |
| 1.5 | 0 | 100 |
| 1.9 | 0 | 100 |
| 2.0 | 97 | 3 |

Mass Directed Auto-Preparative HPLC
Crude products were purified by MDAP HPLC by one of the following methods. The run time was 15 min unless otherwise stated. The UV detection for all methods was an averaged signal from wavelength of 210 nm to 350 nm and mass spectra were recorded on a mass spectrometer using alternate-scan positive and negative mode electrospray ionization.

Method HPH_Meth_B:
Method HPH_Meth_B was conducted on an XBridge $C_{18}$ column (typically 100 mm×30 mm i.d. 5 μm packing diameter) at ambient temperature. The solvents employed were:
A=10 mM aqueous ammonium bicarbonate adjusted to pH 10 with ammonia solution.
B=acetonitrile.
The gradient employed was:

| Time (min) | Flow Rate (mL/min) | % A | % B |
|---|---|---|---|
| 0 | 40 | 85 | 15 |
| 1 | 40 | 85 | 15 |
| 20 | 40 | 45 | 55 |
| 21 | 40 | 1 | 99 |
| 25 | 40 | 1 | 99 |

Method HPH_Meth_C:
Method HPH_Meth_C was conducted on an XBridge $C_{18}$ column (typically 100 mm×30 mm i.d. 5 μm packing diameter) at ambient temperature. The solvents employed were:
A=10 mM aqueous ammonium bicarbonate adjusted to pH 10 with ammonia solution.
B=acetonitrile.
The gradient employed was:

| Time (min) | Flow Rate (mL/min) | % A | % B |
|---|---|---|---|
| 0 | 40 | 70 | 30 |
| 1 | 40 | 70 | 30 |
| 10 | 40 | 15 | 85 |
| 11 | 40 | 1 | 99 |
| 15 | 40 | 1 | 99 |

Method HPH_Meth_EXT_C:
Method EXT_C was conducted on an XBridge $C_{18}$ column (typically 100 mm×30 mm i.d. 5 μm packing diameter) at ambient temperature. The solvents employed were:
A=10 mM aqueous ammonium bicarbonate adjusted to pH 10 with ammonia solution.
B=acetonitrile.
The gradient employed was:

| Time (min) | Flow Rate (mL/min) | % A | % B |
|---|---|---|---|
| 0 | 40 | 70 | 30 |
| 1 | 40 | 70 | 30 |
| 20 | 40 | 15 | 85 |

| Time (min) | Flow Rate (mL/min) | % A | % B |
| --- | --- | --- | --- |
| 20.5 | 40 | 1 | 99 |
| 25 | 40 | 1 | 99 |

INTERMEDIATES

Intermediate 1: 2,6-dichloro-4-((methylsulfonyl)methyl)pyridine

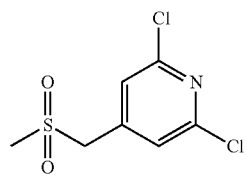

2,6-dichloro-4-((methylsulfonyl)methyl)pyridine

A solution of 2,6-dichloro-4-(chloromethyl)pyridine (1.076 g, 5.48 mmol, Apollo Scientific Limited), sodium methanesulfinate (0.841 g, 8.24 mmol, Aldrich) and potassium iodide (0.185 g, 1.114 mmol, Sigma Aldrich) in Acetonitrile (25 ml) was heated to reflux for 1.5 hours. The mixture was cooled and poured onto water (30 mL). The resulting mixture was extracted with DCM (3×30 mL). The combined organic layers were dried over, $Mg_2SO_4$, then passed through a hydrophobic frit. The volatiles were removed under reduced pressure and dried to give product 2,6-dichloro-4-((methylsulfonyl)methyl)pyridine, (1.236 mg) as a beige powder.

Compound was transferred into a vial using DCM (RA 03), concentrated under a stream of nitrogen in a blowdown unit and dried under vacuum to 2,6-dichloro-4-((methylsulfonyl)methyl)pyridine (1.231 g, 4.87 mmol, 89% yield) as a beige solid. $^1$H NMR (400 MHz, DMSO-d6) d ppm 3.01 (s, 3H) 4.64 (s, 2H) 7.60 (s, 2H). LCMS (System B, UV, ESI): $R_t$=0.75 min, [M+H]$^+$ 240

Intermediate 2: 2,6-dichloro-4-(2-(methylsulfonyl)propan-2-yl)pyridine

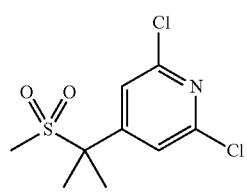

A stirring solution of 2,6-dichloro-4-((methylsulfonyl)methyl)pyridine (the compound of Intermediate 1, 1.2 g, 5.00 mmol) in Tetrahydrofuran (THF) (10 mL) was placed under Nitrogen and cooled to 0° C. Sodium tert-butoxide (2 M in THF) (6.25 mL, 12.49 mmol, Aldrich) was added dropwise and the resulting solution stirred at 0° C. for 2 min. To the solution was added iodomethane (0.625 mL, 10.00 mmol, Aldrich) dropwise over 5 min and the reaction mixture stirred at 0° C. for 2 hr. The reaction mixture was quenched by slow addition of saturated aqueous ammonium chloride solution (7 mL) and the product extracted with EtOAc (2×40 mL). The combined organics were washed with brine (40 mL), dried through a hydrophobic frit and concentrated in vacuo to give 2,6-dichloro-4-(2-(methylsulfonyl)propan-2-yl)pyridine (1.304 g, 4.86 mmol, 97% yield) as a yellow solid. $^1$H NMR (400 MHz, DMSO-d6) δ ppm 1.84 (s, 6H) 2.70 (s, 3H) 7.52 (s, 2H). LCMS (System B, UV, ESI): $R_t$=0.86 min, [M+H]$^+$ 268

Intermediate 3: (S)-4-(6-chloro-4-(2-(methylsulfonyl)propan-2-yl)pyridin-2-yl)-3-ethylmorpholine

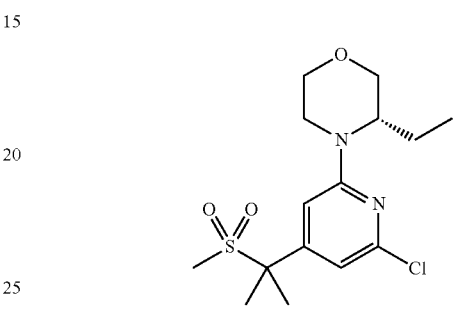

To 2,6-dichloro-4-(2-(methylsulfonyl)propan-2-yl)pyridine (the compound of Intermediate 2, 1.23 g, 4.27 mmol), (S)-3-ethylmorpholine hydrochloride (0.776 g, 5.12 mmol, Ark Pharm), and DIPEA (2.2 ml, 12.60 mmol, Fluorochem) was added anhydrous Dimethyl Sulfoxide (DMSO) (3 ml). The sealed vial was heated and the reaction mixture stirred at 160° C. for 19 hr. The reaction mixture was diluted with ethyl acetate (150 mL) and washed with water (2×50 mL) then brine (50 mL). The organic layer was passed through a hydrophobic frit and concentrated in vacuo. The residue was preabsorbed onto Florisil and purified by flash chromatography (silica, 120 g), eluting with 0-70% ethyl acetate in cyclohexane over 16CV. Appropriate fractions were combined, concentrated in vacuo to give (S)-4-(6-chloro-4-(2-(methylsulfonyl)propan-2-yl)pyridin-2-yl)-3-ethylmorpholine (780 mg, 2.024 mmol, 47.4% yield) as a orange oil. $^1$H NMR (400 MHz, CHLOROFORM-d) δ ppm 0.95 (t, J=7.46 Hz, 3H) 1.28 (t, J=7.21 Hz, 1H) 1.58 (br. s., 1H) 1.67 (dt, J=13.82, 6.79 Hz, 1H) 1.79 (s, 6H) 1.83-1.98 (m, 2H) 2.06 (s, 1H) 3.23 (td, J=12.72, 3.67 Hz, 1H) 3.52-3.70 (m, 2H) 3.90-4.05 (m, 4H) 4.14 (q, J=7.09 Hz, 1H) 6.75 (d, J=3.67 Hz, 2H). LCMS (System B, UV, ESI): $R_t$=1.08 min, [M+H]$^+$ 347

Intermediate 4: 6-chloro-2-((trimethylsilyl)ethynyl)pyridin-3-amine

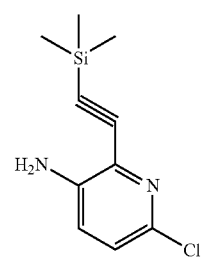

A solution of 2-bromo-6-chloropyridin-3-amine (10 g, 48.2 mmol, Combi Blocks), copper(I) iodide (0.367 g, 1.928 mmol, Loba Chem) and triethylamine (55.8 mL, 400 mmol, RCP) in N,Ndimethylformamide (DMF) (100 mL) stirred under nitrogen at 20° C. was degassed with argon for 30 mins prior to the addition of bis(triphenylphosphine)palladium(II) chloride (0.677 g, 0.964 mmol, Alfa), and ethynyltrimethylsilane (14.20 g, 145 mmol, Avra). The reaction mixture was stirred at 80° C. for 1 hour. The mixture was diluted with water and extracted with EtOAc (2×300 mL). The combined organic layers were washed with brine (500 mL) and dried over anhydrous sodium sulfate. The organic phase was filtered and concentrated in vacuo to afford crude product.

The crude product was pre absorbed on silica gel, and purified by normal phase column chromatography through silica gel. The product was eluted with 20% ethyl acetate in petroleum ether, the corresponding pure fractions were concentrated in vacuo to give 6-chloro-2((trimethylsilyl) ethynyl)pyridin-3-amine (5 g, 20.93 mmol, 43.4% yield) as yellow solid. $^1$H NMR (400 MHz, DMSO-$d_6$) δ ppm 0.26 (s, 9H) 5.66 (s, 2H) 7.16 (s, 2H). $R_t$=2.58 min, [M+H]$^+$ 225 [Acq. Method Conditions: RND-FA-4-MIN Column: Acquity BEH C18 (50 mm×2.1 mm, 1.7 um)
Mobile Phase: A: 0.1% Formic Acid in ACN
B: 0.1% Formic Acid in water;
Time (min)/% B: 0/97, 0.4/97, 2.5/2, 3.4/2, 3.5/97, 4.0/97
Column Temp: 35° C., Flow Rate: 0.6 mL/min]

Intermediate 5: 5-chloro-1H-pyrrolo[3,2-b]pyridine

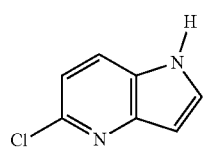

To a stirred solution of potassium tert-butoxide (4.47 g, 39.8 mmol, Avra) in N-methylmorpholine (25 mL, Aldrich) H) at RT, was added 6-chloro-2-((trimethylsilyl)ethynyl) pyridin-3-amine (the compound of intermediate 4, 7 g, 31.1 mmol) in N-methylmorpholine (25 mL). The reaction mixture was stirred at RT for 3 hr.

The reaction mixture was diluted with water (200 mL) and extracted with EtOAc (2×300 mL). The combined organic layers were washed with brine (500 mL) and dried over anhydrous sodium sulfate. The reaction mixture was filtered and concentration in vacuo afforded the crude product.

The crude product was pre absorbed on silica gel, and purified by normal phase column chromatography through silica gel. The desired product was eluted with 20% ethyl acetate in petroleum ether, and the corresponding pure fractions were concentrated in vacuo to give 5-chloro-1H-pyrrolo[3,2-b]pyridine (3.5 g, 17.94 mmol, 57.6% yield) brown solid. $^1$H NMR (400 MHz, CHLOROFORM-d) δ ppm 6.71 (br. s., 1H) 7.14 (d, J=8.55 Hz, 1H) 7.46 (t, J=2.96 Hz, 1H) 7.64 (d, J=8.55 Hz, 1H). $R_t$=1.74 min, [M+H]$^+$ 153 [Acq. Method Conditions: RND-FA-4-MIN Column: Acquity BEH C18 (50 mm×2.1 mm, 1.7 um)
Mobile Phase: A: 0.1% Formic Acid in ACN
B: 0.1% Formic Acid in water;
Time (min)/% B: 0/97, 0.4/97, 2.5/2, 3.4/2, 3.5/97, 4.0/97
Column Temp: 35° C., Flow Rate: 0.6 mL/min]

Intermediate 6: 5-chloro-1-(phenylsulfonyl)-1H-pyrrolo[3,2-b]pyridine

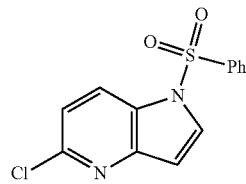 [SMILES: O=S(=O)(c1ccccc1)n1ccc2nc(Cl)ccc21]

To a stirred solution of 5-chloro-1H-pyrrolo[3,2-b]pyridine (the compound of Intermediate 5, 5 g, 28.1 mmol) and DMAP (0.343 g, 2.81 mmol, Avra) in Dichloromethane (DCM) (50 mL) was added benzenesulfonyl chloride (4.71 mL, 36.5 mmol, Avra) and TEA (6.26 mL, 44.9 mmol, Advent). The reaction mixture was stirred under nitrogen at room temperature for 3 hours.

After completion of reaction mixture was diluted with water (200 ml), extracted with DCM (250 ml×2). The combined organic layers were concentrated to afford brown gummy compound. The crude product was pre absorbed with silica gel, and purified by normal phase column chromatography through silica gel. The desired product was eluted with 30% EtOAc in pet ether, collected corresponding pure fractions were concentrated in vacuo to give 5-chloro-1-(phenylsulfonyl)-1H-pyrrolo[3,2-b]pyridine (5 g, 16.47 mmol, 58.6% yield) as yellow solid. $^1$H NMR (400 MHz, CHLOROFORM-d) δ ppm 6.81 (d, J=3.73 Hz, 1H) 7.23-7.28 (m, 1H) 7.45-7.52 (m, 2H) 7.55-7.63 (m, 1H) 7.80 (d, J=3.73 Hz, 1H) 7.84-7.91 (m, 2H) 8.22 (d, J=8.55 Hz, 1H). $R_t$=2.48 min, [M+H]$^+$ 293 [Acq. Method Conditions: RND-FA-4-MIN Column: Acquity BEH C18 (50 mm×2.1 mm, 1.7 um)
Mobile Phase: A: 0.1% Formic Acid in ACN
B: 0.1% Formic Acid in water;
Time (min)/% B: 0/97, 0.4/97, 2.5/2, 3.4/2, 3.5/97, 4.0/97
Column Temp: 35° C., Flow Rate: 0.6 mL/min]

Intermediate 7: 5-chloro-1-(phenylsulfonyl)-1H-pyrrolo[3,2-b]pyridine-2-carbaldehyde

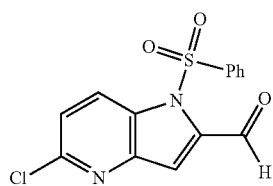 [SMILES: O=Cc1cc2nc(Cl)ccc2n1S(=O)(=O)c1ccccc1]

A solution of LDA (2M in THF) (13.17 mL, 26.3 mmol, Hychem) was added dropwise to a solution of 5-chloro-1-(phenylsulfonyl)-1H-pyrrolo[3,2-b]pyridine (the compound of Intermediate 6, 5 g, 16.47 mmol) in Tetrahydrofuran (THF) (50 mL) at −78° C. and the reaction mixture was stirred under argon for 1 hr. N,N-dimethylformamide (2.55 mL, 32.9 mmol, Chemlabs) was added dropwise to the reaction mixture at −78° C. and the reaction mixture was stirred at −78° C. for 40 min.

The reaction mixture was quenched with saturated aq ammonium chloride (100 mL) whilst maintaining the temperature at -78° C. The reaction mixture was allowed to room temperature and diluted with water (150 mL) and extracted with EtOAc (2×250 mL). The combined organic layer was washed with brine solution (300 mL), dried over anhydrous sodium sulfate, filtered and concentrated in vacuo to afford crude product.

The crude product was diluted with DCM (100 mL) and was pre-adsorbed on to silicagel and purified by normal phase chromatography. The product was eluted with 30% EtOAc in petroleum ether. Collected fractions were concentrated in vacuo to afford 5-chloro-1-(phenylsulfonyl)-1H-pyrrolo[3,2-b]pyridine-2-carbaldehyde (4 g, 9.63 mmol, 58.5% yield) as pale yellow solid. $^1$H NMR (400 MHz, DMSO-$d_6$) δ ppm 6.50 (br. s., 1H) 7.41 (d, J=8.77 Hz, 1H) 7.59-7.67 (m, 2H) 7.73-7.80 (m, 1H) 7.95 (br. s., 2H) 8.43 (d, J=8.11 Hz, 1H). $R_t$=2.50 min, [M+H]$^+$ 321 [Acq. Method Conditions: RND-FA-4-MIN Column: Acquity BEH C18 (50 mm×2.1 mm, 1.7 um)
Mobile Phase: A: 0.1% Formic Acid in ACN
B: 0.1% Formic Acid in water;
Time (min)/% B: 0/97, 0.4/97, 2.5/2, 3.4/2, 3.5/97, 4.0/97
Column Temp: 35° C., Flow Rate: 0.6 mL/min]

Intermediate 8: tert-butyl ((5-chloro-1-(phenylsulfonyl)-1H-pyrrolo[3,2-b]pyridin-2-yl)methyl)(methyl) carbamate

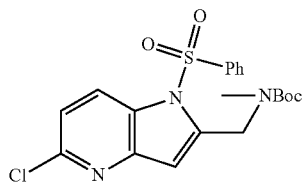 [SMILES: CN(Cc1cc2nc(Cl)ccc2n1S(=O)(=O)c1ccccc1)C(=O)OC(C)(C)C]

A solution of 5-chloro-1-(phenylsulfonyl)-1H-pyrrolo[3,2-b]pyridine-2-carbaldehyde (the compound of Intermediate 7, 4 g, 9.63 mmol) in Tetrahydrofuran (THF) (40 mL) was treated with a solution of methanamine (9.63 mL, 19.27 mmol, Hychem) in acetic acid (1.103 mL, 19.27 mmol, Chemtabs) and the reaction mixture was stirred under nitrogen at room temp for 2.5 h. Additional methanamine (9.63 mL, 19.27 mmol) was added and the reaction mixture was stirred at RT for a further 2.5 hrs. Sodium triacetoxyborohydride (4.08 g, 19.27 mmol) was added and the reaction mixture stirred at RT for 15 hrs. 0.5 M sodium hydroxide (60 mL, 30.0 mmol) was added and resulting mixture was stirred at RT for 7 hrs. Boc-anhydride (5.26 mL, 22.64 mmol) was added and the reaction mixture stirred for 2 hrs.

The mixture was diluted with water (150 mL) and extracted with DCM (2×200 ml). The combined organic layers were dried over anhydrous sodium sulfate, filtered and concentrated in vacuo to afford crude product.

The crude was purified by normal phase column chromatography eluting with 10-15% EtOAc:hexane to afford tert-butyl ((5-chloro-1-(phenylsulfonyl)-1H-pyrrolo[3,2-b]pyridin-2-yl)methyl)(methyl)carbamate (1.7 g, 3.24 mmol, 33.6% yield) as off-white solid. $^1$H NMR (400 MHz, DMSO-$d_6$) δ ppm 2.91 (s, 3H) 4.82 (s, 2H) 6.50 (br. s., 1H) 7.41 (d, J=8.77 Hz, 1H) 7.60-7.68 (m, 2H) 7.71-7.82 (m, 1H) 7.95 (br. s., 2H) 8.43 (d, J=8.11 Hz, 1H). $R_t$=2.79 min, [M+H]$^+$ 436 [Acq. Method Conditions: RND-FA-4-MIN Column: Acquity BEH C18 (50 mm×2.1 mm, 1.7 um)
Mobile Phase: A: 0.1% Formic Acid in ACN
B: 0.1% Formic Acid in water;
Time (min)/% B: 0/97, 0.4/97, 2.5/2, 3.4/2, 3.5/97, 4.0/97
Column Temp: 35° C., Flow Rate: 0.6 mL/min]

Intermediate 9: tert-butyl methyl((1-(phenylsulfonyl-5-(trimethylstannyl)-1H-pyrrolo[3,2-b]pyridin-2-yl)methyl)carbamate

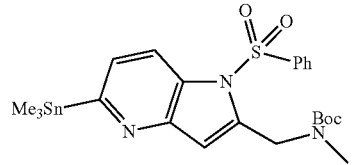

tert-butyl ((5-chloro-1-(phenylsulfonyl)-1H-pyrrolo[3,2-b]pyridin-2-yl)methyl)(methyl)carbamate (the compound of Intermediate 8, 1 g, 2.294 mmol), PdCl2(dppf) (0.084 g, 0.115 mmol, Manchester Organics) and 1,1,1,2,2,2-hexamethyldistannane (0.85 mL, 4.10 mmol, Sigma Aldrich) were dissolved in Toluene (8 mL) and the resulting mixture was degassed under a flow of nitrogen, and heated to 110° C. for 2 h. The reaction mixture was allowed to cool and purified by flash chromatography (KPNH, 110 g), eluting with, cyclohexane (200 mL), 1:1 TBME:cyclohexane (500 mL) and 2:1 TBME:cyclohexane (200 mL). Appropriate fractions were combined, concentrated in vacuo and under nitrogen to give tert-butyl methyl((1-(phenylsulfonyl)-5-(trimethylstannyl)-1H-pyrrolo[3,2-b]pyridin-2-yl)methyl) carbamate (1.188 g, 1.832 mmol, 80% yield) as an off-white solid. $^1$H NMR (400 MHz, CHLOROFORM-d) δ ppm 0.24-0.49 (m, 9H) 1.32-1.64 (m, 9H) 2.92-3.03 (m, 3H) 4.80-4.98 (m, 2H) 6.71 (s, 1H) 7.36 (br.s., 1H) 7.41-7.52 (m, 2H) 7.54-7.62 (m, 1H) 7.81 (d, J=12.96 Hz, 2H) 8.24 (br. s., 1H). LCMS (System B, UV, ESI): $R_t$=1.00 min, [M+H]$^+$ 566

Intermediate 10: tert-butyl (S)-((5-(6-(3-ethylmorpholino)-4-(2-(methylsulfonyl)propan-2-yl)pyridin-2-yl)-1-(phenylsulfonyl)-1H-pyrrolo[3,2-b]pyridin-2-yl)methyl)(methyl)carbamate

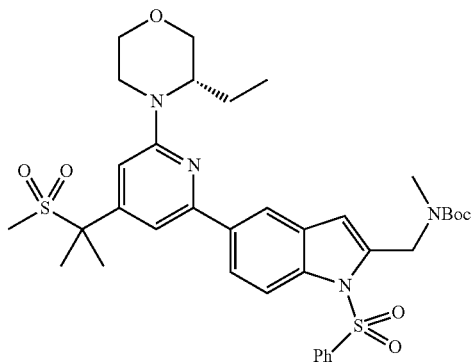

(S)-4-(6-chloro-4-(2-(methylsulfonyl)propan-2-yl)pyridin-2-yl)-3-ethylmorpholine (the compound of Intermediate 3, 630 mg, 1.635 mmol), lithium chloride (71 mg, 1.675 mmol, Aldrich) and PdCl2(dppf) (123 mg, 0.168 mmol, Manchester Organics) were combined in Toluene (15 mL). tert-butyl methyl((1-(phenylsulfonyl)-5-(trimethylstannyl)-1H-pyrrolo[3,2-b]pyridin-2-yl)methyl)carbamate (Intermediate 9, 1110 mg, 1.711 mmol) was added, the mixture degassed under a flow of nitrogen and heated at 100° C. for 15 hr. Further PdCl2(dppf) (123 mg, 0.168 mmol) and lithium chloride (71 mg, 1.675 mmol) were added, the mixture degassed under a flow of nitrogen and heated at 100 C for 4 hr.

The residue was filtered through Celite (10 g), eluting with ethyl acetate (2×30 mL). The filtrate was washed with 1 M KF solution (2×60 mL), brine (60 mL), dried through a hydrophobic frit and concentrated under nitrogen. The mixture was preabsorbed onto Florisil and purified by normal phase chromatography (silica, 120 g), eluting 0-70% ethyl acetate in cyclohexane over 16 CV followed by holding at 70% ethyl acetate in cyclohexane for 1 CV followed by 70-100% ethyl acetate in cyclohexane over 3 CV followed by holding at 100% ethyl acetate for 3 CV. Appropriate fractions were combined and concentrated in vacuo to give tert-butyl (S)-((5-(6-(3-ethylmorpholino)-4-(2-(methylsulfonyl)propan-2-yl)pyridin-2-yl)-1-(phenylsulfonyl)-1H-pyrrolo[3,2-b]pyridin-2-yl)methyl)(methyl)carbamate (790 mg, 0.910 mmol, 55.7% yield) as a brown solid. $^1$H NMR (400 MHz, CHLOROFORM-d) δ ppm 1.00 (t, J=7.46 Hz, 3H) 1.36-1.62 (m, 9H) 1.63-1.76 (m, 1H) 1.85-2.02 (m, 7H) 2.65 (s, 3H) 2.93-3.07 (m, 3H) 3.33 (td, J=12.59, 3.67 Hz, 1H) 3.61-3.79 (m, 2H) 3.93-4.10 (m, 3H) 4.79-5.02 (m, 2H) 6.76 (br.s., 1H) 7.00 (s, 1H) 7.48 (br.s., 3H) 7.55-7.66 (m, 1H) 7.81 (br. s., 2H) 8.02 (br. s., 1H) 8.36 (d, J=8.56 Hz, 1H) 8.51 (d, J=5.14 Hz, 1H). LCMS (System B, UV, ESI): R$_t$=1.45 min, [M+H]$^+$ 712

Intermediate 11: tert-butyl methyl(prop-2-yn-1-yl)carbamate

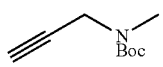

To tert-butyl prop-2-yn-1-ylcarbamate (1 g, 6.44 mmol, Sigma Aldrich) in anhydrous N,N-Dimethylformamide (DMF) (15 mL) was added NaH (60% dispersion in mineral oil) (0.387 g, 9.67 mmol, Sigma Aldrich) and the mixture stirred at 0° C. for 15 min before adding MeI (0.806 mL, 12.89 mmol, Sigma Aldrich) was added and the resulting mixture stirred at 0 C for 16 hr. The reaction mixture was diluted with water [cautiously] (40 mL) and EtOAC (40 mL), the aqueous extracted with ethyl acetate (40 mL), the combined organics washed with saturated aqueous sodium bicarbonate solution (40 mL) filtered through a hydrophobic frit and concentrated in vacuo to give tert-butyl methyl (prop-2-yn-1-yl)carbamate (1.033 g, 5.49 mmol, 85% yield) as a yellow oil. 1H NMR (400 MHz, CHLOROFORM-d) δ ppm 1.46 (s, 9H), 2.14-2.28 (m, 1H), 2.90 (d, J=1.5 Hz, 2H), 4.03 (br s, 2H). LCMS No chromophore Intermediate 12: tert-butyl (3-(3-amino-6-chloropyridin-2-yl)prop-2-yn-1-yl)(methyl)carbamate

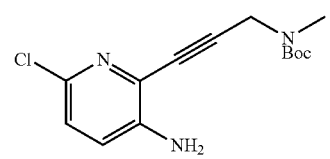 [SMILES: CN(CC#Cc1nc(Cl)ccc1N)C(=O)OC(C)(C)C]

A mixture of tert-butyl methyl(prop-2-yn-1-yl)carbamate (612 mg, 3.62 mmol, Intermediate 11), 2-bromo-6-chloropyridin-3-amine (500 mg, 2.410 mmol, Fluorochem), copper I iodide (51 mg, 0.268 mmol, Sigma), PdCl2(dppf) (148 mg, 0.202 mmol, Manchester Organics) and TEA (0.504 mL, 3.62 mmol, Sigma) in a sealed vial was degassed (purged and filled with nitrogen×3) before adding anhydrous Tetrahydrofuran (THF) (10 mL). The suspension was degassed by bubbling nitrogen through for 2 min. The reaction mixture was heated to 70° C. for 17 hr. The reaction mixture was filtered through a 2.5 g Celite SPE, eluting with ethyl acetate (30 mL) and water (10 mL). The reaction mixture was diluted with water (20 mL), the aqueous extracted with ethyl acetate (3×30 mL), combined organics washed with brine (20 mL), dried through a hydrophobic frit and concentrated in vacuo and under nitrogen to give tert-butyl (3-(3-amino-6-chloropyridin-2-yl)prop-2-yn-1-yl)(methyl)carbamate (1.074 g, 2.360 mmol, 98% yield) as a brown oil. $^1$H NMR (400 MHz, CHLOROFORM-d) δ ppm 1.45-1.56 (m, 12H) 3.00 (s, 3H) 4.34 (s, 2H) 6.96-7.13 (m, 2H). LCMS (System B, UV, ESI) R$_t$=1.08 min, [M+H]+ 240, 242

Intermediate 13: tert-butyl ((5-chloro-1H-pyrrolo[3,2-b]pyridin-2-yl)methyl)(methyl)carbamate

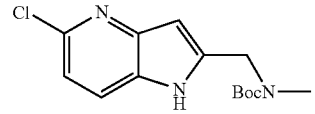 [SMILES: CN(Cc1cc2nc(Cl)ccc2[nH]1)C(=O)OC(C)(C)C]

KOtBu (0.344 g, 3.07 mmol, Sigma Aldrich) was added to tert-butyl (3-(3-amino-6-chloropyridin-2-yl)prop-2-yn-1-yl)(methyl)carbamate (1.0741 g, 2.361 mmol, the compound of Intermediate 12) and the mixture degassed (purge/fill with nitrogen×3) followed by adding 4-methylmorpholine (5.0 ml, 45.5 mmol, Sigma Aldrich). The mixture was sonicated before stirring at 21° C. for 3 hr. Reaction mixture was partitioned between ethyl acetate (30 mL) and water (30 mL), the aqueous extracted with ethyl acetate (20 mL×3), combined organics washed with brine (40 mL), dried through a hydrophobic frit and concentrated in vacuo and under nitrogen. Crude was dry loaded on fluorisil and purified by flash chromatography, eluting with 0-100% ethyl acetate in cyclohexane. Appropriate fractions were combined, concentrated in vacuo to give tert-butyl ((5-chloro-1H-pyrrolo[3,2-b]pyridin-2-yl)methyl)(methyl)carbamate (526 mg, 1.672 mmol, 70.8% yield) as a brown solid. 1H NMR (400 MHz, CHLOROFORM-d) δ ppm 1.51 (s, 9H), 2.91 (s, 3H), 4.46 (br s, 2H), 6.51 (d, J=1.5 Hz, 1H), 7.09 (d, J=8.3 Hz, 1H), 7.57 (dd, J=8.4, 0.9 Hz, 1H), 9.30 (br s, 1H). LCMS (System B, UV, ESI): Rt=1.03 min, [M+H]+ 296, 298.

Intermediate 14: (S)-3-ethyl-4-(4-(2-(methylsulfonyl)propan-2-yl)-6-(trimethylstannyl)pyridin-2-yl)morpholine

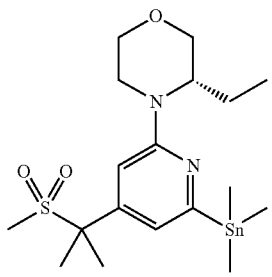

(S)-4-(6-chloro-4-(2-(methylsulfonyl)propan-2-yl)pyridin-2-yl)-3-ethylmorpholine (500 mg, 1.355 mmol, the compound of Intermediate 3), PdCl2(dppf) (59 mg, 0.081 mmol, Sigma Aldrich) and 1,1,1,2,2,2-hexamethyldistannane (0.506 mL, 2.439 mmol, Sigma Aldrich) were dissolved in Toluene (8 mL) and the resulting mixture was degassed under a flow of nitrogen, and heated to 110° C. for 4 hr.

The reaction mixture was allowed to cool and purified by flash chromatography (KPNH, 55 g), eluting with, cyclohexane (200 mL), 1:1 TBME:cyclohexane (500 mL) and 100% TBME:cyclohexane (300 mL). Appropriate fractions were combined, concentrated in vacuo and under nitrogen to give (S)-3-ethyl-4-(4-(2-(methylsulfonyl)propan-2-yl)-6-(trimethylstannyl)pyridin-2-yl)morpholine (0.5004 g, 0.990 mmol, 73.0% yield) as an off-white solid. ¹H NMR (400 MHz, CHLOROFORM-d) δ ppm 0.32 (s, 9H) 0.95 (t, J=7.46 Hz, 3H) 1.52-1.67 (m, 1H) 1.81 (s, 6H) 1.84-1.97 (m, 1H) 2.60 (s, 3H) 3.21 (td, J=12.53, 3.79 Hz, 1H) 3.59-3.74 (m, 3H) 3.93-4.07 (m, 3H) 4.10-4.21 (m, 1H) 6.71 (d, J=1.22 Hz, 1H) 6.92 (d, J=1.22 Hz, 1H). LCMS (System B, UV, ESI): Rt=0.67 min, [M+H+] 477.

Intermediate 15: tert-butyl (S)-((5-(6-(3-ethylmorpholino)-4-(2-(methylsulfonyl)propan-2-yl)pyridin-2-yl)-1H-pyrrolo[3,2-b]pyridin-2-yl)methyl)(methyl)carbamate

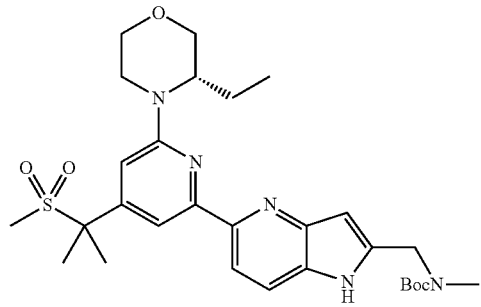

tert-butyl ((5-chloro-1H-pyrrolo[3,2-b]pyridin-2-yl)methyl)(methyl)carbamate (100 mg, 0.318 mmol, Intermediate 13), lithium chloride (14.15 mg, 0.334 mmol, Aldrich) and PdCl2(dppf) (23.26 mg, 0.032 mmol, Manchester Organics) were combined in Toluene (3 mL). (S)-3-ethyl-4-(4-(2-(methylsulfonyl)propan-2-yl)-6-(trimethylstannyl)pyridin-2-yl)morpholine (169 mg, 0.334 mmol, the compound of Intermediate 14) was added, the mixture degassed under a flow of nitrogen and heated at 100° C. for 3 hr. Further PdCl2(dppf) (23.26 mg, 0.032 mmol, Manchester Organics) and lithium chloride (14.15 mg, 0.334 mmol, Aldrich) were added, the reaction mixture degassed by bubbling nitrogen through for 2 min and reheated to 100° C. for total of 23 hr. The residue was filtered through Celite (2.5 g), eluting with ethyl acetate (30 mL). The filtrate was washed with 1 M KF solution (2×40 mL), brine (40 mL), dried through a hydrophobic frit and concentrated under nitrogen. The mixture was preabsorbed onto Florisil and purified by normal phase chromatograph, eluting 0-100% ethyl acetate in cyclohexane over 14 CV separation was not achieved. Appropriate fractions were combined and concentrated in vacuo loaded in DCM and purified by normal phase chromatography, eluting 70-100% ethyl acetate in cyclohexane over 6 CV. Again separation not achieved. Appropriate fractions were combined, concentrated in vacuo to give crude tert-butyl (S)-((5-(6-(3-ethylmorpholino)-4-(2-(methylsulfonyl)propan-2-yl)pyridin-2-yl)-1H-pyrrolo[3,2-b]pyridin-2-yl)methyl)(methyl)carbamate (114 mg, 0.158 mmol, 49.6% yield) as an orange oil. LCMS (System B, UV, ESI): Rt=0.84 min, [M+H]+ 572

Similarly prepared to intermediate 3 from Intermediate 2 were:

| Int | Structure | NMR | LCMS (System B, UV, ESI): |
|---|---|---|---|
| 16 | (S)-4-(6-chloro-4-(2-(methylsulfonyl)propan-2-yl)pyridin-2-yl)-3-methylmorpholine | 1H NMR (400 MHz, DMSO-d6) δ ppm 1.13 (d, J = 6.85 Hz, 3 H) 1.70 (s, 6 H) 2.80 (s, 3 H) 3.08 (td, J = 12.72, 3.91 Hz, 1 H) 3.46 (td, J = 11.80, 3.06 Hz, 1 H) 3.58-3.65 (m, 1 H) 3.68-3.75 (m, 1 H) 3.86 (dd, J = 13.20, 2.20 Hz, 1 H) 3.93 (dd, J = 11.37, 3.55 Hz, 1 H) 4.24-4.34 (m, 1 H) 6.78 (s, 1 H) 6.83 (s, 1 H) | $R_t$ = 1.02 min, [M + H]$^+$ 333 |
| 17 | (1R,5S)-8-(6-chloro-4-(2-(methylsulfonyl)propan-2-yl)pyridin-2-yl)-3-oxa-8-azabicyclo[3.2.1]octane | $^1$H NMR (400 MHz, CHLOROFORM-d) δ ppm 1.76-1.84 (m, 6 H) 1.96-2.05 (m, 2 H) 2.08-2.19 (m, 2 H) 2.63-2.69 (m, 3 H) 3.62 (d, J = 11.00 Hz, 2 H) 3.81 (d, J = 10.76 Hz, 2 H) 4.46 (br. s., 2 H) 6.74 (dd, J = 16.26, 1.35 Hz, 2 H) | $R_t$ = 1.01 min, [M + H]$^+$ 345 |
| 18 | 3-(6-chloro-4-(2-(methylsulfonyl)propan-2-yl)pyridin-2-yl)-8-oxa-3-azabicyclo[3.2.1]octane | $^1$H NMR (400 MHz, CHLOROFORM-d) δ ppm 1.80 (s, 6 H) 1.82-1.92 (m, 2 H) 2.00 (dd, J = 8.31, 4.40 Hz, 2 H) 2.66 (s, 3 H) 3.13-3.23 (m, 2 H) 3.81 (d, J = 12.23 Hz, 2 H) 4.51 (d, J = 2.45 Hz, 2 H) 6.70 (d, J = 0.98 Hz, 1 H) 6.81 (d, J = 0.98 Hz, 1 H) | $R_t$ = 1.01 min, [M + H]$^+$ 345 |

| Int | Structure | NMR | LCMS (System B, UV, ESI): |
|---|---|---|---|
| 19 | 9-(6-chloro-4-(2-(methylsulfonyl)propan-2-yl)pyridin-2-yl)-3-oxa-9-azabicyclo[3.3.1]nonane | ¹H NMR (400 MHz, CHLOROFORM-d) δ ppm 1.56 (s, 6 H) 1.63 (s, 2 H) 1.77-1.98 (m, 10 H) 2.57-2.72 (m, 2 H) 3.86-3.97 (m, 2 H) 3.99-4.07 (m, 2 H) 6.73 (dd, J = 6.97, 1.10 Hz, 2 H) | $R_t$ = 1.11 min, [M + H]⁺ 359 |

Similarly prepared to intermediate 3 from Intermediate 1 was:

| Int | Structure | NMR | LCMS (System B, UV, ESI): |
|---|---|---|---|
| 20 | (S)-4-(6-chloro-4-((methylsulfonyl)methyl)pyridin-2-yl)-3-methylmorpholine | 1H NMR (400 MHz, DMSO-d6) δ ppm 1.14 (d, J = 6.85 Hz, 3 H) 2.97 (s, 3 H) 3.09 (td, J = 12.72, 3.91 Hz, 1 H) 3.46 (td, J = 11.80, 3.06 Hz, 1H) 3.58-3.64 (m, 1 H) 3.69-3.75 (m, 1 H) 3.81 (dd, J = 13.33, 2.32 Hz, 1 H) 3.93 (dd, J = 11.49, 3.67 Hz, 1 H) 4.19 (dd, J = 6.60, 2.45 Hz, 1 H) 4.44 (s, 2 H) 6.71 (s, 1 H) 6.75 (s, 1 H) | $R_t$ = 0.91 min, [M + H]⁺ 305 |

Intermediate 21: (S)-4-(6-chloro-4-(2-(ethylsulfonyl)propan-2-yl)pyridin-2-yl)-3-methylmorpholine A solution of (S)-4-(6-chloro-4-(2-(methylsulfonyl)propan-2-yl)pyridin-2-yl)-3-methylmorpholine, (the compound of Intermediate 16, 100 mg, 0.300 mmol) in anhydrous Tetrahydrofuran (THF) (1 mL) was cooled to 0° C. and placed under Nitrogen. sodium hydride (14.42 mg, 0.601 mmol, Aldric H) was added and the reaction mixture stirred at 0° C. for 15 minutes. methyl iodide (0.038 mL, 0.601 mmol, Aldrich) was added and the reaction stirred for 2 hours at room temperature. potassium tert-butoxide 1 M in THF (0.601 mL, 0.601 mmol, Aldrich) was added and the resulting solution stirred at room temperature for 6 hours, then left to stand overnight. methyl iodide (0.038 mL, 0.601 mmol, Aldrich) and additional potassium tert-butoxide 1 M in THF (0.3 mL, Aldrich) were added and the solution stirred for 2 hours. Additional methyl iodide (0.02 mL, Aldrich) was added and the solution stirred at room temperature overnight. Additional potassium tert-butoxide 1 M in THF (0.3 mL, Aldrich) and methyl iodide (0.02 mL, Aldrich) were added and the solution stirred at room temperature overnight. The reaction was quenched by the addition of saturated aqueous ammonium chloride (10 mL). The mixture was diluted with ethyl acetate (15 mL) and washed with water (2×15 mL) then brine (15 mL). The organic layer was concentrated in vacuo, dissolved in 1:1 DMSO:MeOH (1 mL) and purified by high pH MDAP. Fractions were concentrated to give (S)-4-(6-chloro-4-(2-(ethylsulfonyl)propan-2-yl)pyridin-2-yl)-3-methylmorpholine (39.7 mg, 0.114 mmol, 38.1% yield) as a white solid. ¹H NMR (400 MHz, CHLOROFORM-d) δ ppm 1.23-1.36 (m, 6H) 1.80 (s, 6H) 2.68-2.83 (m, 2H) 3.24 (td, J=12.72, 3.91 Hz, 1H) 3.61 (td, J=11.86, 3.18 Hz, 1H) 3.71-3.85 (m, 2H) 3.90 (dd, J=13.20, 2.69 Hz, 1H) 4.03 (dd, J=11.49, 3.91 Hz, 1H) 4.23-4.32 (m, 1H) 6.77 (dd, J=6.97, 1.10 Hz, 1H). LCMS (System B, UV, ESI): LCMS (System B, UV, ESI): $R_t$=1.08 min, [M+H]⁺ 347

Intermediate 22: 2,6-dichloro-4-((cyclopropylsulfonyl)methyl)pyridine

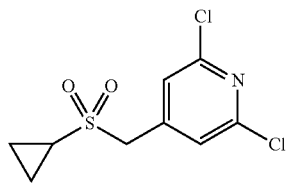 [SMILES: O=S(=O)(Cc1cc(Cl)nc(Cl)c1)C1CC1]

A solution of 2,6-dichloro-4-(chloromethyl)pyridine (200 mg, 1.018 mmol, Apollo Scientific), sodium cyclopropanesulfinate (196 mg, 1.527 mmol, Fluorochem) and potassium iodide (33.8 mg, 0.204 mmol, Aldrich) in anhydrous Acetonitrile (5 mL) was stirred at reflux for 2.5 hours under Nitrogen. The solution was cooled to room temperature, diluted with water (10 mL) and extracted with ethyl acetate (3×20 mL). The organic layers were concentrated to give a residue that was preabsorbed onto Florisil and purified by normal phase chromatography, eluting 0-75% ethyl acetate in cyclohexane. Fractions were concentrated to give a white solid, 2,6-dichloro4((cyclopropylsulfonyl)methyl) pyridine (195 mg, 0.733 mmol, 72.0% yield)$^1$H NMR (400 MHz, DMSO-$d_6$) δ ppm 0.91 (dd, J=4.52, 2.81 Hz, 2H) 1.02 (dd, J=7.95, 2.57 Hz, 2H) 2.68-2.80 (m, 1H) 4.72 (s, 2H) 7.63 (s, 2H). LCMS (System B, UV, ESI): LCMS (System B, UV, ESI): $R_t$=0.86 min, [M+H]$^+$ 266

Intermediate 23: 2,6-dichloro-4-(2-(cyclopropylsulfonyl)propan-2-yl)pyridine

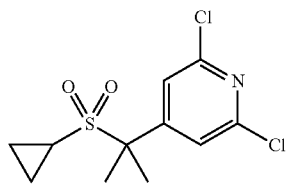 [SMILES: CC(C)(c1cc(Cl)nc(Cl)c1)S(=O)(=O)C1CC1]

A stirred solution of 2,6-dichloro-4-((cyclopropylsulfonyl)methyl)pyridine (the compound of Intermediate 22, 195 mg, 0.733 mmol) in anhydrous Tetrahydrofuran (THF) (1 mL) was purged with nitrogen 3× and cooled to 0° C. potassium tert-butoxide (200 mg, 1.782 mmol, Aldrich) was added and the solution stirred for 15 minutes, then iodomethane (0.1 mL, 1.599 mmol, Aldrich) was added dropwise. The reaction mixture was stirred under nitrogen at 0° C. for 1.5 hrs then quenched by the addition of saturated aqueous ammonium chloride (10 mL).

The mixture was diluted with ethyl acetate (20 mL) and washed with water (2×20 mL) then brine (20 mL). The organic layer concentrated in vacuo to give a white solid, 2,6-dichloro-4-(2-(cyclopropylsulfonyl)propan-2-yl)pyridine (197 mg, 0.670 mmol, 91% yield). $^1$H NMR (400 MHz, CHLOROFORM-d) δ ppm 0.93-1.05 (m, 2H) 1.05-1.16 (m, 2H) 1.87 (s, 6H) 2.08-2.21 (m, 1H) 7.54 (s, 2H). LCMS (System B, UV, ESI): LCMS (System B, UV, ESI): $R_t$=0.99 min, [M+H]$^+$ 294

Intermediate 24: (S)-4-(6-chloro-4-(2-(cyclopropylsulfonyl)propan-2-yl)pyridin-2-yl)-3-methylmorpholine

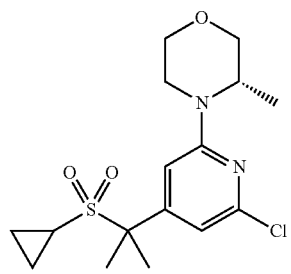 [SMILES: C[C@H]1COCCN1c1cc(C(C)(C)S(=O)(=O)C2CC2)cc(Cl)n1]

2,6-dichloro-4-(2-(cyclopropylsulfonyl)propan-2-yl)pyridine, (the compound of intermediate 23, 96 mg, 0.326 mmol), (S)-3-methylmorpholine (0.044 mL, 0.392 mmol), and DIPEA (0.171 mL, 0.979 mmol) were combined in Dimethyl Sulfoxide (DMSO) (0.3 mL) in a sealed microwave vial and the resulting mixture stirred at 135° C. for 40 hours. The solution was cooled to room temperature, diluted with ethyl acetate (20 mL) and washed with water (2×15 mL) then brine (20 mL). The organic layer was triturated in diethyl ether (10 mL) then concentrated in vacuo to give a brown gum, (S)-4-(6-chloro-4-(2-(cyclopropylsulfonyl)propan-2-yl)pyridin-2-yl)-3-methylmorpholine (116.6 mg, 0.260 mmol, 80% yield) $^1$H NMR (400 MHz, CHLOROFORM-d) δ ppm 0.94 (dd, J=8.07, 2.45 Hz, 2H) 1.09 (td, J=4.71, 2.81 Hz, 2H) 1.58 (s, 3H) 1.82 (s, 6H) 2.09-2.18 (m, 1H) 3.19-3.32 (m, 1H) 3.61 (td, J=11.86, 3.18 Hz, 1H) 3.71-3.83 (m, 2H) 3.89 (dd, J=13.08, 2.81 Hz, 1H) 4.02 (dd, J=11.37, 3.79 Hz, 1H) 4.23-4.35 (m, 1H) 6.73-6.85 (m, 2H). LCMS (System B, UV, ESI): LCMS (System B, UV, ESI): $R_t$=1.09 min, [M+H]$^+$ 359

Similarly prepared were:

| Int | Structure | NMR | LCMS (System B, UV, ESI): |
|---|---|---|---|
| 25 | 6-chloro-4-[2(cyclopropanesulfonyl) propan-2-yl]pyridin-2-yl}-3methyl-morpholine | 1H NMR (400 MHz, CDCl3-d) δ ppm: 0.86-1.00 (m, 5 H), 1.06-1.13 (m, 2H), 1.62-1.73 (m, 1 H), 1.81 (s, 6 H), 1.89 (dt, J = 8.80, 6.85 Hz, 1 H), 2.08-2.18 (m, 1 H), 3.25 (dd, J = 12.72, 3.42 Hz, 1 H), 3.53-3.71 (m, 2 H), 3.90-4.03 (m, 4 H), 6.67-6.84 (m, 2 H) | $R_t$ = 1.18 min, $[M + H]^+$ 373 |
| 26 | (S)-4-(6-chloro-4-((cyclopropanesulfonyl)methyl)pyridin-2-yl)-3-ethylmorpholine | 1H NMR (400 MHz, CDCl3-d) δ ppm: 0.95 (t, J = 7.46 Hz, 3 H), 1.02-1.12 (m, 2 H), 1.18-1.30 (m, 2 H), 1.56-1.76 (m, 1 H), 1.90 (ddd, J = 13.75, 8.74, 7.34 Hz, 1 H), 2.33 (tt, J = 7.95, 4.77 Hz, 1 H), 3.16-3.32 (m, 1 H), 3.52-3.71 (m, 2 H), 3.90-4.06 (m, 4 H), 4.13 (s, 2 H), 6.58 (br. s., 1 H), 6.65 (s, 1 H) | $R_t$ = 1.08 min, $[M + H]^+$ 345 |

Intermediate 27: (S)-4-(6-chloro-4-(1-(cyclopropylsulfonyl)cyclopropyl)pyridin-2-yl)-3-methylmorpholine

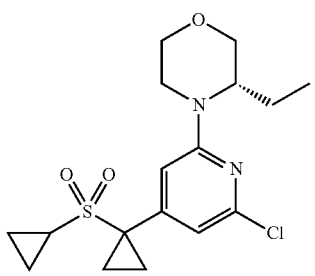 [SMILES: CC[C@H]1COCCN1c1cc(C2(S(=O)(=O)C3CC3)CC2)cc(Cl)n1]

(S)-4-(6-chloro-4-((cyclopropylsulfonyl)methyl)pyridin-2-yl)-3-ethylmorpholine (the compound of Intermediate 22, 100 mg, 0.290 mmol), 1,2-dibromoethane (0.037 mL, 0.435 mmol, Aldrich), tetrabutylammonium bromide (18.70 mg, 0.058 mmol, Aldrich) and sodium hydroxide (116 mg, 2.90 mmol, Alfa Aesar) were placed in a sealed microwave vial and dissolved in Toluene (5.800 mL). The reaction mixture was stirred at 60° C. for 17 hours and 110° C. for a further 5 hours. The reaction mixture allowed to cool and the volatiles removed under reduced pressure to give a residue that was partitioned between EtOAc (40 mL) and a mixture of water (20 mL) and saturated ammonium chloride solution (12 mL). The phases were separated and the organic phase was washed with brine (20 mL), passed through a hydrophobic frit and concentrated under reduced pressure. The residue was re-dissolved in water, basified to pH 14 and re-extracted with EtOAc. The organic layer was passed through a hydrophobic frit, concentrated under reduced pressure and dried in the vacuum oven to yield (S)-4-(6-chloro-4-(1-(cyclopropylsulfonyl)cyclopropyl)pyridin-2-yl)-3-ethylmorpholine (75.6 mg, 0.204 mmol, 70.3% yield).
$^1$H NMR (400 MHz, CHLOROFORM-d) δ ppm 0.89-1.03 (m, 3H) 1.04-1.14 (m, 2H) 1.22-1.31 (m, 2H) 1.59-1.75 (m, 2H) 1.76-1.82 (m, 2H) 1.82-1.96 (m, 2H) 2.31 (tt, J=7.98, 4.86 Hz, 1H) 3.24 (td, J=12.65, 3.79 Hz, 1H) 3.54-3.70 (m, 2H) 3.89-4.07 (m, 4H) 6.75 (s, 2H). LCMS (System B, UV, ESI): $R_t$=1.19 min, $[M+H]^+$ 371

Intermediate 28: 2,6-dichloro-4-(difluoro(methylsulfonyl)methyl)pyridine

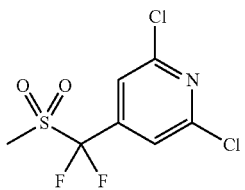

To a solution of 2,6-dichloro-4-((methylsulfonyl)methyl) pyridine (the compound of Intermediate 1, 295 mg, 1.229 mmol) in anhydrous Tetrahydrofuran (THF) (15 mL) was added LHMDS (1 M in THF, Aldrich) (2.457 mL, 2.457 mmol) at 0° C. and the resulting mixture stirred for 5 minutes. N-fluorobenzenesulfonimide (852 mg, 2.70 mmol, Apollo scientific) was added and the solution stirred at 0° C. for 1 hour. The mixture was diluted with ethyl acetate (20 mL) and washed with water (2×20 mL) then brine (20 mL). The organic layer was concentrated and the residue purified using reverse phase C18, eluting 30-70% acetonitrile in water modified by formic acid. Desired fractions were concentrated in vacuo to give 2,6-dichloro-4-(difluoro(methylsulfonyl)methyl) pyridine (166 mg, 0.601 mmol, 48.9% yield) as a white solid. $^1$H NMR (400 MHz, CHLOROFORM-d) δ ppm 3.21 (t, J=0.98 Hz, 3H) 7.57 (s, 1H). LCMS (System B, UV, ESI): $R_t$=1.02 min, [M+H]$^+$ 276

Intermediate 29: (S)-4-(6-chloro-4-(difluoro(methylsulfonyl)methyl)pyridin-2-yl)-3-methylmorpholine

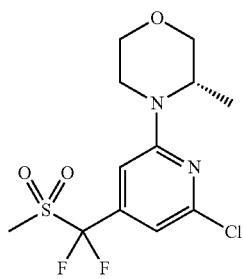

A stirred solution of 2,6-dichloro-4-(difluoro(methylsulfonyl)methyl)pyridine (the compound of Intermediate 28, 80 mg, 0.290 mmol) and (S)-3-methylmorpholine (0.036 mL, 0.319 mmol, Fluorochem) in anhydrous Dimethyl Sulfoxide (DMSO) (0.8 mL) in a crimp capped microwave vial under nitrogen was treated with DIPEA (0.152 mL, 0.869 mmol,). The resulting colourless solution was heated at 130° C. for 4 hr. The resulting solution was partitioned between ethyl acetate (30 mL) and water (50 mL). The organic phase was washed with water (20 mL) and brine (20 mL) then passed through a hydrophobic frit and concentrated in vacuo. The reaction mixture was dissolved in DMSO:methanol (~1 mL) and purified by MDAP. The appropriate fractions were combined and concentrated in vacuo to give (S)-4-(6-chloro-4 (difluoro(methylsulfonyl)methyl)pyridin-2-yl)-3-methylmorpholine (58.4 mg, 0.171 mmol, 59.1% yield) as an off-white crystalline solid. $^1$H NMR (400 MHz, CHLOROFORM-d) δ ppm 1.31 (d, J=6.85 Hz, 3H) 3.28 (td, J=12.72, 3.91 Hz, 1H) 3.60 (td, J=11.86, 3.18 Hz, 1H) 3.71-3.87 (m, 2H) 3.93 (dd, J=13.33, 2.81 Hz, 1H) 4.03 (dd, J=11.49, 3.91 Hz, 1H) 4.24-4.35 (m, 1H) 6.65 (s, 1H) 6.84 (s, 1H). LCMS (System B, UV, ESI): $R_t$=1.13 min, [M+H]$^+$ 341

Intermediate 30: (S)-4-(6-chloro-4-((methylsulfonyl)methyl)pyridin-2-yl)-3-ethylmorpholine

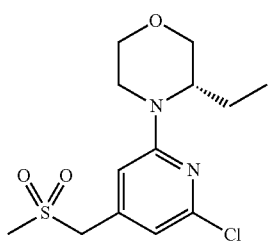 [SMILES: CC[C@H]1COCCN1c1cc(CS(C)(=O)=O)cc(Cl)n1]

To a solution of 2,6-dichloro-4-((methylsulfonyl)methyl) pyridine (500 mg, 2.082 mmol, the compound of Intermediate 1) and (S)-3-ethylmorpholine hydrochloride (588 mg, 3.12 mmol, Ark Pharm) in Dimethyl Sulfoxide (DMSO) (1.32 mL) was added DIPEA (1.091 mL, 6.25 mmol, Aldrich) and the reaction mixture was stirred at 130° C. for 24 hours then left standing at room temperature for 66 hours. To the reaction mixture was added further (S)-3-ethylmorpholine hydrochloride (250 mg, 1.33 mmol) and DIPEA (0.463 mL, 2.66 mmol) and the reaction mixture was stirred at 130° C. for a further 18 hours. The reaction mixture was diluted with water (30 mL) and extracted with EtOAc (2×40 mL). The combined organics were washed with brine then passed through a hydrophobic frit and concentrated under reduced pressure. The residue was re-dissolved in DCM and absorbed onto Florisil for purification on silica gel eluting 0-65% EtOAc in cyclohexane over 35 minutes. Fractions containing the desired product were combined, concentrated under reduced pressure and dried in the vacuum oven to yield (S)-4-(6-chloro-4-((methylsulfonyl)methyl)pyridin-2-yl)-3-ethylmorpholine (209.9 mg, 0.658 mmol, 31.6% yield). 1H NMR (400 MHz, CHLOROFORM-d) δppm: 0.87-1.00 (m, 3H) 1.63-1.75 (m, 1H) 1.82-1.97 (m, 1H) 2.86 (s, 3H) 3.25 (td, J=12.78, 3.79 Hz, 1H) 3.53-3.69 (m, 2H) 3.91-4.04 (m, 4H) 4.08-4.13 (m, 2H) 6.50 (s, 1H, pyridine C H) 6.58 (s, 1H). LCMS (System B, UV, ESI): $R_t$=1.00 min, [M+H]$^+$ 319

Intermediate 31: (S)-4-(6-chloro-4-(4-(methylsulfonyl)tetrahydro-2H-pyran-4-yl)pyridin-2-yl)-3-ethylmorpholine

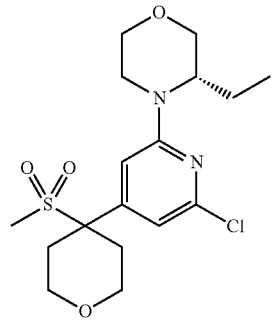 [SMILES: CC[C@H]1COCCN1c1cc(C2(S(C)(=O)=O)CCOCC2)cc(Cl)n1]

(S)-4-(6-chloro-4-((methylsulfonyl)methyl)pyridin-2-yl)-3-ethylmorpholine (208 mg, 0.652 mmol, the compound of intermediate 30), 1-bromo-2-(2-bromoethoxy)ethane (0.123 mL, 0.979 mmol, Aldrich), tetrabutylammonium bromide (42.1 mg, 0.130 mmol, Aldrich) and sodium hydroxide (261 mg, 6.52 mmol, Alfa Aesar) were placed in a microwave vial and dissolved in Toluene (13 mL).

The vial was sealed and the reaction mixture was stirred at 90° C. for 2 hours then at 110° C. for 17 hours. The reaction mixture was allowed to cool then concentrated under reduced pressure. The residue was partitioned between ethyl acetate (40 mL) and water (40 mL). The organic phase was washed with brine (40 mL), passed through a hydrophobic frit then concentrated under reduced pressure and dried under a stream of nitrogen to yield (S)-4-(6-chloro-4-(4-(methylsulfonyl)tetrahydro-2H-pyran-4-yl)pyridin-2-yl)-3-ethylmorpholine (235.8 mg, 0.546 mmol, 84% yield) as a brown solid. 1H NMR (400 MHz, CHLOROFORM-d) δ ppm: 0.94 (t, J=7.58 Hz, 3H) 1.62-

1.72 (m, 1H) 1.83-1.98 (m, 1H) 2.33 (d, J=13.94 Hz, 2H) 2.55-2.64 (m, 5H) 3.17-3.29 (m, 1H) 3.42 (d, J=13.45 Hz, 2H) 3.55-3.70 (m, 2H) 3.90-4.09 (m, 6H) 6.55-6.69 (m, 2H). LCMS (System A, UV, ESI): $R_t$=1.04 min, $[M+H]^+$ 389

Intermediate 32: 1-(2,6-dichloropyridin-4-yl)-N,N-dimethylmethanesulfonamide

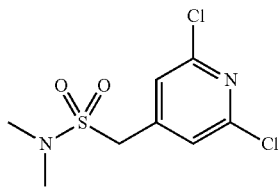

To a solution of N,N-dimethylmethanesulfonamide (1013 mg, 8.22 mmol, Flourochem) in Tetrahydrofuran (THF) (10 mL) under nitrogen at −15 deg C. was added n-butyllithium (3.5 mL, 8.75 mmol, SigmaAldrich). 2,4,6-trichloropyridine (500 mg, 2.74 mmol, SigmaAldrich) in 5 mL THF was added dropwise and the reaction mixture was allowed to warm to rt and stirred for 2 h. Reaction mixture quenched with 15 mL saturated ammonium chloride solution and left to stand for 16 h. The mixture was partitioned between Sat. ammonium chloride solution (100 mL) and EtOAc (100 mL). The organic layer was separated, dried over a hydrophobic frit, and concentrated under reduced pressure. The residue was dissolved in DCM (3.5 mL) and eluted on a silica gel column in cyclohexane with a gradient of 0-60% EtOAc. Desired fractions were concentrated under reduced pressure to give 1-(2,6-dichloropyridin-4-yl)-N,N-dimethyl-methanesulfonamide (470 mg, 0.908 mmol, 33.1% yield) as an off-white solid.

$^1$H NMR (400 MHz, CDCl$_3$): δ ppm: 7.34 (s, 2H), 4.11 (s, 2H), 2.89 (s, 6H). LCMS (System B, UV, ESI): $R_t$=0.92 mins, $[M+H]^+$ 267.1

Intermediate 33: (S)-1-(2-chloro-6-(3-ethylmorpholino)pyridin-4-yl)-N,N-dimethylmethane-sulfonamide

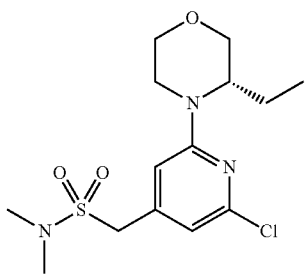 [SMILES: CC[C@H]1COCCN1c1cc(CS(=O)(=O)N(C)C)cc(Cl)n1]

To 1-(2,6-dichloropyridin-4-yl)-N,N-dimethylmethanesulfonamide (400 mg, 0.773 mmol, the compound of Intermediate 32), (S)-3-ethylmorpholine (188 mg, 1.632 mmol, Activate Scientific), and DIPEA (0.33 ml, 1.889 mmol, SigmaAldrich) was added anhydrous Dimethyl Sulfoxide (DMSO) (1.5 ml). The reaction mixture was heated at 130° C. for 40 h. The reaction mixture was diluted with 1.5 mL water, then partitioned between brine (10 mL) and EtOAc (10 mL). The organic layer was separated and the aqueous layer was back-extracted with EtOAc (10 mL). The organic layers were combined, dried over a hydrophobic frit, and concentrated under reduced pressure. The residue was dissolved in DCM (1.5 mL) and eluted on a silica gel column in cyclohexane with a gradient of 0-70% EtOAc. Collected fractions were submitted to LCMS and the desired fractions were concentrated under reduced pressure. The residue was dissolved in 3 mL DMSO and purified by open access MDAP (HPH Method C, The desired fractions were concentrated under reduced pressure to give (S)-1-(2-chloro-6-(3-ethylmorpholino)pyridin-4-yl)-N,N-dimethylmethanesulfonamide.

$^1$H NMR (400 MHz, CHLOROFORM-d) δ ppm 0.93 (t, J=7.46 Hz, 3H) 1.58-1.72 (m, 1H) 1.80-1.94 (m, 1H) 3.21 (td, J=12.70, 3.42 Hz, 1H) 3.56 (td, J=12.20, 3.18 Hz, 1H) 3.62 (dd, J=11.49, 2.93 Hz, 1H) 3.94 (dd, J=15.89, 11.74 Hz, 4H), 4.04 (s, 2H), 6.48 (s, 1H), 6.56 (s, 1H). LCMS (System B, UV, ESI): $R_t$=1.12 mins, $[M+H]^+$ 348

Intermediate 34: 2,6-dichloro-4-(1-(methylsulfonyl)cyclopropyl)pyridine

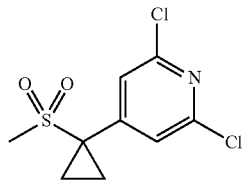

To a stirred solution of Intermediate 1 (3 g, 12.49 mmol) in Toluene (15 mL) was added powdered potassium hydroxide (3.51 g, 62.5 mmol) and tetrabutylammonium bromide (0.793 g, 2.461 mmol). To the above reaction mixture was added 1,2-dibromoethane (1.623 mL, 18.74 mmol) at 0° C. stirred for 2 hr at ambient temperature. DCM (50 mL), saturated ammonium chloride (10 mL) and water (50 mL) were added. The aqueous phase was extracted with DCM (100 mL). All organic layers were concentrated and purified by reverse phase chromatography to give 2,6-dichloro-4-(1-(methylsulfonyl)cyclopropyl)pyridine (1.2 g, 4.46 mmol, 35.7% yield) as pale yellow solid. LCMS (System B, UV, ESI): $R_t$=1.93 min, $[M+H]^+$ 266

Intermediate 35: (S)-4-(6-chloro-4-(1-(methylsulfonyl)cyclopropyl)pyridin-2-yl)-3-ethylmorpholine

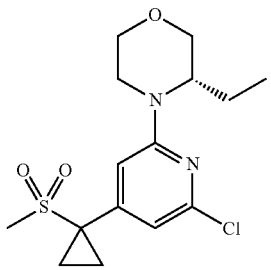 [SMILES: CC[C@H]1COCCN1c1cc(C2(S(C)(=O)=O)CC2)cc(Cl)n1]

DIPEA (450 μl, 2.58 mmol) was added to a mixture of Intermediate 34 (250 mg, 0.939 mmol) and (S)-3-ethylmorpholine hydrochloride (214 mg, 1.409 mmol, Manchester Organics) in Dimethyl Sulfoxide (DMSO) (700 μl). The reaction vessel was sealed and stirred at 130° C. for 64 h. The reaction mixture was partitioned between ethyl acetate (40 ml) and saturated ammonium chloride solution (40 ml). The phases were separated and the aqueous phase was extracted with ethyl acetate (2×30 ml). The organic phases were combined, washed with water (20 ml), washed with brine (20 ml) and dried over magnesium sulfate. The crude product adsorbed on solid phase (Florisil) was purified by column chromatography on silica (80 g) using the elution gradient ethyl acetate in cyclohexane 0 to 70% to give (S)-4-(6-chloro-4-(1-(methylsulfonyl)cyclopropyl)pyridin-2-yl)-3-ethylmorpholine (125.2 mg, 0.363 mmol, 38.6% yield). LCMS (System B, UV, ESI): $R_t$=1.08 min, $[M+H]^+$ 345

Intermediate 36: (S)-4-(6-chloro-4-(1-(methylsulfonyl)cyclopropyl)pyridin-2-yl)-3-methylmorpholine

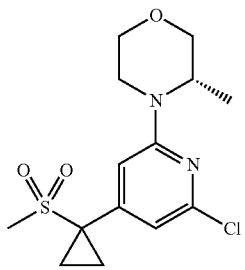

DIPEA (250 μl, 1.431 mmol) was added to Intermediate 34 (202 mg, 0.759 mmol) and (S)-3-methylmorpholine (130 μl, 1.321 mmol, Manchester Organics) in Dimethyl Sulfoxide (DMSO) (3500 μl). The reaction mixture was stirred at 130° C. for 20.75 h. The reaction mixture was partitioned between ethyl acetate (50 ml) and saturated ammonium chloride (50 ml). The aqueous phase was further extracted with ethyl acetate (2×40 ml). The organic phases were combined, washed with water (40 ml) and brine (40 ml), dried over magnesium sulfate and concentrated under reduced pressure. The crude product was adsorbed on Florisil and purified by column chromatography on silica (40 g) using the elution gradient ethyl acetate in cyclohexane 0 to 100% to yield (S)-4-(6-chloro-4-(1-(methylsulfonyl)cyclopropyl)pyridin-2-yl)-3-methylmorpholine (83.5 mg, 0.252 mmol, 33.3% yield). LCMS (System B, UV, ESI): $R_t$=0.99 min, $[M+H]^+$ 331

Intermediate 37: tert-butyl (3-(3-amino-6-chloropyridin-2-yl)prop-2-yn-1-yl)carbamate

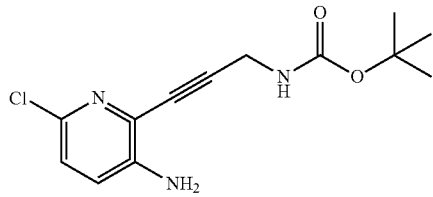

A mixture of 2-bromo-6-chloropyridin-3-amine (1 g, 4.82 mmol, Fluorochem), 2-bromo-6-chloropyridin-3-amine (1 g, 4.82 mmol, Alfa Aesar), copper I iodide (0.092 g, 0.482 mmol), PdCl2(dppf) (0.353 g, 0.482 mmol) and TEA (1.008 mL, 7.23 mmol) in Tetrahydrofuran (THF) (20 mL) was degassed under a flow of nitrogen for 10 min. The reaction mixture was heated to 70° C. for 16 h. The mixture was cooled down to RT. EtOAc (20 mL) was added and the resulting mixture was filtered through Celite (2.5 g cartridge). The residual solid was washed with additional EtOAc (2×20 mL) The filtrate was collected and washed with saturated ammonium chloride solution (50 mL), water (50 mL), brine (50 mL) and dried over MgSO4. The volatiles were removed under reduced pressure to give a residue that was purified by column chromatography on Silica (120 g Cartridge, dry load on Florisil) using the elution gradient EtOAc in Cyclohexane 0-100% to give tert-butyl (3-(3-amino-6-chloropyridin-2-yl)prop-2-yn-1-yl)carbamate (1.1635 g, 4.13 mmol, 86% yield) as a orange solid. LCMS (System B, UV, ESI): $R_t$=0.96 min, $[M+H]^+$ 282

Intermediate 38: tert-butyl ((5-chloro-1H-pyrrolo[3,2-b]pyridin-2-yl)methyl)carbamate

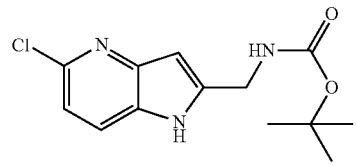 [SMILES: CC(C)(C)OC(=O)NCc1cc2nc(Cl)ccc2[nH]1]

Intermediate 37 (1.16 g, 4.12 mmol) was dissolved in Tetrahydrofuran (THF) (10 ml) and KOtBu (0.601 g, 5.35 mmol) was added. The reaction mixture was stirred at RT for (17 h). The reaction mixture was partitioned between EtOAc (20 mL) and saturated ammonium chloride solution (20 mL). The phases were separated and the organic phase was washed with Brine (20 mL) and dried over MgSO4. The volatiles were removed under reduced pressure to give a residue that was purified by Reverse phase chromatography (400 g C18 Cartridge) using the elution gradient Acetonitrile in water (Formic acid modifier) 20-80% to give tert-butyl ((5-chloro-1H-pyrrolo[3,2-b]pyridin-2-yl)methyl)carbamate (88 mg, 0.312 mmol, 7.59% yield) as an orange solid.). LCMS (System B, UV, ESI): $R_t$=0.94 min, $[M+H]^+$ 282

Intermediate 39: 2,6-dibromo-4-((methylsulfonyl)methyl)pyridine

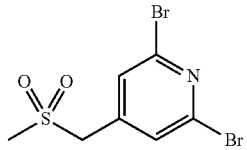

To a cooled (ice/water bath) solution of (2,6-dibromopyridin-4-yl)methanol (50.38 g, 189 mmol) and triethylamine (39.5 mL, 283 mmol) in N,N-Dimethylformamide (DMF) (250 mL) was added dropwise mesyl-Cl (17.65 mL, 226 mmol) over 5 mins. The reaction mixture was stirred at between 0° C. and 5° C. for 135 min. To the reaction mixture was added methanesulfinic acid, sodium salt (28.9 g, 283 mmol) and the reaction mixture was stirred under nitrogen at 60 C for 90 minutes and room temperature over night.

Water (350 ml) was added and the mixture stirred for 40 minutes. The resulting slurry was filtered and then dried overnight under vacuum to give 2,6-dibromo-4-((methylsulfonyl)methyl)pyridine (44.58 g, 72%) as a beige solid. LCMS (System A, UV, ESI): R$_t$=0.82 min, [M+H]$^+$ 328

Intermediate 40: (S)-4-(6-bromo-4-((methylsulfonyl)methyl)pyridin-2-yl)-3-ethyl-morpholine

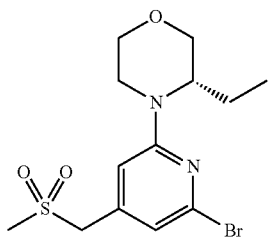

A mixture of Intermediate 39 2,6-dibromo-4-((methylsulfonyl)methyl)pyridine (43.55 g, 132 mmol), (S)-3-ethylmorpholine, Hydrochloride (26.1 g, 172 mmol, Novachemistry) and 2,2,6,6-tetramethylpiperidine (168 ml, 993 mmol, Matrix Scientific) was heated to 150 C under nitrogen for 24 hours. The reaction mixture was allowed to cool. The reaction mixture was diluted with saturated ammonium chloride (100 ml) and water (400 ml). The reaction mixture was extracted with ethyl acetate (500 ml). The aqueous phase was extracted with ethyl acetate (100 ml). The combined organic phases were washed with brine (200 ml) and dried over magnesium sulphate. The solvent was removed in vacuo. The residue was dissolved in DCM and applied to a 750 g silica cartridge. This was eluted with a gradient of 0-100% ethyl acetate in cyclohexane over 8CV. The required fractions were combined and evaporated in vacuo to give (S)-4-(6-bromo-4-((methylsulfonyl)methyl)pyridin-2-yl)-3-ethyl-morpholine (53.497 g, 111%) as a tan solid. LCMS (System B, UV, ESI): R$_t$=0.99 min, [M+H]$^+$ 365

Intermediate 41: (S)-4-(6-bromo-4-(4-(methylsulfonyl)tetrahydro-2H-pyran-4-yl)pyridin-2-yl)-3-ethyl-morpholine

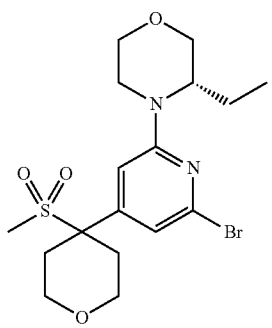

To a solution of Intermediate 40 (S)-4-(6-bromo-4-((methylsulfonyl)methyl)pyridin-2-yl)-3-ethylmorpholine (53.497 g, 147 mmol), 1-bromo-2-(2-bromoethoxy)ethane (27.8 mL, 221 mmol, Aldrich) and tetrabutylammonium bromide (9.49 g, 29.5 mmol, Aldrich) in Toluene (1500 mL) and Water (10 mL) was added sodium hydroxide (58.9 g, 1473 mmol) and the reaction mixture was stirred rapidly and heated to 110 C over 1 hour. The reaction mixture was heated at 110 C for a further 1 hour. The reaction mixture was separated between ethyl acetate (500 ml) and water (500 ml). The aqueous phase was extracted using ethyl acetate (400 ml). The combined organic phases were washed with brine and dried over magnesium sulphate. The solvent was removed in vacuo. The residue was dissolved in DCM and applied to a 1500 g silica cartridge. This was eluted with a gradient of 0-100% ethyl acetate in cyclohexane over 10 column volumes. The required fractions were combined and evaporated in vacuo to give (S)-4-(6-bromo-4-(4-(methylsulfonyl)tetrahydro-2H-pyran-4-yl)pyridin-2-yl)-3-ethylmorpholine (38.467 g, 60%) as a brown foam. LCMS (System B, UV, ESI): R$_t$=1.020 min, [M+H]$^+$ 435

Intermediate 42: (S)-methyl 3-((6-(3-ethylmorpholino)-4-(4-(methylsulfonyl)tetrahydro-2H-pyran-4-yl)pyridin-2-yl)sulfonyl)propanoate

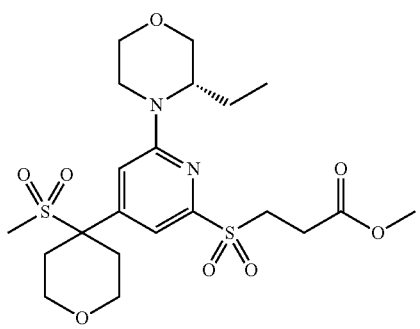

A mixture of Intermediate 41 (S)-4-(6-bromo-4-(4-(methylsulfonyl)tetrahydro-2H-pyran-4-yl)pyridin-2-yl)-3-ethylmorpholine (28.76 g, 66.4 mmol), sodium 3-methoxy-3-oxopropane-1-sulfinate (15.02 g, 86 mmol, Aldrich) and copper(I) iodide (16.43 g, 86 mmol) in Dimethyl Sulfoxide (DMSO) (130 mL) was heated to 110 C under nitrogen for 2 hours. The reaction mixture was separated between ethyl acetate (600 ml) and a dilute solution of ammonia (700 ml). The aqeuous phase was extracted using ethyl acetate (200 ml). The combined organic phases were washed with brine (300 ml) and dried over magnesium sulphate. The solvent was removed in vacuo. To the residue was added TBME (250 ml). The solid was collected by filtration, but started to gum on the filter paper. The solid was dissolved in and combined with the filtrate. This was evaporated in vacuo to give (S)-methyl 3-((6-(3-ethylmorpholino)-4-(4-(methylsulfonyl)tetrahydro-2H-pyran-4-yl)pyridin-2-yl)sulfonyl) propanoate (30.59 g, 91%) as a light brown solid/gum. LCMS (System B, UV, ESI): R$_t$=0.83 min, [M+H]$^+$ 505

Intermediate 43: sodium (S)-6-(3-ethylmorpholino)-4-(4-(methylsulfonyl)tetrahydro-2H-pyran-4-yl)pyridine-2-sulfinate

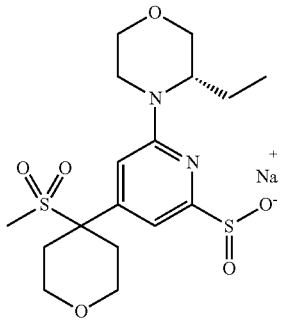

To a solution of Intermediate 42 methyl (S)-3-((6-(3-ethylmorpholino)-4-(4-(methylsulfonyl)tetrahydro-2H-pyran-4-yl)pyridin-2-yl)sulfonyl)propanoate (30.59 g, 60.6 mmol) in Tetrahydrofuran (THF) (300 mL) was added dropwise over 2 minutes sodium methoxide, 25% by weight in MeOH (14.56 mL, 63.7 mmol). The reaction mixture was stirred at room temperature under nitrogen for 1 hour. The solvent was removed in vacuo. The residue was dissolved in methanol (300 ml) and evaporated in vacuo. This was repeated. The pale tan foam was treated with diethyl ether (300 ml) and then evaporated in vacuo to give sodium (S)-6-(3-ethylmorpholino)-4-(4-(methylsulfonyl)tetrahydro-2H-pyran-4-yl)pyridine-2-sulfinate (28.39 g, 106%) as a tan solid. LCMS (System B, UV, ESI): $R_t$=0.82 min, [M+H]$^+$ 419

Intermediate 44 (the compound of intermediate 11): tert-butyl methyl(prop-2-yn-1-yl)carbamate

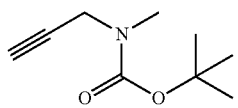

To a cooled, ice/water bath, solution of N-methylprop-2-yn-1-amine (17.6 g, 255 mmol, Aldrich) and triethylamine (39.0 mL, 280 mmol) in Dichloromethane (DCM) (300 mL) was added, portionwise, Boc-anhydride (65.0 mL, 280 mmol, Aldrich) (exothermic). The reaction mixture was stirred at room temperature for 18 hours. Water (100 ml) was added to the reaction mixture and this was stirred for 15 minutes. Saturated sodium bicarbonate solution (100 ml) was added and the phases were separated. The aqueous phase was extracted with DCM (200 ml). The combined organic phase was washed with brine and dried over magnesium sulphate. The solvent was removed in vacuo to give tert-butyl methyl(prop-2-yn-1-yl)carbamate (48.54 g, 111%) as a brown oil. $^1$H NMR (400 MHz, CHLOROFORM-d) δ 4.06 (br s, 2H), 2.93 (s, 3H), 2.23 (t, J=2.45 Hz, 1H), 1.49 (s, 9H).

Intermediate 45 (the compound of Intermediate 13): tert-butyl ((5-chloro-1H-pyrrolo[3,2-b]pyridin-2-yl)methyl)(methyl)-carbamatetert-butyl methyl(prop-2-yn-1-yl)carbamate

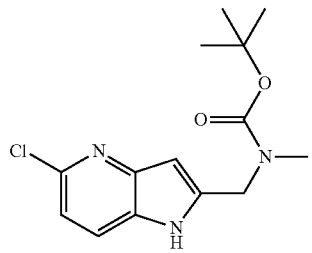 [SMILES: CN(Cc1cc2nc(Cl)ccc2[nH]1)C(=O)OC(C)(C)C]

A mixture of 2-bromo-6-chloropyridin-3-amine (11.15 g, 53.7 mmol, Fluorochem), Intermediate 44 tert-butyl methyl (prop-2-yn-1-yl)carbamate (13.64 g, 81 mmol), pyrrolidine (22.22 ml, 269 mmol) and bis(triphenylphosphine)palladium(II) chloride (1.886 g, 2.69 mmol) was stirred and heated at 60 C for 7 hours, LCMS showed mainly cyclised product. The reaction mixture was separated between ethyl acetate (250 ml) and water (100 ml). The organic phase was washed with brine (100 ml) and dried over magnesium sulphate. The solvent was removed in vacuo. The residue was dissolved in DCM and applied to a 330 g silica cartridge. This was eluted with a gradient of 0-100% ethyl acetate in cyclohexane over 30 minutes. The required fractions were combined and evaporated in vacuo to give tert-butyl ((5-chloro-1H-pyrrolo [3,2-b]pyridin-2-yl)methyl)(methyl)-carbamatetert-butyl methyl(prop-2-yn-1-yl)carbamate (9.339 g) as a tan solid. LCMS (System B, UV, ESI): $R_t$=1.03 min, [M+H]$^+$ 296

Intermediate 46: (S)-tert-butyl ((5-(6-(3-ethylmorpholino)-4-(4-(methylsulfonyl-tetrahydro-2H-pyran-4-yl)pyridin-2-yl)-1H-pyrrolo[3,2-b]pyridin-2-yl)methyl)(methyl)carbamate

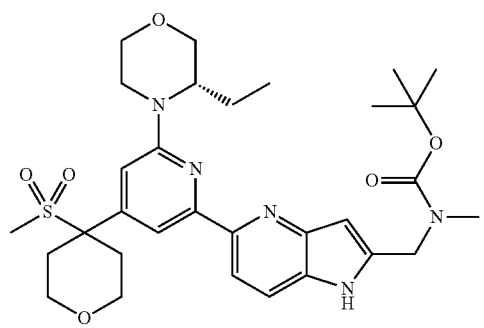

To Intermediate 45 tert-butyl ((5-chloro-1H-pyrrolo[3,2-b]pyridin-2-yl)methyl)(methyl)carbamate (17 g, 57.5 mmol), Intermediate 43 (S)-6-(3-ethylmorpholino)-4-(4-(methylsulfonyl)tetrahydro-2H-pyran-4-yl)pyridine-2-sulfinate, Sodium salt (27.9 g, 63.2 mmol), potassium carbonate (11.92 g, 86 mmol), palladium(II) acetate (1.290 g, 5.75 mmol) and tricyclohexylphosphine (3.22 g, 11.50 mmol) was suspended/dissolved in N,N-Dimethylformamide (DMF) (110 mL). The reaction mixture was degassed (vacuum/nitrogen×3) and heated at 130° C. for 3 hours. The reaction mixture was allowed to cool and separated between ethyl acetate (500 ml) and water (500 ml). The aqueous phase was extracted with ethyl acetate (250 ml). The combined organic phases were washed with brine (250 ml) and dried over magnesium sulphate. The solvent was removed in vacuo. The residue was dissolved in DCM and applied to a 750 g silica cartridge. This was eluted with a gradient of 0-100% ethyl acetate in cyclohexane over 10 column volumes. The required fractions were combined and evaporated in vacuo to give (S)-tert-butyl ((5-(6-(3-ethylmorpholino)-4-(4-(methylsulfonyl)-tetrahydro-2H-pyran-4-yl)pyridin-2-yl)-1H-pyrrolo[3,2-b]pyridin-2-yl)methyl)(methyl)carbamate. (27.999 g, 79%) as a brown foam. LCMS (System B, UV, ESI): $R_f$=0.76 min, [M+H]$^+$ 614

Intermediate 47: tert-butyl bis(2-chloroethyl)carbamate

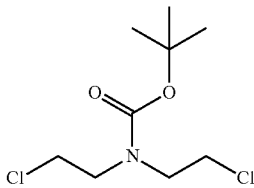

di-tert-butyl dicarbonate (1.482 g, 6.79 mmol, Aldrich) was added to bis(2-chloroethyl)amine hydrochloride (1.01 g, 5.66 mmol, Aldrich) in Dichloromethane (DCM) (30 mL) at 0° C. NaOH (10% in Water) (2.5 mL, 6.94 mmol) was added the reaction mixture stirred at 0° C. for 5 h. The reaction mixture was partioned between DCM (5 ml) and water (15 ml). The aqueous phase was further extracted with DCM (30 ml), the organic phases combined, dried over magnesium sulfate and concentrated under reduced pressure to yield tert-butyl bis(2-chloroethyl)carbamate 91.4 g, 102%). $^1$H NMR (400 MHz, CHLOROFORM-d) 3.61 (br s, 1H), 1.49 (s, 1H)

Intermediate 48: tert-butyl (S)-4-(2-bromo-6-(3-ethylmorpholino)pyridin-4-yl)-4-(methylsulfonyl) piperidine-1-carboxylate

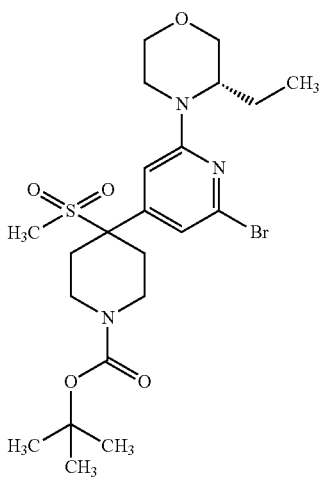 [SMILES: CC[C@H]1COCCN1c1cc(C2(S(C)(=O)=O)CCN(C(=O)OC(C)(C)C)CC2)cc(Br)n1]

sodium hydride (13.76 mg, 0.344 mmol) was added to Intermediate 40 (S)-4-(6-bromo-4-((methylsulfonyl)methyl) pyridin-2-yl)-3-ethylmorpholine (50 mg, 0.138 mmol) in dry N,N-Dimethylformamide (DMF) (1500 µl) under an atmosphere of nitrogen at 0° C. The reaction mixture was stirred at 0° C. for 30 min, then Intermediate 47 tert-butyl bis(2-chloroethyl)carbamate (50.5 µl, 0.206 mmol) was added and the reaction mixture was warmed up to RT and stirred at this temperature for 3 days. The reaction mixture was quenched by careful addition of saturated ammonium chloride solution (2 mL). The resulting mixture was extracted with DCM (5 mL). The volatiles were removed in vacuo and the residue was purified by reverse phase chromatography using the elution gradient acetonitrile in water 40-95% (formic acid modifier) to give tert-butyl (S)-4-(2-bromo-6-(3-ethylmorpholino)pyridin-4-yl)-4-(methylsulfonyl)piperidine-1-carboxylate (38 mg, 0.071 mmol, 51.8% yield) as a colourless oil. LCMS (System B, UV, ESI): $R_f$=1.28 min, [M+H]$^+$ 532+534

Intermediate 49: 3-(6-bromo-4-((methylsulfonyl) methyl)pyridin-2-yl)-8-oxa-3-azabicyclo[3.2.1]octane

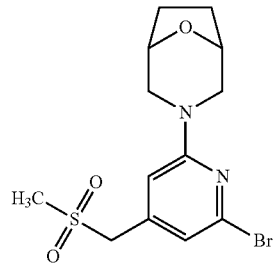

A sealed vial containing Intermediate 39 2,6-dibromo-4-((methylsulfonyl)methyl)pyridine (156 mg, 0.474 mmol) and 8-oxa-3-azabicyclo[3.2.1]octane, Hydrochloride (100 mg, 0.668 mmol, Fluorochem) was flushed with nitrogen. 2,2,6,6-tetramethylpiperidine (1.300 mL, 7.71 mmol) was added and the mixture heated to 170° C. under an atmosphere of N$_2$ gas for 7 h. The mixture was cooled to room temperature. The mixture was partitioned between EtOAc (50 mL) and saturated ammonium chloride aqueous solution (40 mL). The phases were separated and the organic phase was washed with water (2×30 mL) and passed through a hydrophobic frit. Solvent was removed under reduced pressure and purified by column chromatography and concentrated in vacuo to give 3-(6-bromo-4-((methylsulfonyl) methyl)pyridin-2-yl)-8-oxa-3-azabicyclo[3.2.1]octane (48 mg, 0.133 mmol, 28.0% yield) as a white solid LCMS (ESI, System B) Rt=0.89 min, [M+H]$^+$ 361+363

Intermediate 50: (R)-4-(6-bromo-4-((methylsulfonyl)methyl)pyridin-2-yl)-3-methyl-morpholine

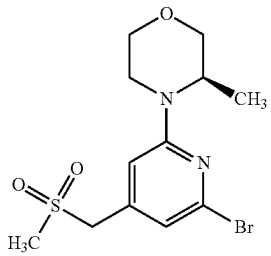 [SMILES: C[C@@H]1COCCN1c1cc(CS(C)(=O)=O)cc(Br)n1]

2,2,6,6-tetramethylpiperidine (2001 µl, 11.85 mmol) was added to Intermediate 39 2,6-dibromo-4-((methylsulfonyl)methyl)pyridine (250 mg, 0.760 mmol) and (R)-3-methylmorpholine (100 mg, 0.988 mmol). The reaction mixture was degassed under a flow of nitrogen for 5 min, sealed, heated to 150° C. for 16 h. The reaction mixture was cooled and quenched with saturated ammonium chloride aqueous solution and water, and extracted with ethyl acetate (2×). The organic phases were combined, washed with water and brine, dried over magnesium sulfate and concentrated in vacuo. The crude product was purified by column chromatography and concentrated in vacuo to give (R)-4-(6-bromo-4-((methylsulfonyl)methyl)pyridin-2-yl)-3-methylmorpholine (140 mg, 0.381 mmol, 50.1% yield) compound as a pale brown solid. LCMS (ESI, System B): Rt=0.9 min, [M+H]$^+$ 349+351

Intermediate 51: (S)-methyl 3-((6-(3-ethylmorpholino)-4-((methylsulfonyl)methyl)pyridin-2-yl)sulfonyl)propanoate

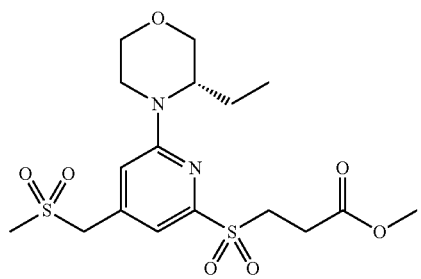

Intermediate 40 (S)-4-(6-bromo-4-((methylsulfonyl)methyl)pyridin-2-yl)-3-ethylmorpholine (500 mg, 1.376 mmol), copper(I) iodide (0.5 g, 2.63 mmol) and 3-methoxy-3-oxopropane-1-sulfinate, Sodium salt (0.500 g, 2.87 mmol, Aldrich) were placed in Dimethyl Sulfoxide (DMSO) (4 mL) and degassed under N2 gas for 20 minutes. The resulting reaction mixture was heated to 110° C. under an atmosphere of N2 for 1 hour. EtOAc (50 mL) was added to the cooled reaction mixture and the organic layer was washed with water, aqueous saturated NaHCO$_3$, aqueous saturated ammonium chloride (3×50 mL 2:2:1). The organic layers were combined, filtered through a hydrophobic frit and concentrated in vacuo to give a brown oil. The crude product was purified
by column chromatography on Silica eluting with EtOAc: Cyclohexane (60-100%). The relevant fractions were combined and concentrated in vacuo to give methyl (S)-3-((6-(3-ethylmorpholino)-4-((methylsulfonyl)methyl)pyridin-2-yl)sulfonyl)propanoate (550 mg, 1.266 mmol, 92% yield) as an orange oil. LCMS (System A, UV, ESI): R$_t$=0.83 min, [M+H]$^+$ 435

Intermediate 52: sodium (S)-6-(3-ethylmorpholino)-4-((methylsulfonyl)methyl)pyridine-2-sulfinate

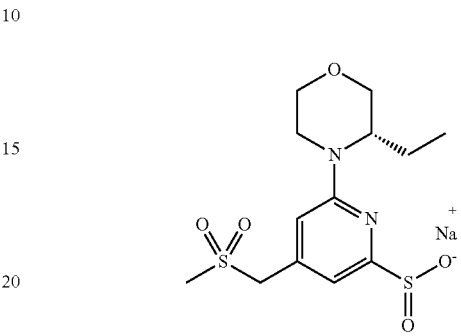

To a solution of Intermediate 51 methyl (S)-3-((6-(3-ethylmorpholino)-4-((methylsulfonyl)methyl)pyridin-2-yl)sulfonyl)propanoate Intermediate 49 (550 mg, 1.266 mmol) in anhydrous Tetrahydrofuran (THF) (4 mL) was added sodium methoxide (0.5 M in Methanol) (2.66 mL, 1.329 mmol) dropwise whilst stirring at room temperature. The reaction mixture was left to stir for 30 minutes. MeOH (5 mL) was added to the reaction mixture before being concentrated in vacuo to give (S)-6-(3-ethylmorpholino)-4-((methylsulfonyl)methyl)pyridine-2-sulfinate, Sodium salt (530 mg, 1.431 mmol, 113% yield) as an orange solid. LCMS (System A, UV, ESI): R$_t$=0.48 min, [M+H]$^+$ 349

Intermediate 53: (S)-2-bromo-6-(3-ethylmorpholino)isonicotinic acid

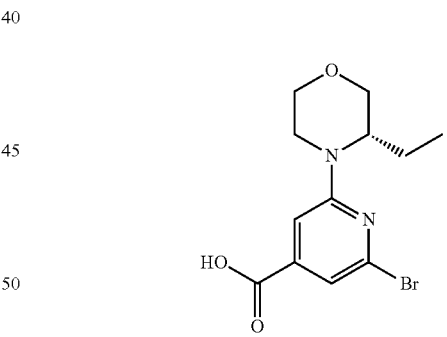

2,2,6,6-tetramethylpiperidine (10 ml, 59.3 mmol, Acros Organics) was added to 2,6-dibromoisonicotinic acid (2004 mg, 7.13 mmol, Fluorochem) and (S)-3-ethylmorpholine hydrochloride (1300 mg, 8.57 mmol, Manchester Organics). The vial containing reaction mixture was sealed, heated to 200° C. and stirred at 200° C. for 16 h. The reaction mixture was partitioned between DCM (100 mL) and water (150 mL) acidified with 2M HCl. The organic layer was separated and extracted with DCM (50 mL). The organic layers were combined, dried over a hydrophobic frit, and concentrated under reduced pressure. The residue was purified by reverse phase HPLC with a gradient of 30-85% acetonitrile+0.1% formic acid. Concentration in vacuo afforded (S)-2-bromo-6-(3-ethylmorpholino)isonicotinic acid (1268 mg, 4.02 mmol, 56.4% yield) as a brown solid. LCMS (System B, UV, ESI): $R_t$=1.14 min, [M+H]$^+$ 315+317

Intermediate 54: (S)-(2-bromo-6-(3-ethylmorpholino)pyridin-4-yl)methanol

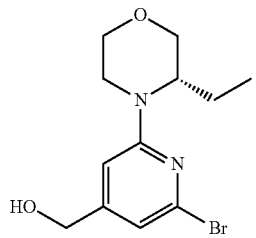

Borane-DMS complex (2M in THF) (3.2 ml, 6.40 mmol, Aldrich) was added to Intermediate 53 (S)-2-bromo-6-(3-ethylmorpholino)isonicotinic acid (1004 mg, 3.19 mmol) in dry Tetrahydrofuran (THF) (12 ml) under nitrogen at 0° C. The reaction mixture was stirred at 0° C. to RT for 18 h. The reaction mixture was cooled to 0° C. and quenched by dropwise addition of MeOH (5 mL). The mixture was stirred for 1.5 h at 0° C. The reaction mixture was concentrated. The residue was partitioned between 50 mL EtOAc and 50 mL sat. NH4Cl solution. The organic layer was dried over a hydrophobic frit, and concentrated in vacuo to give (S)-(2-bromo-6-(3-ethylmorpholino)pyridin-4-yl)methanol (938 mg, 3.11 mmol, 98% yield) as a brown gum. LCMS (System A, UV, ESI): $R_t$=1.02 min, [M+H]$^+$ 301+303

Intermediate 55: (S)-4-(6-bromo-4-(bromomethyl)pyridin-2-yl)-3-ethylmorpholine

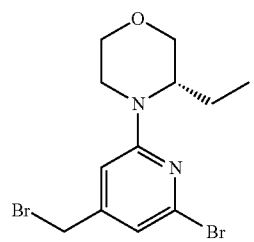

To a solution of Intermediate 54 (S)-(2-bromo-6-(3-ethylmorpholino)pyridin-4-yl)methanol (505 mg, 1.677 mmol) in Tetrahydrofuran (THF) (10 mL), triphenylphosphine (594 mg, 2.264 mmol) and 1-bromopyrrolidine-2,5-dione (388 mg, 2.180 mmol) were added at room temperature, and the mixture was stirred at RT for 75 min. The reaction mixture was diluted with saturated sodium bicarbonate solution and ethyl acetate. The organic layer was dried over a hydrophobic frit, and concentrated in vacuo. The residue was purified by column chromatography to give (S)-4-(6-bromo-4-(bromomethyl)pyridin-2-yl)-3-ethylmorpholine (451 mg, 1.239 mmol, 73.9% yield) as a colourless oil. LCMS (System A, UV, ESI): $R_t$=1.36 min, [M+H]$^+$ 365+367

Intermediate 56: (S)-methyl 3-(((2-bromo-6-(3-ethylmorpholino)pyridin-4-yl)methyl)sulfonyl) Propanoate

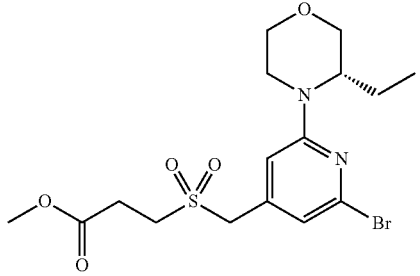 [SMILES: CC[C@H]1COCCN1c1cc(CS(=O)(=O)CCC(=O)OC)cc(Br)n1]

Intermediate 55 (S)-4-(6-bromo-4-(bromomethyl)pyridin-2-yl)-3-ethylmorpholine (354 mg, 0.972 mmol), sodium 3-methoxy-3-oxopropane-1-sulfinate (207 mg, 1.189 mmol, Sigma Aldrich), potassium iodide (48 mg, 0.289 mmol), and Acetonitrile (7 mL) were combined in a microwave vial which was heated at reflux for 1.5 h. The reaction mixture was partitioned between sat. sodium bicarbonate solution (50 mL) and EtOAc (50 mL). The organic layer was dried over a hydrophobic frit, and concentrated in vacuo to give methyl (S)-3-(((2-bromo-6-(3-ethylmorpholino)pyridin-4-yl)methyl)sulfonyl)propanoate (460 mg, 1.057 mmol, 109% yield) as a light brown gum. LCMS (System A, UV, ESI): $R_t$=1.12 min, [M+H]$^+$ 435+437

Intermediate 57: sodium (S)-(2-bromo-6-(3-ethylmorpholino)pyridin-4-yl)methanesulfinate

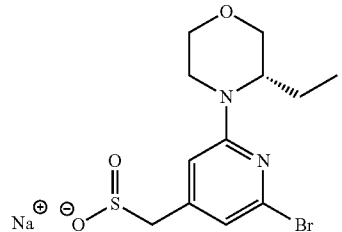 [SMILES: [Na+] ; CC[C@H]1COCCN1c1cc(CS(=O)[O-])cc(Br)n1]

Sodium methoxide (2 ml, 1.000 mmol) was added dropwise to Intermediate 56 methyl (S)-3-(((2-bromo-6-(3-ethylmorpholino)pyridin-4-yl)methyl)sulfonyl)propanoate (423 mg, 0.972 mmol) in Tetrahydrofuran (THF) (5 ml). After 5 mins at room temperature the reaction mixture was concentrated in vacuo to give (S)-(2-bromo-6-(3-ethylmorpholino)pyridin-4-yl)methanesulfinate, Sodium salt (443 mg, 1.193 mmol, 123% yield) as a brown gum. LCMS (System A, UV, ESI): $R_t$=0.7 min, [M+H]$^+$ 348+350

Intermediate 58: (S)-1-(2-bromo-6-(3-ethylmorpholino)pyridin-4-yl)-N,N-bis(4-methoxybenzyl)methanesulfonamide

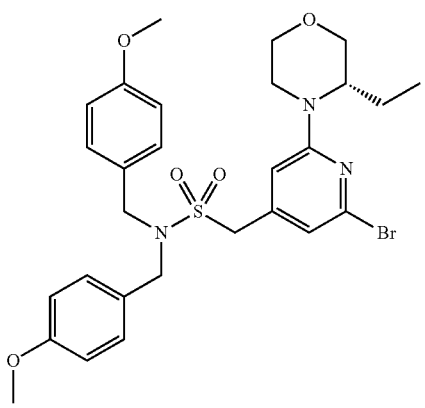 [SMILES: CC[C@H]1COCCN1c1cc(CS(=O)(=O)N(Cc2ccc(OC)cc2)Cc2ccc(OC)cc2)cc(Br)n1]

To iodine (79 mg, 0.311 mmol) in THF (1 mL) was added a solution of bis(4-methoxybenzyl)amine (305 mg, 1.185 mmol, Manchester Organics) and Intermediate 57 sodium (S)-(2-bromo-6-(3-ethylmorpholino)pyridin-4-yl)methanesulfinate (88 mg, 0.237 mmol) in THF (1 mL) and DMSO (0.4 mL). The reaction mixture was stirred at rt for 20 min and quenched with 5% sodium metabisulfite solution (1.5 mL), partitioned between water (5 mL) and EtOAc (5 mL), dried over a hydrophobic frit, and concentrated under a stream of nitrogen. The residue was purified by column chromatography and concentrated in vacuo to give (S)-1-(2-bromo-6-(3-ethylmorpholino)pyridin-4-yl)-N,N-bis(4-methoxybenzyl) methanesulfonamide (68 mg, 0.112 mmol, 47.4% yield) as a pale yellow gum. LCMS (System A, UV, ESI): $R_t$=1.48 min, [M+H]$^+$ 604+606

Intermediate 59: (S)-4-(2-bromo-6-(3-ethylmorpholino)pyridin-4-yl)-N,N-bis(4-methoxybenzyl)tetrahydro-2H-pyran-4-sulfonamide

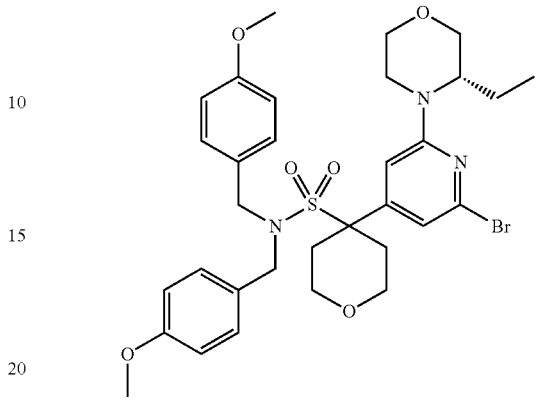

1-bromo-2-(2-bromoethoxy)ethane (0.014 ml, 0.111 mmol, Aldrich), and tetrabutylammonium bromide (4 mg, 0.012 mmol) and Intermediate 58(S)-1-(2-bromo-6-(3-ethylmorpholino)pyridin-4-yl)-N,N-bis(4-methoxybenzyl) methanesulfonamide (46 mg, 0.076 mmol) suspended in Toluene (1.5 ml) were treated with sodium hydroxide 50% in water (0.200 ml, 3.80 mmol). The reaction was stirred at room temperature for 4.5 h, then 60° C. for 16 h. The reaction mixture was partitioned between ethyl acetate (1.5 mL) and water (2 mL). The organic layer was separated, dried over a hydrophobic frit, and concentrated under a stream of nitrogen. The residue was purified by column chromatography and concentrated in vacuo to give (S)-4-(2-bromo-6-(3-ethylmorpholino)pyridin-4-yl)-N,N-bis(4-methoxybenzyl)tetrahydro-2H-pyran-4-sulfonamide (35 mg, 0.052 mmol, 68.2% yield) as a pale yellow gum. LCMS (System A, UV, ESI): $R_t$=1.47 min, [M+H]$^+$ 674+676

Similarly prepared to intermediate 59 from intermediate 57 were:

| Int | Structure | LCMS (System A, UV, ESI): |
|---|---|---|
| 60 | (S)-2-(2-bromo-6-(3-ethylmorpholino)pyridin-4-yl)-N,N-bis(4-ethoxybenzyl)propane-2-Sulfonamide | $R_t$ = 1.57 min, [M + H]$^+$ 632 + 634 |

-continued

| Int | Structure | LCMS (System A, UV, ESI): |
|---|---|---|
| 61 | (S)-1-(2-bromo-6-(3-ethylmorpholino)pyridin-4-yl)-N-ethyl-methanesulfonamide | $R_t$ = 1.13 min, $[M + H]^+$ 392 + 394 |
| 62 | (S)-1-(2-bromo-6-(3-ethylmorpholino)pyridin-4-yl)-N-(4-methoxy-benzyl)-N-methylmethanesulfonamide | $R_t$ = 1.33 min, $[M + H]^+$ 498 + 500 |
| 63 | (S)-4-(2-bromo-6-(3-ethylmorpholino)pyridin-4-yl)-N,N-dimethyltetrahydro-2H-pyran-4-sulfonamide | $R_t$ = 1.33 min, $[M + H]^+$ 462 + 464 |
| 64 | (S)-1-(2-bromo-6-(3-ethylmorpholino)pyridin-4-yl)-N-(4-methoxybenzyl)methanesulfonamide | $R_t$ = 1.24 min, $[M + H]^+$ 484 + 486 |

| Int | Structure | LCMS (System A, UV, ESI): |
|---|---|---|
| 65 | ![structure]<br>tert-butyl (S)-(((2-bromo-6-(3-ethylmorpholino)pyridin-4-yl)methyl)sulfonyl)glycinate | $R_t$ = 1.27 min, $[M + H]^+$ 478 + 480 |
| 66 | ![structure]<br>(S)-1-(2-bromo-6-(3-ethylmorpholino)pyridin-4-yl)-N,N-dimethylmethanesulfonamide | $R_t$ = 1.13 min, $[M + H]^+$ 392 + 394 |

Intermediate 67: tert-butyl ((5-bromo-1H-pyrrolo[3,2-b]pyridin-2-yl)methyl)(methyl)carbamate

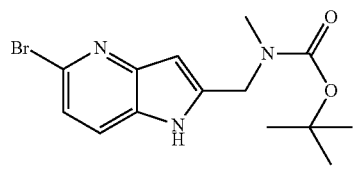 [SMILES: CN(Cc1cc2nc(Br)ccc2[nH]1)C(=O)OC(C)(C)C]

A mixture of 2,6-dibromopyridin-3-amine (0.50 g, 1.985 mmol, Manchester Organics), tert-butyl methyl(prop-2-yn-1-yl)carbamate Intermediate 11 (0.403 g, 2.382 mmol), pyrrolidine (1.641 ml, 19.85 mmol) and bis(triphenylphosphine)palladium(II) chloride (0.070 g, 0.099 mmol) was stirred at room temperature under nitrogen for 5 hours and then at 60 C for 18 hours. The solvent was removed in vacuo. The residue was dissolved in DCM and applied to a 120 g silica cartridge. This was eluted with a gradient of 0-100% ethyl acetate in cyclohexane over 30 minutes. The required fractions were combined and evaporated in vacuo to give tert-butyl ((5-bromo-1H-pyrrolo[3,2-b]pyridin-2-yl)methyl)(methyl)carbamate (515 mg) as a brown oil. LCMS (System B, UV, ESI): $R_t$=1.0 5 min, $[M+H]^+$ 340+342

Intermediate 68: methyl 3-((2-(((tert-butoxycarbonyl)(methyl)amino)methyl)-1H-pyrrolo[3,2-b]pyridin-5-yl)sulfonyl)propanoate

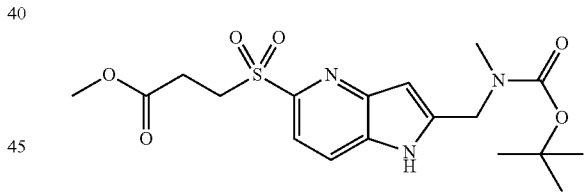

A solution of Intermediate 67 tert-butyl ((5-bromo-1H-pyrrolo[3,2-b]pyridin-2-yl)methyl)(methyl)carbamate (1.1912 g, 3.50 mmol), sodium 3-methoxy-3-oxopropane-1-sulfinate (1.224 g, 7.03 mmol, Aldrich) and copper(I) iodide (1.34 g, 7.04 mmol) in Dimethyl Sulfoxide (DMSO) (18 ml) was degassed for 10 minutes under a flow of nitrogen. The reaction vessel was heated to 110° C. and stirred at 110° C. under nitrogen for 2 h. Ethyl acetate (30 ml) was added to the reaction mixture, which was then filtered on Celite (10 g) and the residual solid washed with ethyl acetate (3×20 ml). The filtrate was washed with a mixture of water/aqueous saturated ammonium chloride/aqueous saturated sodium bicarbonate (4:1:1 60 ml), and water (60 ml). The aqueous layer was further extracted with ethyl acetate (50 ml) and the organic phases combined. The organic phase was further washed with a mixture of water/aqueous saturated ammonium chloride/aqueous saturated sodium bicarbonate (4:1:160 ml), and water (60 ml), followed by brine (50 ml), dried over magnesium sulfate and concentrated under reduced pressure to yield methyl 3-((2-(((tertbutoxycarbonyl)(methyl)amino)methyl)-1H-pyrrolo[3,2-b]pyridin-5-I)sulfonyl)-propanoate (1380 mg, 3.35 mmol, 96% yield). LCMS (System B, UV, ESI): $R_f$=0.92 min, [M+H]$^+$ 412

Intermediate 69: Sodium 2-(((tert-butoxycarbonyl)(methyl)amino)methyl)-1H-pyrrolo[3,2-b]pyridine-5-sulfinate

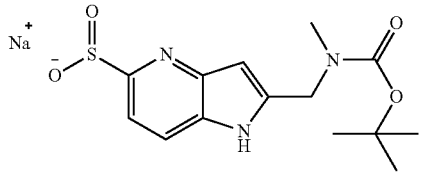 [SMILES: [Na+] ; CN(Cc1cc2nc(S(=O)[O-])ccc2[nH]1)C(=O)OC(C)(C)C]

sodium methoxide (0.5 M in Methanol) (10 mL, 5.00 mmol) was added dropwise to a solution of Intermediate 68 methyl 3-((2-(((tert-butoxycarbonyl)(methyl)amino)methyl)-1H-pyrrolo[3,2-b]pyridin-5-yl)sulfonyl)propanoate Intermediate 47 (1.99 g, 4.84 mmol) in Tetrahydrofuran (THF) (5 mL) under nitrogen. The reaction mixture was stirred under nitrogen at RT for 2.5 h. The reaction mixture was concentrated under reduced pressure to give 2-(((tert-butoxycarbonyl)(methyl)-amino)methyl)-1H-pyrrolo[3,2-b]pyridine-5-sulfinate, Sodium salt (1751.4 mg, 4.79 mmol, 99% yield). LCMS (System B, UV, ESI): $R_f$=0.60 min, [M+H]$^+$ 326

Intermediate 70 Route B: (S)-5-(6-(3-ethylmorpholino)-4-(2-(methylsulfonyl)propan-2-yl)pyridin-2-yl)-1H-pyrrolo[3,2-b]pyridine-2-carboxylate

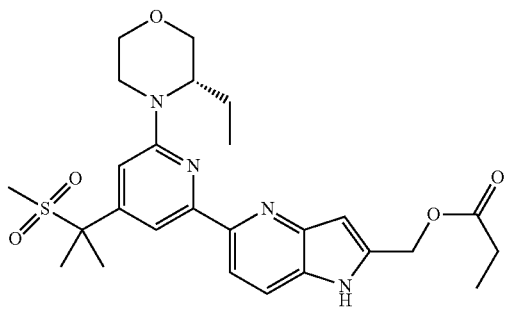 [SMILES: CCC(=O)OCc1cc2nc(-c3cc(C(C)(C)S(C)(=O)=O)cc(N4CCOC[C@@H]4CC)n3)ccc2[nH]1]

A mixture of Intermediate 14 (S)-3-ethyl-4-(4-(2-(methylsulfonyl)propan-2-yl)-6-(trimethylstannyl)pyridin-2-yl)morpholine (100 mg, 0.210 mmol), ethyl 5-chloro-1H-pyrrolo[3,2-b]pyridine-2-carboxylate (70.9 mg, 0.316 mmol, Activate Scientific), PdCl2(dppf) (15.40 mg, 0.021 mmol) and lithium chloride (8.92 mg, 0.210 mmol) in dry Toluene (2000 µl) was degassed under a flow of nitrogen for 5 min, sealed and heated to 100° C. for 20 h. The reaction mixture was cooled down to RT, EtOAc (3 mL) and the resulting mixture was filtered through a silica cartridge (1 g). The residual solid was washed with EtOAc (2×10 mL) and MeOH (2×5 mL). The filtrate was washed with aqueous potassium fluoride solution (1M, 2×20 mL), brine (30 mL) and dried over MgSO4. The volatiles were removed under reduced pressure to give a residue that was purified by column chromatography to give ethyl (S)-5-(6-(3-ethylmorpholino)-4-(2-(methylsulfonyl)propan-2-yl)pyridin-2-yl)-1H-pyrrolo[3,2-b]pyridine-2-carboxylate (40 mg, 0.080 mmol, 38.0% yield) as a colourless solid. LCMS (System B, UV, ESI): $R_f$=0.93 min, [M+H]$^+$ 501

Intermediate 71 Route C; ethyl (S)-5-(6-(3-ethylmorpholino)-4-(4-(methylsulfonyl)tetrahydro-2H-pyran-4-yl)pyridin-2-yl)-1H-pyrrolo[3,2-b]pyridine-2-carboxylate

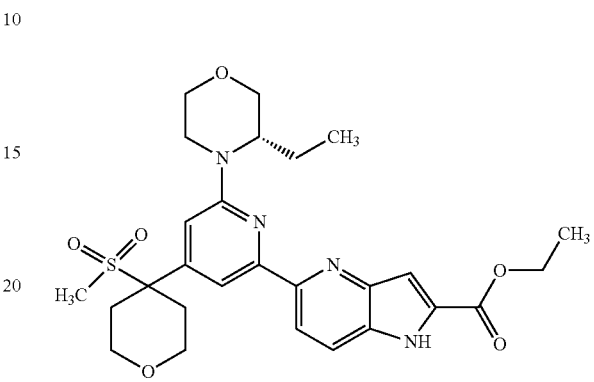

Intermediate 43 sodium (S)-6-(3-ethylmorpholino)-4-(4-(methylsulfonyl)tetrahydro-2H-pyran-4-yl)pyridine-2-sulfinate (127 mg, 0.245 mmol), palladium(II) acetate (5.01 mg, 0.022 mmol), tricyclohexylphosphine (12.51 mg, 0.045 mmol), ethyl 5-bromo-1H-pyrrolo[3,2-b]pyridine-2-carboxylate (60 mg, 0.223 mmol, Advanced Chemblocks) and K2CO3 (46.2 mg, 0.334 mmol) were placed in dry 1,4-Dioxane (2500 µl) and the resulting mixture was degassed under a flow of nitrogen for 5 min, sealed, and heated to 150° C. for 14 h. The reaction mixture was cooled down and filtered through a Celite cartridge (2.5 g) and eluted with EtOAc (20 mL). The resulting solution was concentrated under reduced pressure to give a residue that was purified by column chromatography on silica using the elution gradient EtOAc in Cyclohexane 0-100%, to give ethyl (S)-5-(6-(3-ethylmorpholino)-4-(4-(methylsulfonyl)tetrahydro-2H-pyran-4-yl)pyridin-2-yl)-1H-pyrrolo[3,2-b]pyridine-2-carboxylate (95 mg, 0.175 mmol, 79% yield) as a off-white solid. LCMS (System B, UV, ESI): $R_f$=0.88 min, [M+H]$^+$ 543

Intermediate 72 5-bromo-2-(((tert-butyldimethylsilyl)oxy)methyl)-1H-pyrrolo[3,2-b]pyridine

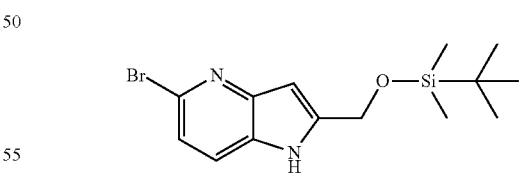

A mixture of 2,6-dibromopyridin-3-amine (2001 mg, 7.94 mmol, Apollo), tert-butyldimethyl(prop-2-yn-1-yloxy)silane (1627 mg, 9.55 mmol, Aldrich), pyrrolidine (3300 µl, 39.9 mmol) and bis(triphenylphosphine)palladium(II) chloride (280 mg, 0.399 mmol) was placed in a sealed MW vial, stirred and heated at 60° C. for 3 h. The reaction mixture was partitioned between EtOAc (100 mL) and saturated ammonium chloride solution (100 mL). The organic layer was separated, dried over a hydrophobic frit, and concentrated under reduced pressure. The residue was purified by column chromatography (KP-NH and silica) to give 5-bromo-2-

(((tertbutyldimethylsilyl)oxy)methyl)-1H-pyrrolo[3,2-b] pyridine (623 mg, 1.825 mmol, 22.98% yield) as an off-white solid. LCMS (System A, UV, ESI): $R_t$=1.39 min, [M+H]$^+$ 341 & 343

Intermediate 73 tert-butyl (S)-4-(2-(3-ethylmorpholino)-6-((3-methoxy-3-oxopropyl)sulfonyl) pyridin-4-yl)-4-(methylsulfonyl)piperidine-1-carboxylate

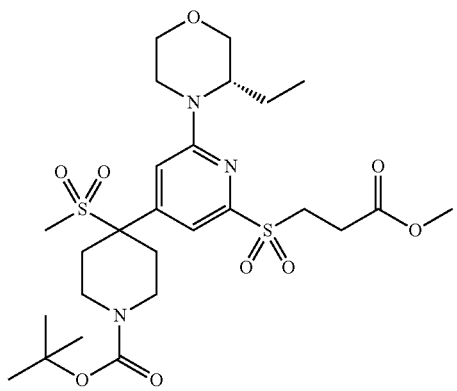 [SMILES: CC[C@H]1COCCN1c1cc(C2(S(C)(=O)=O)CCN(C(=O)OC(C)(C)C)CC2)cc(S(=O)(=O)CCC(=O)OC)n1]

sodium 3-methoxy-3-oxopropane-1-sulfinate (107 mg, 0.616 mmol, Aldrich), copper(I) iodide (117 mg, 0.616 mmol), Intermediate 48 tert-butyl (S)-4-(2-bromo-6-(3-ethylmorpholino)pyridin-4-yl)-4-(methylsulfonyl)piperidine-1-carboxylate (164 mg, 0.308 mmol) were placed in Dimethyl Sulfoxide (DMSO) (2500 µl) and the resulting mixture was degassed under a flow of nitrogen for 5 min, sealed and heated to 110° C. for 2 h. EtOAc (80 mL) was added to the cooled reaction mixture and the resulting mixture was washed with water:saturated ammonium chloride:saturated sodium bicarbonate (1:1:1, 2×90 mL), brine (30 mL) and dried over MgSO4. The volatiles were removed under reduced pressure to give a residue that was purified by column chromatography to give tert-butyl (S)-4-(2-(3-ethylmorpholino)-6-((3-methoxy-3-oxopropyl)sulfonyl)pyridin-4-yl)-4-(methylsulfonyl)piperidine-1-carboxylate (150 mg, 0.248 mmol, 81% yield). LCMS (System B, UV, ESI): $R_t$=1.08 min, [M+H]$^+$ 604

Intermediate 74 (S)-4-(1-(tertbutoxycarbonyl)-4-(methylsulfonyl)piperidin-4-yl)-6-(3-ethylmorpholino)pyridine-2-sulfinate, Sodium Salt

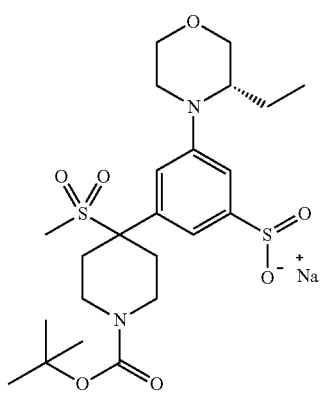 [SMILES: CC[C@H]1COCCN1c1cc(S(=O)[O-])cc(C2(S(C)(=O)=O)CCN(C(=O)OC(C)(C)C)CC2)c1 ; [Na+]]

sodium methoxide (522 µl, 0.261 mmol) was added at ambient temperature to a solution of Intermediate 73 tert-butyl (S)-4-(2-(3-ethylmorpholino)-6-((3-methoxy-3-oxopropyl)sulfonyl)pyridin-4-yl)-4-(methylsulfonyl)piperidine-1-carboxylate (150 mg, 0.248 mmol) in Tetrahydrofuran (THF) (2000 µl) under an atmosphere of nitrogen. The resulting solution was stirred for 20 min.

The volatiles were removed under reduced pressure to give (S)-4-(1-(tert-butoxycarbonyl)-4-(methylsulfonyl)piperidin-4-yl)-6-(3-ethylmorpholino)pyridine-2-sulfinate, Sodium salt (131 mg, 0.243 mmol, 98% yield) as an off-white solid. LCMS (System B, UV, ESI): $R_t$=1.08 min, [M+H]$^+$ 516 & 518

Intermediate 75 tert-butyl 4-{2-[(3S)-3-ethylmorpholin-4-yl]-6-[2-(hydroxymethyl)-1H-pyrrolo[3,2-b]pyridin-5-yl]pyridin-4-yl}-4-methanesulfonylpiperidine-1-carboxylate

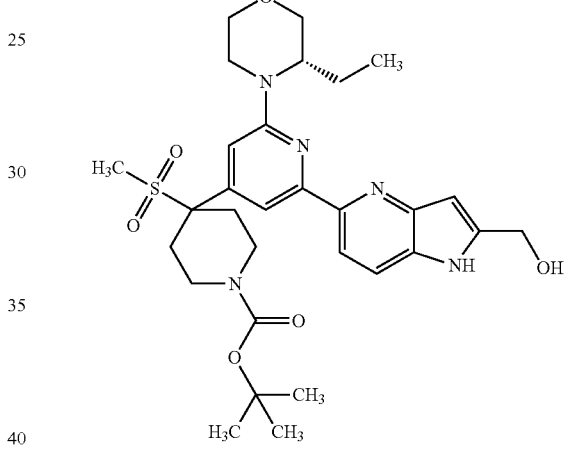

A mixture of Intermediate 74 sodium (S)-4-(1-(tert-butoxycarbonyl)-4-(methylsulfonyl)piperidin-4-yl)-6-(3-ethylmorpholino)pyridine-2-sulfinate (65 mg, 0.120 mmol), Intermediate 73 5-bromo-2-(((tertbutyldimethylsilyl)oxy)methyl)-1H-pyrrolo[3,2-b]pyridine (49.3 mg, 0.145 mmol), K2CO3 (33.3 mg, 0.241 mmol), palladium(II) acetate (2.70 mg, 0.012 mmol) in dry 1,4-Dioxane (1300 µl) was degassed under a flow of nitrogen for 5 min. The resulting mixture was sealed and heated to 150° C. for 17 h. The mixture was cooled and filtered through a Celite cartridge (2.5 g) eluting with EtOAc (3×10 mL). The filtrate was collected and the volatiles removed under reduced pressure to give a residue that was dissolved in Tetrahydrofuran (THF) (3000 µl):HCl (aqueous) (500 µl, 1.000 mmol) and stirred for 35 min. Ammonium chloride saturated solution (3 mL) was added and the resulting mixture was extracted with DCM (2×10 mL) The organic phases were combined and the volatiles reduced under reduced pressure to give a residue that was purified by reverse phase chromatography using the elution gradient acetonitrile in water 15-55% (formic acid modifier) to give tert-butyl (S)-4-(2-(3-ethylmorpholino)-6-(2-(hydroxymethyl)-1Hpyrrolo[3,2-b]pyridin-5-yl)pyridin-4-yl)-4-(methylsulfonyl)piperidine-1-carboxylate (33 mg, 0.055 mmol, 45.7% yield) as a colourless solid. LCMS (System B, UV, ESI): $R_t$=0.75 min, [M+H]$^+$ 600

Similarly prepared to intermediate 41 from intermediate 1 was:

Intermediate 76: 2,6-dichloro-4-(4-methanesulfonyloxan-4-yl)pyridine

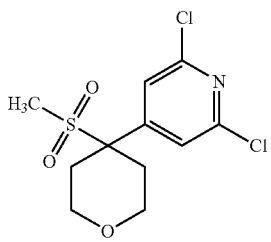

R$_r$ = 1.06 min, [M+H]$^+$ 310

Similarly prepared to intermediate 49 from intermediate 76 was:

Intermediate 77: 3-[6-chloro-4-(4-methanesulfonyloxan-4-yl)pyridin-2-yl]-8-oxa-3-azabicyclo[3.2.1]octane

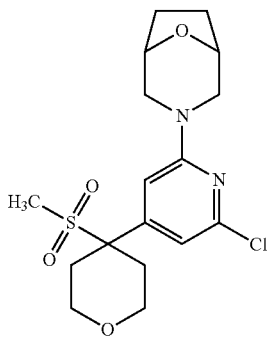

R$_r$ = 0.90 min, [M+H]$^+$ 387

EXAMPLES

Example 1 [(5-{6-[(3S)-3-ethylmorpholin-4-yl]-4-(2-methanesulfonylpropan-2-yl)pyridin-2-yl}-1H-pyrrolo[3,2-b]pyridin-2-yl)methyl](methyl)amine

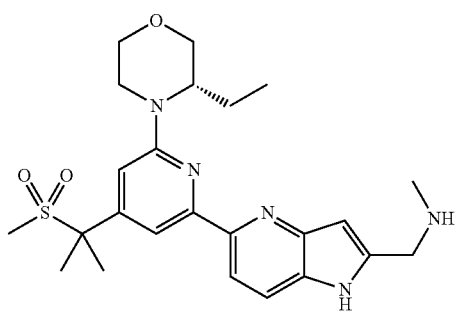

tert-butyl (S)-((5-(6-(3-ethylmorpholino)-4-(2-(methylsulfonyl)propan-2-yl)pyridin-2-yl)-1-(phenylsulfonyl)-1H-pyrrolo[3,2-b]pyridin-2-yl)methyl)(methyl)carbamate (the compound of Intermediate 10, 770 mg, 0.887 mmol), methanamine 2M in THF (1.3 mL, 2.60 mmol, Aldrich) and 2M sodium hydroxide (2.2 mL, 4.40 mmol) were combined in anhydrous Tetrahydrofuran (THF) (4.00 mL) and anhydrous Methanol (2 mL) and stirred at 21 C under nitrogen for 2 hr. Saturated aqueous ammonium chloride (20 mL) was added and the reaction mixture extracted with DCM (2×20 mL). The organic layers were concentrated in vacuo and the residue redissolved in 1,4-Dioxane (3 mL), 4 M HCl in dioxane (3.3 mL, 13.20 mmol) was added and the reaction mixture was stirred at 21 C for 1 hr.

The mixture was concentrated in vacuo and under nitrogen, then redissolved in methanol (10 mL) and loaded onto a aminopropyl (NH2) SPE (50 g, primed with methanol (1 CV), eluting with methanol (3 CV). Appropriate fractions concentrated in vacuo to give 560 mg of a brown residue.

The residue was taken in minimal DCM and purified by flash chromatography. The crude compound was taken in methanol and purified by reverse phase chromatography to give [(5-{6-[(3S)-3-ethylmorpholin-4-yl]-4-(2-methanesulfonylpropan-2-yl)pyridin-2-yl}-1H-pyrrolo[3,2-b]pyridin-2-yl)methyl](methyl)amine. Trituration with TBME followed by concentration from EtOH and drying in the drying pistol gave (S)-1-(5-(6-(3-ethylmorpholino)-4-(2-(methylsulfonyl)propan-2-yl)pyridin-2-yl)-1H-pyrrolo[3,2-b]pyridin-2-yl)-N-methylmethanamine (111 mg, 0.228 mmol, 25.7% yield) as an off white solid.

1H NMR (400 MHz, DMSO-d6) δ ppm 0.91 (t, J=7.5 Hz, 3H), 1.47-1.67 (m, 1H), 1.74-1.87 (m, 7H), 2.33 (s, 3H), 2.78 (s, 3H), 3.15 (td, J=12.6, 3.7 Hz, 1H), 3.54 (td, J=11.7, 2.9 Hz, 1H), 3.61 (dd, J=11.4, 2.8 Hz, 1H), 3.84 (s, 2H), 3.92 (d, J=11.5 Hz, 1H), 3.97 (brdd, J=11.1, 3.1 Hz, 1H), 4.11 (brd, J=12.0 Hz, 1H), 4.22 (brs, 1H), 6.48 (s, 1H), 6.85 (s, 1H), 7.74

(d, J=8.6 Hz, 1H), 7.93 (br d, J=1.0 Hz, 1H), 8.12 (d, J=8.6 Hz, 1H), 11.23 (br s, 1H). NHMe NH missing 13C NMR (101 MHz, DMSO-d6) δ ppm 11.1 (s, 1C), 19.6 (s, 1C), 21.8 (s, 1C), 21.8 (s, 1C), 34.9 (s, 1C), 35.5 (s, 1C), 40.5 (s, 1C), 48.4 (s, 1C), 52.8 (s, 1C), 63.9 (s, 1C), 66.2 (s, 1C), 67.3 (s, 1C), 100.1 (s, 1C), 105.1 (s, 1C), 107.9 (s, 1C), 113.5 (s, 1C), 118.0 (s, 1C), 129.0 (s, 1C), 143.7 (s, 1C), 146.1 (s, 1C), 148.5 (s, 2C), 155.0 (s, 1C), 157.9 (s, 1C).

LCMS (System B, UV, ESI): Rt=0.44 min, [M+H]+ 471.34.

The trifluoroacetic acid salt of this compound has also been prepared, using methods standard in the art.

Similarly prepared to Example 1 from the compound of Intermediate 9 and the intermediates above were:

| Example | Compound | Int | NMR | LCMS (System B, UV, ESI): | MDAP |
|---|---|---|---|---|---|
| 2 | 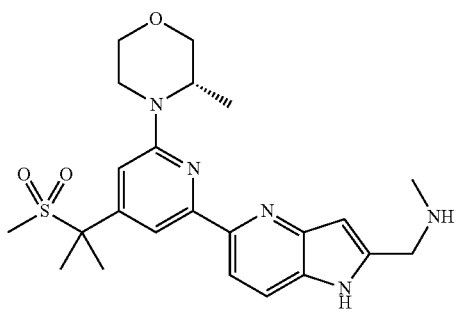<br>(S)-N-methyl-1-(5-(6-(3-methylmorpholino)-4-(2-(methylsulfonyl)propan-2-yl)pyridin-2-yl)-1H-pyrrolo[3,2-b]pyridin-2-yl)methanamine | 16 | 1H NMR (400 MHz, DMSO-d6) δ ppm 11.24 (1H, br. s.), 8.13 (1H, d, J = 8.6 Hz), 7.97 (1H, d), 7.75 (1H, d), 6.87 (1H, d, J = 1.0 Hz), 6.49 (1H, s), 4.47 (1H, d, J = 6.6 Hz), 3.95-4.16 (2H, m), 3.67-3.90 (4H, m), 3.50-3.63 (1H, m), 3.12-3.23 (1H, m), 2.80 (3H, s), 2.33 (3H, s), 1.81 (6H, d, J = 1.7 Hz), 1.19 (3H, d, J = 6.6 Hz) | $R_t$ = 0.44 min, $[M + H]^+$ 458 | HpH_MethC |
| 3 | 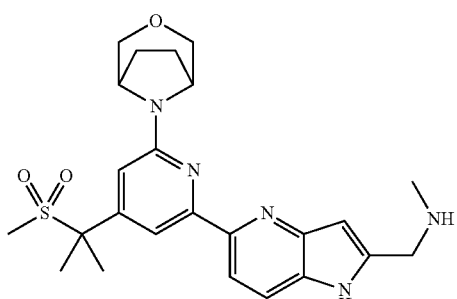<br>1-(5-(6-((1R,5S)-3-oxa-8-azabicyclo[3.2.1]octan-8-yl)-4-(2-(methylsulfonyl)propan-2-yl)pyridin-2-yl)-1H-pyrrolo[3,2-b]pyridin-2-yl)-N-methylmethanamine | 17 | $^1$H NMR (400 MHz, DMSO-$d_6$) δ ppm 1.81 (s, 6 H) 1.87-2.06 (m, 4 H) 2.34 (s, 3 H) 2.81 (s, 3 H) 3.59 (d, J = 10.51 Hz, 2 H) 3.74 (d, J = 10.51 Hz, 2 H) 3.85 (s, 2 H) 4.65 (br. s., 2 H) 6.50 (s, 1 H) 6.91 (d, J = 1.22 Hz, 1 H) 7.74 (dd, J = 8.56, 0.73 Hz, 1 H) 7.96 (d, J = 1.47 Hz, 1H) 8.12 (d, J = 8.56 Hz, 1 H) 11.26 (br. s., 1 H) | $R_t$ = 0.45 min, $[M + H]^+$ 470 | HpH_Ext_MethC |
| 4 | 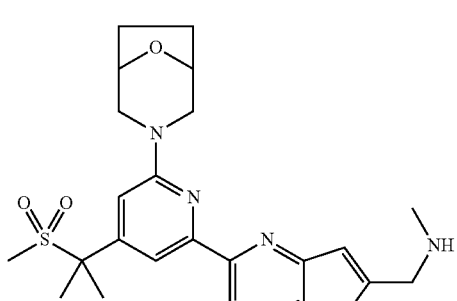<br>1-(5-(6-(8-oxa-3-azabicyclo[3.2.1]octan-3-yl)-4-(2-(methylsulfonyl)propan-2-yl)pyridin-2-yl)-1H-pyrrolo[3,2-b]pyridin-2-yl)-N-methylmethanamine | 18 | $^1$H NMR (400 MHz, DMSO-$d_6$) δ ppm 1.76-1.94 (m, 10 H) 2.34 (s, 3 H) 2.81 (s, 3 H) 3.05 (dd, J = 12.23, 2.20 Hz, 2 H) 3.85 (s, 2 H) 4.01 (d, J = 11.98 Hz, 2 H) 4.50 (br. s., 2 H) 6.49 (s, 1 H) 6.82 (d, J = 0.98 Hz, 1 H) 7.75 (dd, J = 8.56, 0.73 Hz, 1 H) 7.99 (d, J = 0.98 Hz, 1 H) 8.14 (d, J = 8.56 Hz, 1 H) 11.27 (br. s., 1 H) | $R_t$ = 0.45 min, $[M + H]^+$ 470 | HpH_Ext_MethC |

| Example | Compound | Int | NMR | LCMS (System B, UV, ESI): | MDAP |
|---|---|---|---|---|---|
| 5 | 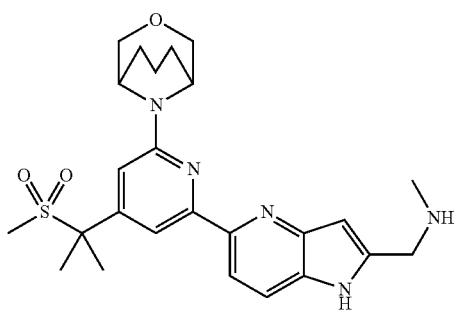<br>1-(5-(6-(3-oxa-9-azabicyclo[3.3.1]nonan-9-yl)-4-(2-(methylsulfonyl)propan-2-yl)pyridin-2-yl)-1H-pyrrolo[3,2-b]pyridin-2-yl)-N-methylmethanamine | 19 | $^1$H NMR (400 MHz, CHLOROFORM-d) δ ppm 1.68 (br. s., 2 H) 1.85 (dd, J = 13.45, 5.62 Hz, 2 H) 1.93 (s, 6 H) 1.98-2.12 (m, 2 H) 2.52 (s, 3 H) 2.60-2.71 (m, 2 H) 3.96-4.14 (m, 6 H) 4.45 (br. s., 2 H) 6.63 (s, 1 H) 6.99 (d, J = 1.22 Hz, 1 H) 7.66-7.75 (m, 1 H) 8.00 (d, J = 1.22 Hz, 1 H) 8.22 (d, J = 8.56 Hz, 1 H) 8.86 (br. s., 1 H) | $R_t$ = 0.46 min, [M + H]$^+$ 484 | N/A XBridge Prep C18 OBD Column, 30-85% acetonitrile in aqueous ammonium bicarbonate |
| 6 | 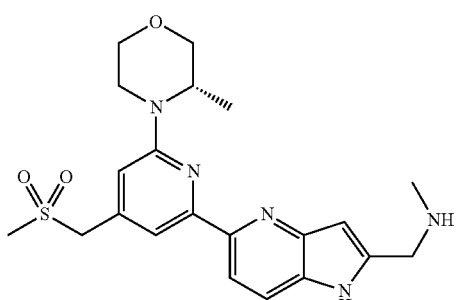<br>(S)-N-methyl-1-(5-(6-(3-methylmorpholino)-4-((methylsulfonyl)methyl)pyridin-2-yl)-1H-pyrrolo[3,2-b]pyridin-2-yl)methanamine | 20 | 1H NMR (400 MHz, DMSO-d6) δ ppm 11.25 (1H, br. s.), 8.13 (1H, d, J = 8.6 Hz), 7.83 (1H, s), 7.68-7.78 (1H, m), 6.77 (1H, s), 6.46 (1H, s), 4.54 (2H, s), 4.35-4.45 (1H, m), 3.96-4.08 (2H, m), 3.67-3.88 (4H, m), 3.56 (1H, td, J = 11.7 Hz, J = 2.9 Hz), 3.08-3.21 (1H, m), 2.99 (3H, s), 2.27-2.36 (3H, m), 1.20 (3H, d, J = 6.8 Hz) | $R_t$ = 0.37 min, [M + H]$^+$ 430 | HpH_MethB |
| 7 | 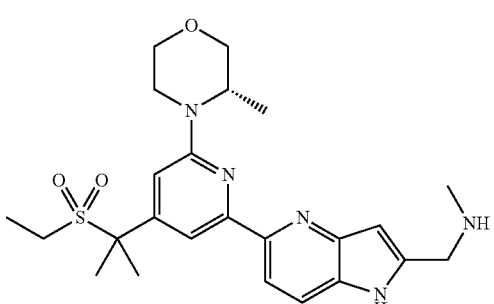<br>(S)-N-methyl-1-(5-(6-(3-(S)-1-(5-(4-(2-(ethylsulfonyl)propan-2-yl)-6-(3-methylmorpholino)pyridin-2-yl)-1H-pyrrolo[3,2-b]pyridin-2-yl)-N-methylmethanamine | 21 | $^1$H NMR (400 MHz, CHLOROFORM-d) δ ppm 1.32 (d, J = 6.85 Hz, 3 H) 1.93 (S, 3 H) 2.52 (s, 3 H) 2.78 (qd, J = 7.54, 2.32 Hz, 2 H) 3.33 (td, J = 12.65, 3.79 Hz, 1 H) 3.71 (td, J = 11.62, 2.69 Hz, 1 H) 3.86 (d, J = 1.96 Hz, 2 H) 4.03 (s, 2 H) 4.06-4.17 (m, 2 H) 4.42-4.54 (m, 1 H) 6.62 (s, 1 H) 6.99 (d, J = 1.22 Hz, 1 H) 7.70 (dd, J = 8.56, 0.73 Hz, 1 H) 8.05 (d, J = 1.22 Hz, 1 H) 8.25 (d, J = 8.56 Hz, 1 H) 8.75 (br. s., 1 H) | $R_t$ = 0.43 min, [M + H]$^+$ 472 | HpH_MethC |

| Example | Compound | Int | NMR | LCMS (System B, UV, ESI): | MDAP |
|---|---|---|---|---|---|
| 8 | 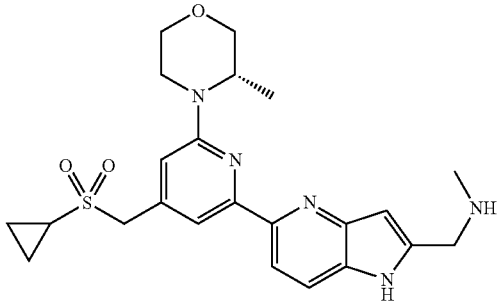<br>(S)-1-(5-(4-((cyclopropylsulfonyl)methyl)-6-(3-methylmorpholino)pyridin-2-yl)-1H-pyrrolo[3,2-b]pyridin-2-yl)-N-methylmethanamine | 24 | $^1$H NMR (400 MHz, CHLOROFORM-d) δ ppm 0.82-0.93 (m, 2 H) 1.00-1.15 (m, 2 H) 1.32 (d, J = 6.85 Hz, 3 H) 2.12-2.26 (m, 1 H) 2.52 (s, 3 H) 3.26-3.41 (m, 1 H) 3.71 (td, J = 11.74, 3.18 Hz, 1 H) 3.87 (d, J = 1.96 Hz, 2 H) 4.00-4.15 (m & s, 4 H) 4.49 (d, J = 6.85 Hz, 1 H) 6.62 (s, 1 H) 6.98 (d, J = 1.22 Hz, 1 H) 7.69 (dd, J = 8.56, 0.73 Hz, 1H) 8.13 (d, J = 1.22 Hz, 1 H) 8.24 (s, 1 H) 8.62-8.73 (m, 1 H) | R$_t$ = 0.45 min, [M + H]$^+$ 484 | HpH_Ext_MethC |
| 9 | 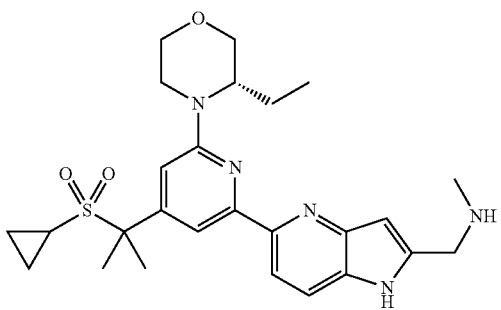<br>(S)-1-(5-(4-(2-(cyclopropylsulfonyl)propan-2-yl)-6-(3-ethylmorpholino)pyridin-2-yl)-1H-pyrrolo[3,2-b]pyridin-2-yl)-N-methylmethanamine | 25 | $^1$H NMR (400 MHz, CHLOROFORM-d) δ ppm 0.78-0.92 (m, 2 H) 1.00 (t, J = 7.46 Hz, 3 H) 1.02-1.11 (m, 2 H) 1.88-2.04 (m, 6 H) 2.18 (tt, J = 8.07, 4.89 Hz, 1 H) 2.52 (s, 3 H) 3.32 (td, J = 12.59, 3.91 Hz, 1 H) 3.63-3.81 (m, 2 H) 3.97-4.16 (m, 5 H) 4.21 (d, J = 4.16 Hz, 1H) 6.62 (s, 1 H) 6.96 (d, J = 1.47 Hz, 1 H) 7.69 (dd, J = 8.56, 0.73 Hz, 1 H) 8.10 (d, J = 1.22 Hz, 1 H) 8.24 (d, J = 8.56 Hz, 1 H) 8.76 (br. s., 1 H) | R$_t$ = 0.49 min, [M + H]$^+$ 498 | XBridge Prep C18 OBD column, 30-75% acetonitrile in aqueous ammonium bicarbonate |
| 10 | 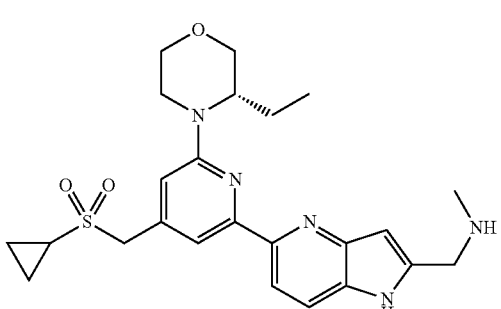<br>(S)-1-(5-(4-((cyclopropylsulfonyl)methyl)-6-(3-ethylmorpholino)pyridin-2-yl)-1H-pyrrolo[3,2-b]pyridin-2-yl)-N-methylmethanamine | 26 | $^1$H NMR (400 MHz, CHLOROFORM-d) δ ppm 0.93-1.07 (m, 2 + 3 H) 1.17-1.28 (m, 2 H) 1.53-1.79 (m, 1 H) 1.96 (ddd, J = 13.57, 9.17, 7.34 Hz, 1 H) 2.36 (tt, J = 8.01, 4.71 Hz, 1 H) 2.52 (s, 3 H) 3.33 (td, J = 12.65, 3.79 Hz, 1 H) 3.63-3.78 (m, 2 H) 3.99-4.08 (m, 4 H) 4.13 (d, J = 10.76 Hz, 1 H) 4.23 (br. s., 1 H) 4.30 (s, 2 H) 6.61 (s, 1 H) 6.70 (s, 1 H) 7.67-7.72 (m, 1 H) 7.86 (d, J = 0.73 Hz, 1 H) 8.24 (d, J = 8.56 Hz, 1 H) 8.73 (br. s., 1 H) | R$_t$ = 0.43 min, [M + H]$^+$ 470 | HpH_Ext_MethC |

-continued

| Example | Compound | Int | NMR | LCMS (System B, UV, ESI): | MDAP |
|---|---|---|---|---|---|
| 11 | 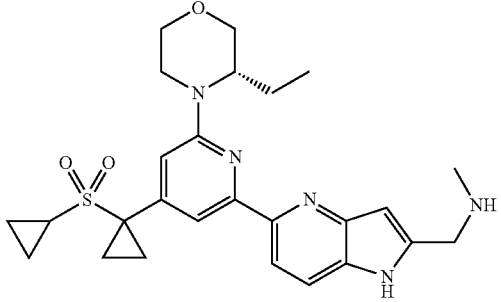<br>(S)-1-(5-(4-(1-(cyclopropylsulfonyl)cyclopropyl)-6-(3-ethylmorpholino)pyridin-2-yl)-1H-pyrrolo[3,2-b]pyridin-2-yl)-N-methylmethanamine | 27 | $^1$H NMR (400 MHz, CHLOROFORM-d) δ ppm 0.91 (dd, J = 8.31, 0.98 Hz, 2 H) 0.99 (t, J = 7.46 Hz, 3 H) 1.02-1.12 (m, 2 H) 1.32-1.48 (m, 2 H) 1.59-1.77 (m, 1 H) 1.79-1.87 (m, 2 H) 1.87-2.02 (m, 1 H) 2.32-2.44 (m, 1 H) 2.50 (s, 3 H) 3.31 (td, J = 12.59, 3.67 Hz, 1 H) 3.60-3.80 (m, 2 H) 3.95-4.16 (m, 2 + 3 H) 4.23 (br. s., 1 H) 6.61 (s, 1 H) 6.89 (s, 1 H) 7.68 (d, J = 8.56 Hz, 1 H) 7.99 (d, J = 0.98 Hz, 1 H) 8.23 (d, J = 8.56 Hz, 1 H) 9.11 (br. s., 1H) | $R_t$ = 1.02 min, $[M + H]^+$ 496 | XBridge Prep C18 OBD column 20-60% acetonitrile in aqueous ammonium bicarbonate |
| 12 | 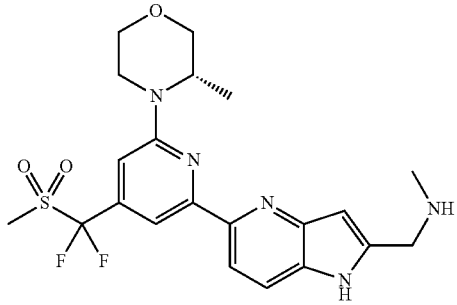<br>(S)-1-(5-(4-(difluoro(methylsulfonyl)methyl)-6-(3-methylmorpholino)pyridin-2-yl)-1H-pyrrolo[3,2-b]pyridin-2-yl)-N-methylmethanamine | 28 | $^1$H NMR (400 MHz, CHLOROFORM-d) δ ppm 1.35 (d, J = 6.60 Hz, 3 H) 2.51 (s, 3 H) 3.15 (s, 3 H) 3.36 (td, J = 12.59, 3.91 Hz, 1 H) 3.69 (td, J = 11.62, 2.69 Hz, 1 H) 3.79-3.93 (m, 2 H) 4.01 (s, 2 H) 4.05-4.16 (m, 2 H) 4.48 (d, J = 6.85 Hz, 1 H) 6.62 (s, 1 H) 6.79 (s, 1 H) 7.68 (d, J = 8.56 Hz, 1 H) 8.14 (d, J = 0.73 Hz, 1 H) 8.21 (d, J = 8.56 Hz, 1 H) 8.90 (br. s., 1 H) | $R_t$ = 0.48 min, $[M + H]^+$ 466 | HpH_Ext_MethC |
| 13 | 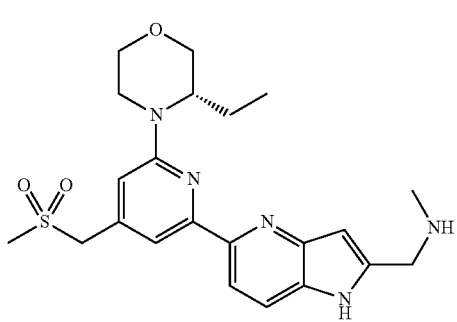<br>(S)-1-(5-(6-(3-ethylmorpholino)-4-((methylsulfonyl)methyl)pyridin-2-yl)-1H-pyrrolo[3,2-b]pyridin-2-yl)-N-methylmethanamine | 30 | $^1$H NMR (400 MHz, CHLOROFORM-d) δ ppm 1.00 (t, J = 7.46 Hz, 3 H) 1.55-1.78 (m, 1 H) 1.86-2.01 (m, 1 H) 2.52 (s, 3 H) 2.86 (s, 3 H) 3.28-3.39 (m, 1 H) 3.63-3.78 (m, 2 H) 3.99-4.09 (m, 4 H) 4.14 (d, J = 12.23 Hz, 1 H) 4.27 (s, 3 H) 6.58-6.74 (m, 2 H) 7.70 (d, J = 8.56 Hz, 1 H) 7.81 (s, 1 H) 8.24 (d, J = 8.56 Hz, 1 H) 8.79 (br. s., 1 H) | $R_t$ = 0.38 min, $[M + H]^+$ 444 | XBridge Prep C18 OBD column acetonitrile in aqueous ammonium bicarbonate |

| Example | Compound | Int | NMR | LCMS (System B, UV, ESI): | MDAP |
|---|---|---|---|---|---|
| 14 | 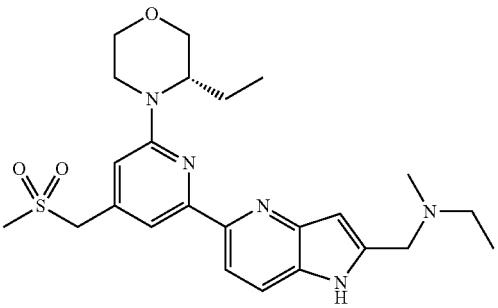<br>(S)-N-((5-(6-(3-ethylmorpholino)-4-((methylsulfonyl)-methyl)pyridin-2-yl)-1H-pyrrolo[3,2-b]pyridin-2-yl)-methyl)-N-methylethanamine | 30 | $^{1}$H NMR (600 MHz, CHLOROFORM-d) δ ppm 1.00 (t, J = 7.52 Hz, 3 H) 1.14 (t, J = 6.97 Hz, 3 H) 1.65-1.74 (m, 1 H) 1.96 (ddd, J = 13.85, 9.08, 7.15 Hz, 1 H) 2.28 (s, 3 H) 2.55 (q, J = 6.97 Hz, 2 H) 2.85 (s, 3 H) 3.33 (td, J = 12.56, 3.48 Hz, 1 H) 3.64-3.74 (m, 1 H) 3.75 (s, 2 H) 3.98-4.08 (m, 2 H) 4.13 (d, J = 12.47 Hz, 1 H) 4.22 (br. s., 1 H) 4.27 (s, 2 H) 6.61 (s, 1 H) 6.70 (s, 1 H) 7.70 (d, J = 8.44 Hz, 1 H) 7.80 (s, 1 H) 8.24 (d, J = 8.80 Hz, 1 H) 8.89 (br. s., 1 H) | $R_t$ = 0.41 min, [M + H]$^+$ 472 | XBridge Prep C18 OBD column acetonitrile in aqueous ammonium bicarbonate |
| 15 | 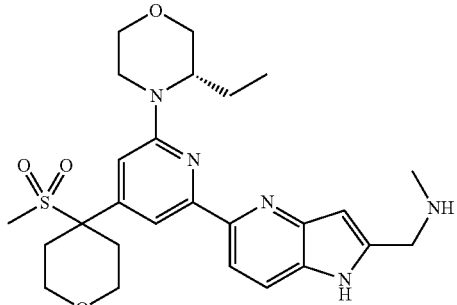<br>(S)-1-(5-(6-(3-ethylmorpholino)-4-(4-(methylsulfonyl)tetrahydro-2H-pyran-4-yl)pyridin-2-yl)-1H-pyrrolo[3,2-b]pyridin-2-yl)-N-methylmethanamine | 31 | $^{1}$H NMR (400 MHz, CHLOROFORM-d δ ppm 0.99 (t, J = 7.46 Hz, 3 H) 1.63-1.75 (m, 2 H) 1.89-2.01 (m, 1 H) 2.51 (s, 3 H) 2.54-2.73 (m, 78 H) 3.33 (td, J = 12.59, 3.67 Hz, 1 H) 3.45-3.62 (m, 2 H) 3.65-3.81 (m, 2 H) 3.98-4.11 (m, 6 H) 4.12-4.21 (m, 2 H) 6.60 (s, 1 H) 6.80 (s, 1 H) 7.70 (d, J = 8.56 Hz, 1 H) 8.03 (s, 1 H) 8.27 (d, J = 8.56 Hz, 1 H) 8.90 (br. s., 1 H) | $R_t$ = 0.43 min, [M + H]$^+$ 514 | XBridge Prep C18 OBD column acetonitrile in aqueous ammonium bicarbonate |
| 16 | 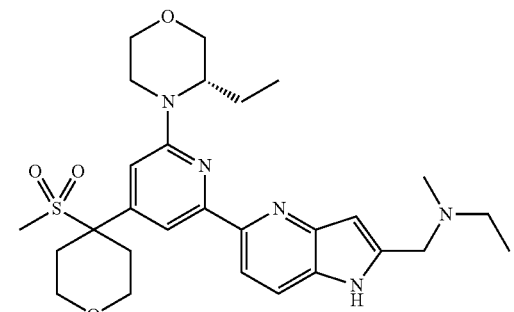<br>(S)-N-((5-(6-(3-ethylmorpholino)-4-(4-(methylsulfonyl)tetrahydro-2H-pyran-4-yl)pyridin-2-yl)-1H-pyrrolo[3,2-b]pyridin-2-yl)methyl)-N-methylmethanamine | 31 | $^{1}$H NMR (400 MHz, CHLOROFORM-d) δ ppm 0.99 (t, J = 7.46 Hz, 3 H) 1.14 (t, J = 7.09 Hz, 3 H) 1.63-1.79 (m, 1 H) 1.84-2.07 (m, 5 H) 2.27 (s, 3 H) 2.47-2.75 (m, 9 H) 3.33 (td, J = 12.72, 3.67 Hz, 1 H) 3.45-3.63 (m, 2 H) 3.66-3.83 (m, 4 H) 3.95-4.11 (m, 4 H) 4.12-4.23 (m, 2 H) 6.60 (s, 1 H) 6.80 (d, J = 1.22 Hz, 1 H) 7.70 (dd, J = 8.56, 0.73 Hz, 1 H) 8.03 (d, J = 0.98 Hz, 1 H) 8.27 (d, J = 8.56 Hz, 1 H) 8.88 (br. s., 1 H) | $R_t$ = 0.46 min, [M + H]$^+$ 542 | XBridge Prep C18 OBD column acetonitrile in aqueous ammonium bicarbonate |

| Example | Compound | Int | NMR | LCMS (System B, UV, ESI): | MDAP |
|---|---|---|---|---|---|
| 17 | 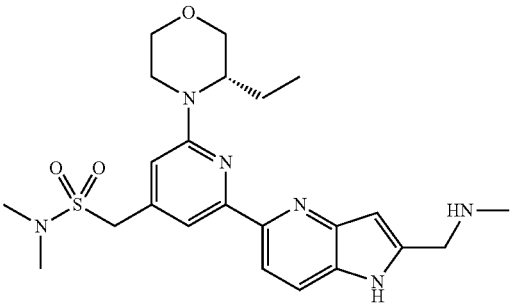<br>(S)-1-(2-(3-ethylmorpholino)-6-(2-((methylamino)methyl)-1H-pyrrolo[3,2-b]pyridin-5-yl)pyridin-4-yl)-N,N-dimethylmethanesulfonamide | 33 | $^1$H NMR (400 MHz, CHLOROFORM-d) δ ppm 0.98 (t, J = 7.46 Hz, 3 H) 1.59-1.72 (m, 1 H) 1.86-2.01 (m, 1 H), 2.49 (s, 3 H), 2.82 (s, 6 H), 3.30 (td, J = 12.50, 3.91 Hz, 1 H) 3.62-3.76 (m, 2 H) 3.97-4.06 (m, 4 H) 4.07-4.14 (m, 1 H) 4.16-4.23 (m, 1 H) 6.69 (d, J = 0.73 Hz, 1 H) 7.67 (dd, J = 8.44, 0.86 Hz, 1 H) 7.80 (d, J = 0.73 Hz, 1 H) 8.21 (d, J = 8.56 Hz, 1 H), 8.90 (s, 1 H) | R$_t$ = 0.96 min, [M + H]$^+$ 473.2 | HPH Method C |

Example 18 [(5-{6-[(3S)-3-ethylmorpholin-4-yl]-4-(2-methanesulfonylpropan-2-yl)pyridin-2-yl}-1H-pyrrolo[3,2-b]pyridin-2-yl)methyl](methyl)amine (The Compound of Example 1 by Route B)

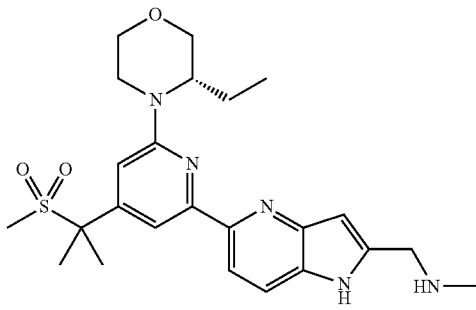

tert-butyl (S)-((5-(6-(3-ethyl morpholino)-4-(2-(methylsulfonyl)propan-2-yl)pyridin-2-yl)-1H-pyrrolo[3,2-b]pyridin-2-yl)methyl)(methyl)carbamate (103 mg, 0.142 mmol, Intermediate 15) was taken in 1,4-Dioxane (1 mL), 4 M HCl in dioxane (0.4 mL, 1.600 mmol, Sigma Aldrich) was added and the reaction mixture was stirred at room temperature for 5.5 hr. The mixture was concentrated in vacuo, then redissolved in minimal methanol and loaded onto aminopropyl (NH2) SPE (5 g, primed with methanol (1 CV)), eluting with methanol (3 CV), eluent concentrated in vacuo to give a brown/orange residue dissolved in 1:1 meOH:DMSO (1 mL) and purified by HpH MDAP extended method, C. Appropriate fractions concentrated in vacuo to give (S)-1-(5-(6-(3-ethyl morpholino)-4-(2-(methylsulfonyl)propan-2-yl)pyridin-2-yl)-1H-pyrrolo[3,2-b]pyridin-2-yl)-N-methylmethanamine (54.7 mg, 0.116 mmol, 81 yield) as a yellow solid.

Similarly prepared by the general scheme II were:

| | Compound | Int | NMR | LCMS (System B, UV, ESI): | MDAP |
|---|---|---|---|---|---|
| 19 | 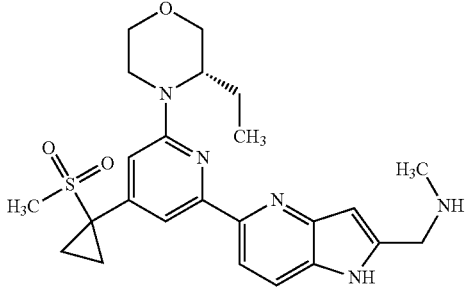<br>[(5-{6-[(3S)-3-ethylmorpholin-4-yl]-4-(1-methanesulfonylcyclopropyl)pyridin-2-yl}-1H-pyrrolo[3,2-b]pyridin-2-yl)methyl](methyl)amine | 35 | 1H NMR (400 MHz, CHLOROFORM-d) Shift 8.77-9.05 (bs, 1 H), 8.24 (d, J = 8.56 Hz, 1 H), 7.90 (d, J = 1.22 Hz, 1 H), 7.70 (dd, J = 0.73, 8.56 Hz, 1 H), 6.91 (d, J = 0.98 Hz, 1 H), 6.58-6.67 (m, 1 H), 4.18-4.34 (m, 1 H), 3.98-4.14 (m, 3 H), 3.63-3.87 (m, 2 H), 3.33 (dt, J = 3.91, 12.59 Hz, 1 H), 2.88 (s, 3 H), | Rt = 0.44 min, [M + H]+ 470 | HpH_Meth C Followed by THF HPLC |

| Compound | | Int | NMR | LCMS (System B, UV, ESI): | MDAP |
|---|---|---|---|---|---|
| | | | 2.63 (s, 1 H), 2.52 (s, 3 H), 2.38 (s, 1 H), 1.82-2.07 (m, 4 H), 1.59-1.79 (m, 1 H), 1.35-1.52 (m, 2 H), 1.00 (t, J = 7.46 Hz, 3 H) | | |
| 20 | ({5-[4-(1-methanesulfonylcyclopropyl)-6-[(3S)-3-methylmorpholin-4-yl]pyridin-2-yl]-1H-pyrrolo[3,2-b]pyridin-2-yl}methyl)(methyl)amine | 36 | 1H NMR (400 MHz, CHLOROFORM-d) Shift 8.88-9.16 (m, 1 H), 8.24 (d, J = 8.31 Hz, 1 H), 7.93 (d, J = 1.22 Hz, 1 H), 7.69 (dd, J = 0.98, 8.56 Hz, 1 H), 6.92 (d, J = 0.98 Hz, 1 H), 6.62 (s, 1 H), 5.32 (s, 1 H), 4.48 (q, J = 6.28 Hz, 1 H), 4.00-4.10 (m, 4 H), 3.79-3.91 (m, 2 H), 3.61-3.76 (m, 1 H), 3.33 (dt, J = 3.55, 12.53 Hz, 1 H), 2.87 (s, 3 H), 2.58-2.77 (m, 1 H), 2.46-2.55 (m, 3 H), 2.27-2.40 (m, 1 H), 2.15 (br s, 1 H), 1.98-2.10 (m, 1 H), 1.79-1.96 (m, 2 H), 1.28-1.49 (m, 5 H) | $R_t$ = 0.40 min, [M + H]$^+$ 456 | HpH_Meth C |
| 21 | 1-(5-{6-[(3S)-3-ethylmorpholin-4-yl]-4-(2-methanesulfonylpropan-2-yl)pyridin-2-yl}-1H-pyrrolo[3,2-b]pyridin-2-yl)methanamine | 14 + 38 | 1H NMR (400 MHz, CHLOROFORM-d) Shift 8.67-8.96 (m, 1 H), 8.23 (d, J = 8.56 Hz, 1 H), 8.02 (d, J = 1.22 Hz, 1 H), 7.70 (dd, J = 0.73, 8.56 Hz, 1 H), 6.98 (d, J = 1.47 Hz, 1 H), 6.57 (d, J = 0.98 Hz, 1 H), 4.10-4.25 (m, 4 H), 3.97-4.10 (m, 2 H), 3.62-3.87 (m, 2 H), 3.32 (dt, J = 3.91, 12.59 Hz, 1 H), 2.57-2.71 (m, 3 H), 1.85-2.04 (m, 6 H), 1.70-1.82 (m, 2 H), 1.52-1.68 (m, 2 H), 1.00 (t, J = 7.46 Hz, 3 H) | $R_t$ = 0.44 min, [M + H]$^+$ 458 | HpH 20-60% |

Example 22 (the compound of Example 15) by route C: (S)-1-(5-(6-(3-ethylmorpholino)-4-(4-(methylsulfonyl)tetrahydro-2H-pyran-4-yl)pyridin-2-yl)-1H-pyrrolo[3,2-b]pyridin-2-yl)-N-methylmethanamine

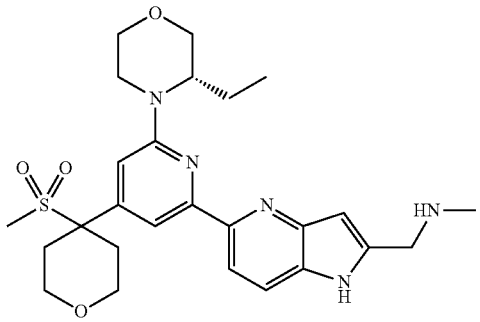

To a solution of Intermediate 46 tert-butyl (S)-((5-(6-(3-ethylmorpholino)-4-(4-(methylsulfonyl)tetrahydro-2H-pyran-4-yl)pyridin-2-yl)-1H-pyrrolo[3,2-b]pyridin-2-yl)methyl)(methyl)carbamate (24.55 g, 40.0 mmol) in Isopropanol (40 mL) was added 5-6N HCl in IPA (44.0 mL, 220 mmol) and the reaction mixture was stirred at 40C for 3 hours. The reaction mixture was concentrated in vacuo. The residue was separated between ethyl acetate (300 ml) and saturated sodium bicarbonate solution (600 ml). The aqueous phase was extracted with ethyl acetate (200 ml). The combined organic phases were washed with brine (200 ml) and dried over magnesium sulphate. The solvent was removed in vacuo. The residue was dissolved in ethyl acetate and applied to a 375 g KP-NH2 cartridge. This was eluted with ethyl acetate for 5 minutes, a gradient of 0-25% ethanol in ethyl acetate over 5 minutes and then 25% ethanol in ethyl acetate for 10 minutes. The required fractions were combined and evaporated in vacuo to give (S)-1-(5-(6-(3-ethylmorpholino)-4-(4-(methylsulfonyl)tetrahydro-2H-pyran-4-yl)pyridin-2-yl)-1H-pyrrolo[3,2-b]pyridin-2-yl)-N-methylmethanamine (15.56 g, 76%) as an off-white solid. $^1$H NMR (400 MHz, DMSO-$d_6$) δ 11.25 (br s, 1H), 8.15 (d, J=8.37 Hz, 1H), 7.90 (s, 1H), 7.77 (d, J=8.60 Hz, 1H), 6.85 (s, 1H), 6.48 (s, 1H), 4.33 (br t, J=5.17 Hz, 1H), 4.26 (br m, 1H), 4.18 (br d, J=11.81 Hz, 1H), 3.88-4.03 (m, 4H), 3.84 (s, 2H), 3.50-3.70 (m, 2H), 3.11-3.29 (m, 3H), 2.63-2.80 (m, 5H), 2.25-2.37 (m, 5H), 1.72-1.94 (m, 1H), 1.50-1.67 (m, 1H), 0.90 (t, J=7.63 Hz, 3H). LCMS (System A, UV, ESI): $R_t$=0.89 min, [M+H]$^+$ 514.

Similarly prepared by Route C were:

| | Compound | Int | NMR | LCMS (System B, UV, ESI): | DAP |
|---|---|---|---|---|---|
| 23 | 1-(5-{6-[(3S)-3-ethylmorpholin-4-yl]-4-(4-methanesulfonyloxan-4-yl)pyridin-2-yl}-1H-pyrrolo[3,2-b]pyridin-2-yl)methanamine | 43 & 38 | 1H NMR (400 MHz, CHLOROFORM-d) Shift 8.86 (s, 1 H), 8.27 (d, J = 8.56 Hz, 1 H), 8.02 (d, J = 1.22 Hz, 1 H), 7.71 (dd, J = 0.73, 8.56 Hz, 1 H), 6.80 (d, J = 1.47 Hz, 1 H), 6.57 (s, 1 H), 4.00-4.23 (m, 8 H), 3.66-3.80 (m, 2 H), 3.46-3.61 (m, 2 H), 3.33 (dt, J = 3.79, 12.65 Hz, 1 H), 2.53-2.72 (m, 5 H), 1.89-2.02 (m, 2 H), 1.63-1.84 (m, 4 H), 0.99 (t, J = 7.46 Hz, 3 H) | $R_t$ = 0.42 min, [M + H]$^+$ 500 | 0% to 97% Acetonitrile = 10 mM Ammonium bicarbonate |

-continued

| Compound | Int | NMR | LCMS (System B, UV, ESI): | DAP |
|---|---|---|---|---|
| 24 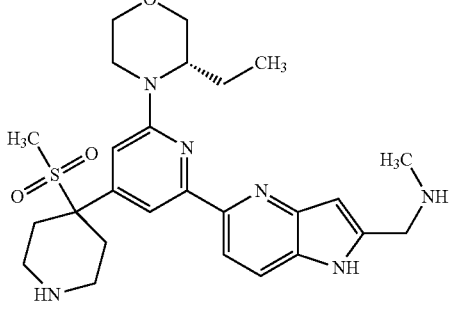 [(5-{6-[(3S)-3-ethylmorpholin-4-yl]-4-(4-methanesulfonylpiperidin-4-yl)pyridin-2-yl}-1H-pyrrolo[3,2-b]pyridin-2-yl)methyl](methyl)amine | 48 & 69 | 1H NMR (400 MHz, DMSO-d6) Shift 11.20-11.31 (m, 1 H), 8.15 (d, J = 8.31 Hz, 1 H), 7.89 (d, J = 0.73 Hz, 1 H), 7.76 (dd, J = 0.86, 8.44 Hz, 1 H), 6.82 (s, 1 H), 6.49 (s, 1 H), 4.13-4.27 (m, 2 H), 3.89-4.02 (m, 2 H), 3.81-3.87 (m, 2 H), 3.51-3.67 (m, 3 H), 3.15 (dt, J = 3.91, 12.84 Hz, 2 H), 2.98 (br dd, J = 4.89, 9.78 Hz, 2 H), 2.70 (s, 3 H), 2.61-2.68 (m, 2 H), 2.36-2.45 (m, 2 H), 2.33 (s, 3 H), 2.06-2.19 (m, 2 H), 1.80 (br dd, J = 1.83, 6.72 Hz, 1 H), 1.52-1.65 (m, 1 H), 0.84-0.97 (m, 3 H) | Rt = 0.80 min, [M + H]+ 513 | PH_MethA |
| 25 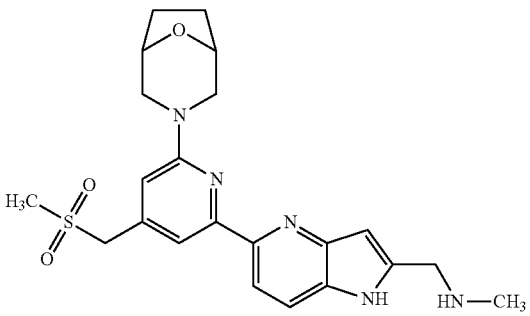 ({5-[4-(methanesulfonylmethyl)-6-{8-oxa-3-azabicyclo[3.2.1]octan-3-yl}pyridin-2-yl]-1H-pyrrolo[3,2-b]pyridin-2-yl}methyl)(methyl)amine | 49 & 45 | 1H NMR (400 MHz, CHLOROFORM-d) Shift 8.79 (br s, 1 H), 8.26 (d, J = 8.56 Hz, 1 H), 7.85 (d, J = 0.98 Hz, 1 H), 7.70 (dd, J = 0.86, 8.44 Hz, 1 H), 6.67 (d, J = 1.22 Hz, 1 H), 6.61 (s, 1 H), 4.56 (br d, J = 2.45 Hz, 2 H), 4.27 (s, 2 H), 3.97-4.06 (m, 4 H), 3.25 (dd, J = 2.45, 12.23 Hz, 2 H), 2.86 (s, 3 H), 2.52 (s, 3 H), 1.89-2.07 (m, 4 H), 0.03-0.24 (m, 1 H) | $R_t$ = 0.35 min, $[M + H]^+$ 442 | PH_MethA |

| Compound | Int | NMR | LCMS (System B, UV, ESI): | DAP |
|---|---|---|---|---|
| 26 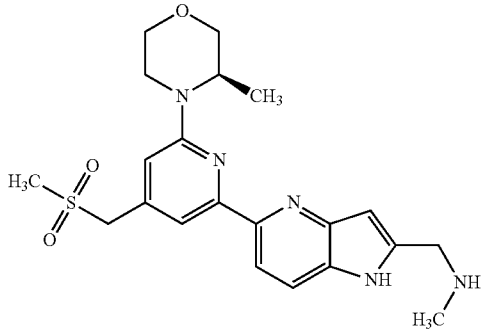 ({5-[4-(methanesulfonylmethyl)-6-[(3R)-3-methylmorpholin-4-yl]pyridin-2-yl]-1H-pyrrolo[3,2-b]pyridin-2-yl}methyl)(methyl)amine | 50 & 45 | 1H NMR (400 MHz, DMSO-d6) Shift 11.25-11.41 (m, 1 H), 8.15 (d, J = 8.56 Hz, 1 H), 7.83 (d, J = 0.73 Hz, 1 H), 7.78 (dd, J = 0.73, 8.56 Hz, 1 H), 6.77 (s, 1 H), 6.52 (s, 1 H), 4.54 (s, 2 H), 4.35-4.46 (m, 1 H), 3.97-4.09 (m, 2 H), 3.93 (s, 2 H), 3.67-3.83 (m, 2 H), 3.56 (dt, J = 2.93, 11.74 Hz, 1 H), 3.12-3.22 (m, 1 H), 2.99 (s, 3 H), 2.39 (s, 3 H), 1.20 (d, J = 6.60 Hz, 3 H) | $R_t$ = 0.34 min, [M + H]$^+$ 430 | /A |
| 27 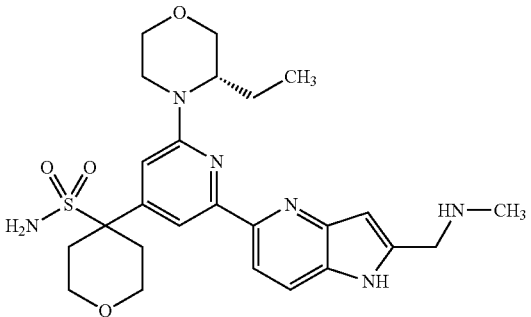 4-{2-[(3S)-3-ethylmorpholin-4-yl]-6-{2-[(methylamino)methyl]-1H-pyrrolo[3,2-b]pyridin-5-yl}pyridin-4-yl}oxane-4-sulfonamide | 59 + 69 | 1H NMR (400 MHz, METHANOL-d4) d = 8.19 (1H, d, J = 8.6 Hz), 7.77-7.87 (2H, m), 6.86 (1H, s), 6.62 (1H, s), 4.20-4.29 (1H, m), 4.11-4.19 (1H, m), 3.90-4.05 (6H, m), 3.59-3.76 (2H, m), 3.44 (2H, dd, J = 21.8 Hz, J = 11.2 Hz), 3.22-3.36 (1H, m), 2.72 (2H, d, J = 13.7 Hz), 2.43-2.55 (5H, m), 1.83-1.98 (1H, m), 1.63-1.79 (1H, m), 0.98 (3H, t, J = 7.6 Hz) | $R_t$ = 0.84 min, [M + H]$^+$ 515 | PH_MethA |
| 28 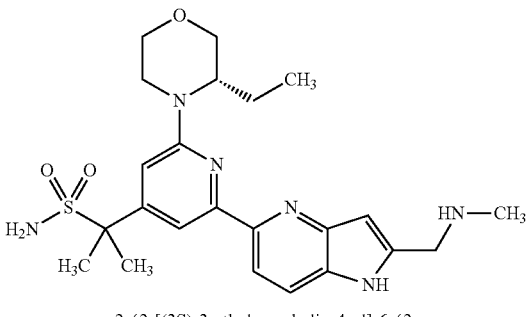 2-{2-[(3S)-3-ethylmorpholin-4-yl]-6-{2-[(methylamino)methyl]-1H-pyrrolo[3,2-b]pyridin-5-yl}pyridin-4-yl}propane-2-sulfonamide | 60 + 69 | 1H NMR (400 MHz, METHANOL-d4) d = 8.13 (1H, d, J = 8.6 Hz), 7.86 (1H, d, J = 1.0 Hz), 7.80 (1H, dd, J = 8.6 Hz, J = 0.7 Hz), 6.95 (1H, d, J = 1.2 Hz), 6.62 (1H, s), 4.24 (1H, br. S.), 4.08-4.16 (1H, m), 3.95-4.03 (2H, m), 3.93 (2H, s), 3.59-3.74 (2H, m), 3.22-3.34 (1H, m), 2.44 (3H, s), 1.79-1.97 (7H, m), 1.62- | $R_t$ = 0.89 min, [M + H]$^+$ 473 | PH_MethA |

| Compound | | Int | NMR | LCMS (System B, UV, ESI): | DAP |
|---|---|---|---|---|---|
| | | | 1.76 (1H, m), 0.98 (3H, t, J = 7.5 Hz) | | |
| 29 | {2-[(3S)-3-ethylmorpholin-4-yl]-6-{2-[(methylamino)methyl]-1H-pyrrolo[3,2-b]pyridin-5-yl}pyridin-4-yl}methanesulfonamide | 58 + 69 | 1H NMR (400 MHz, METHANOL-d4) d = 8.10 (1H, d, J = 8.6 Hz), 7.79 (1H, d, J = 8.6 Hz), 7.63 (1H, s), 6.75 (1H, s), 6.60 (1H, s), 4.38 (2H, s), 4.22-4.32 (1H, m), 4.10 (1H, d, J = 12.0 Hz), 3.88-4.02 (4H, m), 3.56-3.73 (2H, m), 3.21-3.32 (1H, m), 2.40-2.46 (3H, m), 1.80-1.98 (1H, m), 1.61-1.76 (1H, m, M14), 0.97 (3H, t, J = 7.5 Hz) | $R_t$ = 0.82 min, [M + H]$^+$ 445 | PH_MethA |
| 30 | 1-{2-[(3S)-3-ethylmorpholin-4-yl]-6-{2-[(methylamino)methyl]-1H-pyrrolo[3,2-b]pyridin-5-yl}pyridin-4-yl}-N-methylmethanesulfonamide | | 1H NMR (400 MHz, CHLOROFORM-d) d = 9.23 (1H, br. s), 8.09 (1H, d, J = 8.6 Hz), 7.74 (1H, s), 7.64 (1H, d, J = 8.6 Hz), 6.60 (1H, s), 6.48 (1H, s), 4.27 (2H, s), 3.92-4.21 (4H, m), 3.84 (2H, s), 3.55-3.71 (2H, m), 3.26 (1H, td, J = 12.6 Hz, J = 3.7 Hz), 2.77 (3H, s), 2.41 (3H, s), 1.84-1.99 (1H, m), 1.55-1.71 (1H, m), 0.96 (3H, t, J = 7.5 Hz) | $R_t$ = 0.88 min, [M + H]$^+$ 459 | PH_MethA |
| 31 | 4-{2-[(3S)-3-ethylmorpholin-4-yl]-6-{2-[(methylamino)methyl]-1H-pyrrolo[3,2-b]pyridin-5-yl}pyridin-4-yl}-N,N-dimethyloxane-4-sulfonamide | 63 + 69 | 1H NMR (400 MHz, CHLOROFORM-d) d = 8.75 (1H, br. s), 8.25 (1H, d, J = 8.6 Hz), 8.06 (1H, d, J = 1.2 Hz), 7.62-7.73 (1H, m), 6.77 (1H, d, J = 1.0 Hz), 6.59 (1H, s), 3.92-4.22 (8H, m), 3.64-3.82 (2H, m), 3.40-3.55 (2H, m), 3.24-3.37 (1H, m), 3.23-3.38 (1H, m), 2.56-2.74 (10H, m), 2.50 | $R_t$ = 1.00 min, [M + H]$^+$ 543 | PH_MethA |

| Compound | Int | NMR | LCMS (System B, UV, ESI): | DAP |
|---|---|---|---|---|
| | | (3H, s), 1.86-2.03 (1H, m), 1.58-1.76 (1H, m), 0.98 (3H, t, J = 7.5 Hz) | | |

Example 32: (5-{6-[(3S)-3-ethylmorpholin-4-yl]-4-(2-methanesulfonyl)propan-2-yl)pyridin-2-yl}-1H-pyrrolo[3,2-b]pyridin-2-yl)methanol

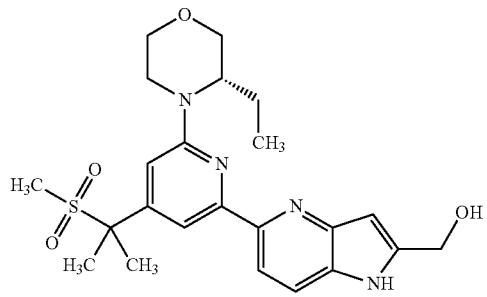

DIBAL-H 1M in DCM (0.176 mL, 0.176 mmol) was added to a solution of Intermediate 70 ethyl (S)-5-(6-(3-ethylmorpholino)-4-(2-(methylsulfonyl)propan-2-yl)pyridin-2-yl)-1H-pyrrolo[3,2-b]pyridine-2-carboxylate (40 mg, 0.080 mmol) in dry Tetrahydrofuran (THF) (1 mL) under an atmosphere of nitrogen at −78° C. The resulting solution was stirred at −78° C. for 2 h.

The mixture was warmed up to rt and stirred at this temperature for 1 h 15. DIBAL-H 1M in DCM (0.080 mL, 0.080 mmol) was added and the resulting mixture was stirred at RT for 18 h DIBAL-H 1M in DCM (0.050 mL, 0.050 mmol) was added and the resulting mixture was stirred at RT for 2 h. DIBAL-H 1M in DCM (0.080 mL, 0.080 mmol) was added and the resulting mixture was stirred at RT for 30 min.

Rochelle salt aqueous solution (10%, 3 mL) was slowly added to the resulting mixture. DCM (5 mL) was added and the resulting mixture was vigourously stirred for 20 min. The phases were separated and the aqueous phase was extracted with additional DCM (2×3 mL). The organic phases were combined and the volatiles were removed under reduced pressure to give a residue that was purified by reverse phase chromatography using the elution gradient acetonitrile in water (formic acid modifier) 5-50% to give (S)-(5-(6-(3-ethylmorpholino)-4-(2-(methylsulfonyl)propan-2-yl)pyridin-2-yl)-1H-pyrrolo[3,2-b]pyridin-2-yl)methanol (22 mg, 0.048 mmol, 60.0% yield) as a yellow solid. 1H NMR (400 MHz, CHLOROFORM-d) Shift 8.21 (d, J=8.56 Hz, 1H), 7.97 (d, J=1.22 Hz, 1H), 7.77 (dd, J=0.73, 8.56 Hz, 1H), 6.98 (d, J=1.47 Hz, 1H), 6.51-6.73 (m, 1H), 4.93 (s, 2H), 4.10-4.32 (m, 3H), 3.90-4.10 (m, 2H), 3.60-3.82 (m, 2H), 3.33 (dt, J=3.67, 12.59 Hz, 1H), 1.89-2.03 (m, 6H), 1.58-1.76 (m, 1H), 1.00 (t, J=7.46 Hz, 3H). LCMS (System B, UV, ESI): $R_f$=0.59 min, [M+H]$^+$ 458

Similarly prepared to example 35 were:

| Example | Compound | Int | NMR | LCMS (System B, UV, ESI): | MDAP |
|---|---|---|---|---|---|
| 33 | (5-{6-[(3S)-3-ethylmorpholin-4-yl]-4-(4-methanesulfonyloxan-4-yl)pyridin-2-yl}-1H-pyrrolo[3,2-b]pyridin-2-yl)methanol | 71 | 1H NMR (400 MHz, CHLOROFORM-d) Shift 8.56 (br s, 1 H), 8.30 (d, J = 8.56 Hz, 1 H), 8.02 (d, J = 1.22 Hz, 1 H), 7.74 (dd, J = 0.73, 8.56 Hz, 1 H), 6.81 (d, J = 1.22 Hz, 1 H), 6.62 (dd, J = 0.98, 1.96 Hz, 1 H), 4.94 (s, 2 H), 3.96-4.22 (m, 4 H), 3.63-3.89 (m, 2 H), 3.43-3.63 (m, 2 H), 3.33 (dt, J = 3.55, 12.65 Hz, 1 H), 2.50-2.74 (m, 6 H), 2.07-2.33 (m, 1 H), 1.87-2.07 (m, 2 H), 1.60-1.82 (m, 1 H), 0.99 (t, J = 7.46 Hz, 3 H). | LCMS (System B UV, ESI): $R_f$ = 0.55 min, [M + H]$^+$ 501 | |

| Example | Compound | Int | NMR | LCMS (System B, UV, ESI): | MDAP |
|---|---|---|---|---|---|
| 34 | 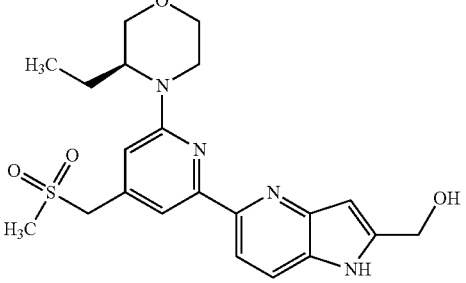<br>(5-{6-[(3S)-3-ethylmorpholin-4-yl]-4-(methanesulfonylmethyl)pyridin-2-yl}-1H-pyrrolo[3,2-b]pyridin-2-yl)methanol | 51 | 1H NMR (400 MHz, CHLOROFORM-d) d = 8.16 (d, J = 8.3 Hz, 1 H), 7.79-7.71 (m, 2 H), 6.70 (s, 1 H), 6.60 (s, 1 H), 4.93 (s, 2 H), 4.28 (s, 2 H), 4.22-3.97 (m, 4 H), 3.73 (d, J = 11.7 Hz, 2 H), 3.33 (dt, J = 3.5, 12.5 Hz, 1 H), 2.90 (s, 3 H), 2.04-1.88 (m, 1 H), 1.80-1.60 (m, 1 H), 1.00 (t, J = 7.5 Hz, 3 H) | R$_t$ = 0.83 min, [M + H]$^+$ 431 | 20% to 60% Acetonitrile = 10 mM Ammonium bicarbonate |
| 35 | 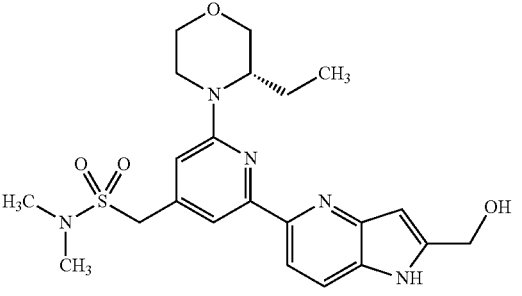<br>1-{2-[(3S)-3-ethylmorpholin-4-yl]-6-[2-(hydroxymethyl)-1H-pyrrolo[3,2-b]pyridin-5-yl]pyridin-4-yl}-N,N-dimethylmethanesulfonamide | 66 + 69 | 1H NMR (400 MHz, METHANOL-d4) d = 8.14 (1H, d, J = 8.6 Hz), 7.80 (1H, d, J = 8.6 Hz), 7.64 (1H, s), 6.77 (1H, s), 6.59 (1H, s), 4.35 (2H, s), 4.25 (1H, br. s), 4.12 (1H, d, J = 11.5 Hz), 3.92-4.04 (2H, m), 3.56-3.74 (2H, m), 3.35 (2H, s), 3.20-3.30 (1H, m), 2.84 (6H, s), 1.80-1.97 (1H, m), 1.68 (1H, s), 0.96 (3H, t, J = 7.5 Hz) | R$_t$ = 0.91 min, [M + H]$^+$ 460 | HPH_MethA |

The formic acid salt of Example 34 has also been prepared using methods standard in the art.

Example 36 (5-{6-[(3S-3-ethylmorpholin-4-yl]-4-(4-methanesulfonylpiperidin-4-yl)pyridin-2-yl}-1H-pyrrolo[3,2-b]pyridin-2-yl)methanol

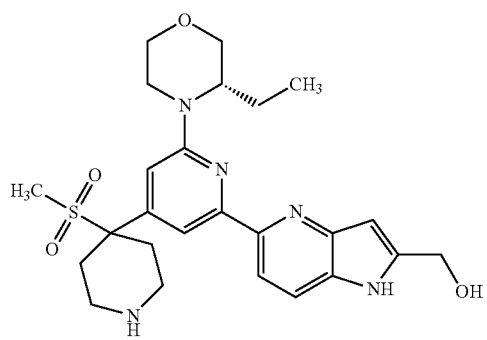

Intermediate 75 tert-butyl (S)-4-(2-(3-ethylmorpholino)-6-(2-(hydroxymethyl)-1H-pyrrolo[3,2-b]pyridin-5-yl)pyridin-4-yl)-4-(methylsulfonyl)piperidine-1-carboxylate (33 mg, 0.055 mmol) was dissolved in Dichloromethane (DCM) (1.0 mL):TFA (500 µl, 6.49 mmol). The resulting mixture was stirred for 1 h.

The volatiles were removed under a flow of nitrogen and the residue was dissolved in 5% MeOH in DCM (10 mL). The resulting solution was washed with aqueous K2CO3 (5% 5 mL). The phases were separated and the aqueous phase was extracted with additional DCM (2×5 mL). The organic phases were combined and the volatiles reduced under reduced pressure to give (S)-(5-(6-(3-ethylmorpholino)-4-(4-(methylsulfonyl)piperidin-4-yl)pyridin-2-yl)-1H-pyrrolo[3,2-b]pyridin-2-yl)methanol (22 mg, 0.044 mmol, 80% yield) as a colourless solid. 1H NMR (400 MHz, DMSO-d6) Shift 11.21-11.48 (m, 1H), 8.16 (d, J=8.56 Hz, 1H), 7.89 (s, 1H), 7.71-7.83 (m, 1H), 6.81-6.85 (m, 1H), 6.47-6.50 (m, 1H), 5.41 (t, J=5.62 Hz, 1H), 4.68 (d, J=5.62 Hz, 2H), 4.13-4.25 (m, 2H), 3.89-4.01 (m, 2H), 3.52-3.66 (m, 2H), 3.15 (dt, J=3.55, 12.90 Hz, 1H), 2.93-3.02 (m, 2H), 2.57-2.71 (m, 5H), 2.33-2.48 (m, 2H), 2.02-2.17 (m, 3H), 1.81 (ddd, J=7.46, 8.80, 13.57 Hz, 1H), 1.50-1.63 (m, 1H), 0.90 (t, J=7.46 Hz, 3H). LCMS (System B, UV, ESI): R$_t$=0.37 min, [M+H]$^+$ 500

Similarly prepared by Route C was:

| Ex | Compound | nt | NMR | LCMS (System B, UV, ESI): | DAP |
|---|---|---|---|---|---|
| 37 | ({5-[4-(4-methanesulfonyloxan-4-yl)-6-{8-oxa-3-azabicyclo[3.2.1]octan-3-yl}pyridin-2-yl]-1H-pyrrolo[3,2-b]pyridin-2-yl}methyl)(methyl)amine | 8h h4 46 86 | $^1$H NMR (400 MHz, CHLOROFORM-d) δ 9.38 (br s, 1 H), 8.28 (d, J = 8.56 Hz, 1 H), 8.05 (d, J = 1.22 Hz, 1 H), 7.69 (dd, J = 0.73, 8.56 Hz, 1 H), 6.74 (d, J = 1.22 Hz, 1 H), 6.59 (s, 1 H), 4.51-4.61 (m, 2 H), 3.92-4.08 (m, 6 H), 3.41-3.57 (m, 2 H), 3.24 (dd, J = 2.45, 12.23 Hz, 2 H), 2.51-2.68 (m, 6 H), 2.48 (s, 3 H), 2.23 (br s, 2 H), 1.89-2.14 (m, 4 H), | $R_t$ = 0.39 min, [M + H]$^+$ 512 | |

The following Examples have also been prepared by similar methods to those set out above, from the relevant intermediates: Example 38: [(5-{6-[(3R)-3-ethyl morpholin-4-yl]-4-(methanesulfonylmethyl)pyridin-2-yl}-1H-pyrrolo[3,2-b]pyridin-2-yl)methyl](methyl)amine Example 39: 1-(4-{2-[(3S)-3-ethylmorpholin-4-yl]-6-{2-[(methylamino)methyl]-1H-pyrrolo[3,2-b]pyridin-5-yl}pyridin-4-yl}-4-methanesulfonylpiperidin-1-yl)ethan-1-one Example 40: ({5-[4-(4-methanesulfonyloxan-4-yl)-6-{3-oxa-8-azabicyclo[3.2.1]octan-8-yl}pyridin-2-yl]-1H-pyrrolo[3,2-b]pyridin-2-yl}methyl)(methyl)amine Example 41: [(5-{6-[(3R)-3-ethyl morpholin-4-yl]-4-(4-methanesulfonyloxan-4-yl)pyridin-2-yl}-1H-pyrrolo[3,2-b]pyridin-2-yl)methyl](methyl)amine Example 42: (5-{6-[(3R)-3-ethyl morpholin-4-yl]-4-(methanesulfonylmethyl)pyridin-2-yl}-1H-pyrrolo[3,2-b]pyridin-2-yl)methanol Example 43: (5-{6-[(3R)-3-ethylmorpholin-4-yl]-4-(4-methanesulfonyloxan-4-yl)pyridin-2-yl}-1H-pyrrolo[3,2-b]pyridin-2-yl)methanol Example 44: ({5-[4-(methanesulfonylmethyl)-6-{6-oxa-3-azabicyclo[3.1.1]heptan-3-yl}pyridin-2-yl]-1H-pyrrolo[3,2-b]pyridin-2-yl}methyl)(methyl)amine Example 45: ({5-[4-(methanesulfonylmethyl)-6-(14-oxazepan-4-yl)pyridin-2-yl]-1H-pyrrolo[3,2-b]pyridin-2-yl}methyl)(methyl)amine Example 46: ({5-[4-(methanesulfonylmethyl)-6-(morpholin-4-yl)pyridin-2-yl]-1H-pyrrolo[3,2-b]pyridin-2-yl}methyl)(methyl)amine Example 47: ({5-[4-(methanesulfonylmethyl)-6-{3-oxa-8-azabicyclo[3.2.1]octan-8-yl}pyridin-2-yl]-1H-pyrrolo[3,2-b]pyridin-2-yl}methyl)(methyl)amine Example 48: ({5-[4-(methanesulfonylmethyl)-6-(3-propylmorpholin-4-yl)pyridin-2-yl]-1H-pyrrolo[3,2-b]pyridin-2-yl}methyl)(methyl)amine; and Example 49: {5-[4-(methanesulfonylmethyl)-6-[3-(propan-2-yl)morpholin-4-yl]pyridin-2-yl]-1H-pyrrolo[3,2-b]pyridin-2-yl}methyl)(methyl)amine Example 50 Polymorphic form of the compound of Example 15

Example 50

The compound of Example 15 (100 mg) was weighed into a vial containing stirrer bar. 100 uL MeOH was added. The vial was heated to 46° C. and stirred for 16 h. Slurry was diluted with 0.1 mL MeOH (to thin the slurry), filtered, and washed with 2×0.1 mL MeOH, and sucked dry for 1 h.

The XRPD spectrum of the compound of example 15 is shown in FIG. 1.

Biological Data

Those of skill in the art will recognise that the assays described below are subject to experimental variability. Accordingly, it is to be understood that the values givenbe low are represent the mean of multiple experiments, and that repeating the assay run(s) may result in somewhat different pIC50 values.

Example 51

The affinity of test compounds for mTOR was determined in the mTOR kinobeads assay. This is a competition-binding assay based on the capturing of endogenously expressed target proteins from cell extracts by a bead-immobilized capturing ligand in presence of the test compound.

HuT-78 cells (European Collection of Authenticated Cell Cultures, 88041901) were cultured according to vendor's instructions. Frozen cell pellets were homogenized in 3× pellet volumes lysis buffer (50 mM Tris-HCl, 0.4% (v/v) Igepal-CA630, 5% glycerol, 150 mM NaCl, 1.5 mMMgCl$_2$, 25 mM NaF, 1 mM sodium vanadate, 1 mM DTT, pH 7.5, supplemented with EDTA-free protease inhibitor tablet (Roche)). The sample was dispersed using a Dounce homogenizer, kept rotating for 30 min at 4° C., and centrifuged for 10 min at 20 000 g at 4° C. The supernatant was centrifuged again for 1 h at 145 000 g. The protein concentration was determined by Bradford assay (BioRad), aliquots were snap frozen in liquid nitrogen and stored at −80° C.

The capturing matrices were generated by derivatizing N-hydroxysuccinimide (NHS) activated Sepharose 4 beads (GE Healthcare) with the functionalized ligands Compound A and Compound C at a ligand density of 5 mM. Remaining NHS-groups were blocked with ethanolamine.

For the mTOR kinobeads assay the matrices were combined in a 1:1 ratio and equilibrated in DP buffer (50 mM Tris-HCl (pH 7.5), 0.4% (v/v) Igepal-CA630, 5% (v/v) glycerol, 150 mM NaCl, 1.5 mM MgCl$_2$, 25 mM NaF, 1 mM Na$_3$VO$_4$, 1 mM dithiothreitol). All steps of the mTOR kinobeads assay were performed at 4° C. or on ice. The cell lysate was diluted with DP buffer to a final concentration of 5 mg/ml and a final detergent concentration of 0.4% (v/v) Igepal-CA630. For the assay 250 μg cell lysate and 2.5 μl capturing matrix per well (final assay volume: 75 μl) were incubated in the presence of test compounds in a 384-well filter plate (MultiScreenHTS HV Filter Plate, 0.45 μm, MZHVNOW50, Merck Millipore). Each plate contained 16 positive (100 μM Compound B) and 16 negative (2% v/v DMSO) control wells. Compounds were tested in a concentration-response applying 1:3 or 1:4 dilution steps for in total 11 data points. DMSO concentration was 2% (v/v). After 2 h incubation on an overhead shaker (Roto-Shake Genie, Scientific Industries Inc.) at 4° C. the non-bound fraction was removed by washing the beads with DP buffer. Proteins retained on the beads were eluted in SDS sample buffer (200 mM Tris (pH 7.4), 250 mM Trizma Base, 4% (w/v) SDS, 20% (v/v) glycerol, 0.01% (w/v) bromophenol blue, 50 mM dithiothreitol) into a collection plate (384 well polypropylene microplate, V-shape, Greiner, 781 280). Eluates were spotted on nitrocellulose membranes (400 nl per spot) using an automated pin-tool liquid transfer (Biomek FX, Beckman). After drying, the membranes were rehydrated in 20% (v/v) ethanol and blocked by incubation with Odyssey blocking buffer (LICOR, 927-40000) for 1 h at room temperature. Blocked membranes were incubated overnight at 25° C. with Odyssey blocking buffer supplemented with a specific anti-mTOR antibody (Cell Signaling, 2972; 1:500) and 0.4% TWEEN-20. Then the membranes were washed in PBST buffer and incubated for 60 minutes at room temperature with the detection antibody (IRDye™ labelled antibody from LI-COR) diluted in Odyssey blocking buffer (LICOR 927-40000) containing 0.2% TWEEN-20. Then the membranes were washed with PBST and finally rinsed twice with PBS buffer to remove residual Tween-20. The membranes were then scanned with the Odyssey® Infrared Imaging System (LI-COR Biosciences). Fluorescence signals were recorded and analyzed according to the instructions of the manufacturer. Concentration response curves were computed with the software Activity Base. All data were normalized to the mean of 16 high (negative control) and 16 low (positive control) control wells on each plate. Concentration-response curves were fitted using a 4 parameter logistic fit using the equation: $Y=A+(B-A)/(1+10^{Log\ IC50-X*D})$; where: Y=response, A=minimum response (positive control), B=maximum response (negative control), D=slope factor, x=log(Molar compound concentration). pIC$_{50}$ values are the negative logarithm of the IC$_{50}$ value.

Compounds of the Examples (apart from the compound of Example 27) were tested in the above assay, and had mean pIC$_{50}$ values of greater than 5.4. Compounds of Examples 1 to 26, 28 to 37, 39, 40, 45, 46 and 47 had mean pIC$_{50}$ values of 6.5 to 8.6. Compounds of Examples 1, 2, 4, 6, 10, 13, 15, 17, 19, 21, 22, 23, 24, 25, 28, 29, 30, 31, 32, 33, 34, 35, 36 and 37, had mean pIC$_{50}$ values of 7.5 to 8.6. Example 1 had a mean pIC$_{50}$ value of 7.8 and Example 15 had a mean pIC$_{50}$ value of 8.1

Compound Structures

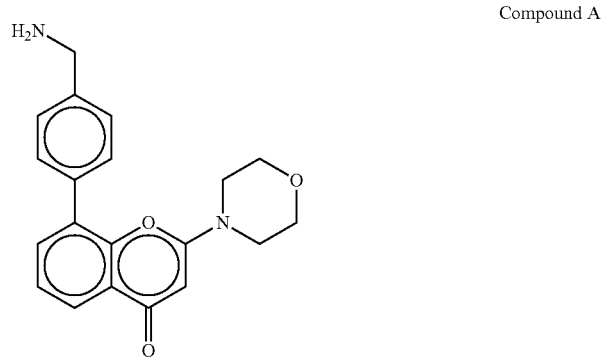

Compound A

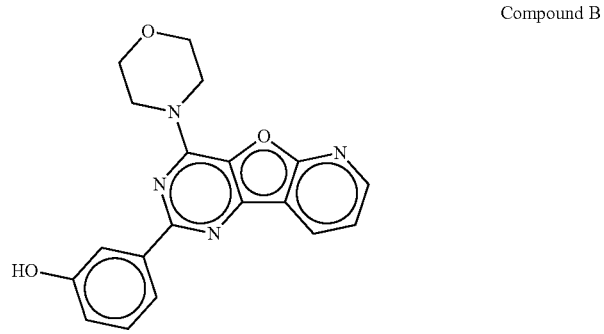

Compound B

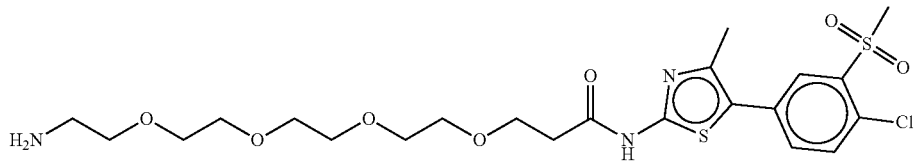

Compound C

Example 52

Highthroughput Phosphorylated Akt (Ser473) In Vitro Immunoassay

Immunoassay to measure effect of test compounds on phosphorylated Akt at serine 473 (pAKTs473) in primary human lung fibroblasts (Lonza Group Ltd, Basel, Switzerland, Catalogue No. CC-2512) using the MesoScale Discovery (MSD) platform to quantify levels of total Akt and pAKTser473.

Human lung fibroblasts were routinely maintained in fibroblast basal medium supplemented with 2% foetal bovine serum (FBS), 0.1% human fibroblast growth factor (FGF)-B, 0.1% insulin, 0.1% GA-100 (Lonza Group Ltd, Basel, Switzerland, Catalogue No. CC-3132) at 37° C. in 5% $CO_2$ according to the manufacturer's protocol.

For the assay, cells were harvested using Trypsin/EDTA, (Lonza Group Ltd, Basel, Switzerland, Catalogue No. CC-5012), at working concentration of 0.025%, resuspended to give $3 \times 10^5$ cells/ml and 50 ul/well seeded into 384-well plates (Greiner Group, Kremsmunster, Austria, Catalogue No. 781091) in media containing 0.4% FBS and incubated o/n at 37° C. in 5% $CO_2$.

Test compounds were dissolved in 100% DMSO to give 10 mM stock solutions and serially diluted to generate an 11-point concentration response curve. Compound were further diluted by 500-fold into 384-well V-bottom polypropylene plates (Greiner Group, Kremsmunster, Austria, Catalogue No. 781280) with media containing 0.4% FBS to give 50 µM top compound concentration in 0.5% DMSO.

Compounds were transferred to 384-well plates contacting cells (0.1% DMSO final) and incubated for 1 h at 37° C. in 5% CO2, prior to stimulation with platelet-derived growth factor (PDGF)-BB (R&D Systems, Catalogue No. 220-BB) at 10 ng/ml (final) for 10 min at RT. Cell assay plates were incubated on ice and treated with lysis buffer (Cell Signalling Technology, Catalogue No. 9806) containing protease and phosphatase inhibitors (Thermo Scientific, Catalogue No. 78444) followed by shaking for 30 min at 4° C.

MSD plates (MSD, MA6000 384-well GAR plate, Catalogue No. L21RA-2) were blocked with blocking buffer containing TBS (MSD, Cat. No. R61TX-1) with 0.5% bovine serum albumin (BSA) (Sigma Aldrich, Cat. No. A7906), 0.1% tween-20 (Sigma Aldrich, Catalogue No. P2287) and coated with rabbit-anti-human pAkt (s473) ab (Cell Signalling Technology, Catalogue No. CST #4060) at RT with shaking, followed by washing (×3) with 1×TBS wash reagent containing 0.1% Tween-20. Cell lysates (30 ul) were added and MSD plates centrifuged at 1000 rpm at 4° C. o/n.

Plates were washed with 1×TBS wash buffer (×3), prior to addition of mouse-anti-human-total Akt ab (1 mg/ml) (Upstate (Milipore), Catalogue No. 05-591) in blocking buffer and shaken at RT for 1 h. After washing with 1×TBS wash buffer (×3), plates were incubated with goat-anti-mouse SULFO-TAG detection ab (MSD, Catalogue No. R32AC-1) (1:500 in blocking buffer) for 1 h at RT. Plates were washed with 1×TBS (×3) and read buffer (2×) (MSD, Catalogue No. R92TC-1) added before detecting electrochemiluminescence (MSD Sector Imager 6000).

Data analysis was performed by determining % inhibition values for test compounds relative to the minimum (+PDGF-BB stimulation) and maximum responses (no PDGF-BB stimulation) with non-linear regression analysis to determine $IC_{50}$ values for test compounds.

Compounds of the Examples (apart from the Compound of Example 39) were tested in the above assay, and had a mean $pIC_{50}$ value of greater that 6. Compounds of Examples 1 to 37, 40, 47, 48 and 49 had mean $pIC_{50}$ values of 6.5 to 8.5. Compounds of Examples 1, 10, 15, 17, 19, 23, 31, 33, 34 and 35 had mean $pIC_{50}$ values of 8 to 8.6. Example 1 had a mean $pIC_{50}$ value of 8.2 and Example 15 had a mean $pIC_{50}$ value of 8.3

Example 53 Highthroughput Type I Collagen Deposition (Scar-in-a-Jar) High Content Screening Assay Highthroughput, cellular type I collagen deposition was measured by adapting a published method; scar-in-a-jar (Chen et al., 2009) to primary lung fibroblasts derived from human tissue and combining with high content analysis to permit fluorescent quantification of collagen deposited in the extracellular matrix (ECM). The human biological samples were sourced ethically and their research use was in accord with the terms of the informed consents Test compounds were dissolved in 100% DMSO to give 10 mM (stocks) and further diluted to give half log dilutions to generate an 11 point concentration response curve. 1 ul was transferred to 384-well plates (Greiner Group, Kremsmunster, Austria, Catalogue No Greine 781280r).

Human pulmonary fibroblasts were maintained in DMEM media (Gibco, Catalogue No 21969) supplemented with 4 mM L-glutamine (Gibco Catalogue No 25030-024) and 10% heat inactivated FBS (Gibco, Catalogue No 10099-141) at 37° C. in 10% CO2. Cells were harvested and resuspended at $4 \times 10^6$ cells/ml in a T175 cell culture flask (BD Falcom, Catalogue No: 353112) containing 50 mL of culture media. After 4 days 37° C. in 10% $CO_2$, cells were harvested and seeded at 4000 cells per well (50 µL/well) into 384-well plates (BD Falcon, Catalogue No 353962Greiner) in assay media (0.4% heat inactivated FBS, 4 mM L-glutamine). Plates were sealed with breathable seals (Sigma, Catalogue No. BEM-1). Assay plates were incubated for 72 h at 37° C. in 10% $CO_2$.

Assay media was supplemented with 112.5 mg/ml Ficoll 70 (Sigma, Catalogue No F2878), 75 mg/ml Ficoll 400 (Sigma, Catalogue No F4375) and 50 µg/ml ascorbic acid (Sigma, Catalogue No A8960). 30 µL assay media were added to 1 µl compound (37 µM compound concentration in 1% DMSO). Diluted compounds (10 µL) were transferred to plates containing cells and incubated for 3 h at 37° C. in 10%

CO2. Transforming growth factor (TGF)-β (R&D systems, Catalogue No 100-B/CF) was reconstituted to give 10 μg/mL (stock) and further diluted in assay media containing Ficoll and ascorbic acid (1 in 3333). TGF-β was added to cell plates (1 ng/ml final) and cells incubated for 72 h at 37° C. in 10% $CO_2$.

Media was aspirated from cells and 30 μL/well 100% ice-cold methanol added and incubated at RT for 5 min to fix cells. Methanol was aspirated and cells washed with PBS (3×). To block and permeabilise, cells were incubated with PBS containing 1% BSA and 0.1% Triton X 100 for 20 min, followed by PBS wash (3×). Cells were incubated with mouse anti human type I collagen monoclonal antibody (Sigma, Catalogue No C2456) diluted 1:1000 in PBS for 24 h at 4° C. Cells were washed with PBS containing 0.1% Tween-20 (3×) and incubated with secondary alexa fluor 488 goat-anti-mouse antibody (Invitrogen, Catalogue No A11001, 1 in 500 in PBS) and Hoechst 33342 (Sigma, Catalogue No H21492), 1 in 1000 in PBS) for 1 h at RT, prior to washing with PBS containing 0.1% Tween (×4).

Type I collagen immunoreactivity was detected using the INCell 2000 Analyzer (GE Healthcare, INcell 2000) set to excitation and emission wavelengths for DAPI and FITC with laser focus and exposure adjusted to appropriate levels. Images were imported and analysed using Columbus software (Perkin Elmer) and computational algorithms to quantify "total collagen area" and "cell count".

Data analysis was performed by determining % inhibition values for test compounds relative to the minimum (media only) and maximum responses (TGF-βstimulation) with non-linear regression analysis to determine $IC_{50}$ values for test compounds.

Compounds of the Examples (apart from compounds of Examples 14, 16, 27, 37, 44 and 46) were tested in the above assay, and had mean $pIC_{50}$ values of greater than 4.9. Compounds of Examples 1 to 13, 15, 17, 19 to 21, 23, 25, 28, 30 to 35, 40, 48 and 49 had mean $pIC_{50}$ values of 6 to 7.4. Compounds of Examples 1, 9, 11, 15, 23 and 31 had mean $pIC_{50}$ values of 7 to 7.4. The compound of Example 1 had a mean $pIC_{50}$ value of 7. The compound of Example 15 had a mean $pIC_{50}$ value of 7.

The invention claimed is:

1. A compound or pharmaceutically acceptable salt thereof, according to formula (I),

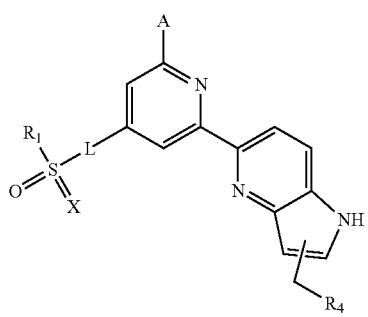

(I)

wherein:
A is

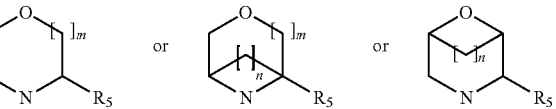

where ring A is attached via N;
X is O or NH;
L is $(C_1-C_3)$alkylene, $(C_1-C_3)$haloalkylene, $(C_3-C_5)$cycloalkylene or $(C_2-C_5)$ heterocycloalkylene;
$R_1$ is $(C_1-C_3)$alkyl, $(C_3-C_5)$ cycloalkyl, $(C_1-C_3)$alkoxy, or $NR_2R_3$,
which $(C_1-C_3)$alkyl, $(C_3-C_5)$cycloalkyl or $(C_1-C_3)$alkoxy is optionally substituted with $NR_2R_3$;
$R_2$ and $R_3$ are each independently $CH_3$ or H;
$R_4$ is $NH(C_1-C_3)$alkyl, $N((C_1-C_3)$alkyl$)_2$, $(C_1-C_3)$alkyl, $NH_2$ or OH;
$R_5$ is $(C_1-C_3)$alkyl or H;
m is 1 or 2; and
n is 1, 2 or 3;
or a pharmaceutically acceptable salt thereof.

2. A compound or pharmaceutically acceptable salt thereof, according to formula (Ia),

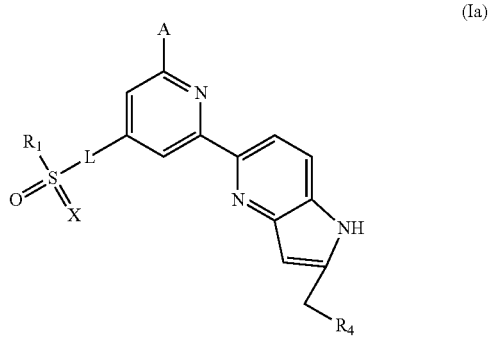

(Ia)

wherein:
A is

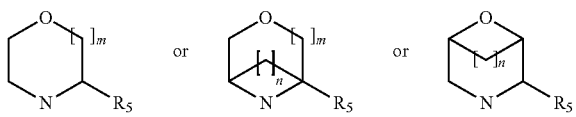

where ring A is attached via N;
X is O or NH;
L is $(C_1-C_3)$alkylene, $(C_1-C_3)$haloalkylene, $(C_3-C_5)$cycloalkylene or $(C_2-C_5)$ heterocycloalkylene;
$R_1$ is $(C_1-C_3)$alkyl, $(C_3-C_5)$ cycloalkyl, $(C_1-C_3)$alkoxy, or $NR_2R_3$,
which $(C_1-C_3)$alkyl, $(C_3-C_5)$cycloalkyl or $(C_1-C_3)$alkoxy is optionally substituted with $NR_2R_3$;
$R_2$ and $R_3$ are each independently $CH_3$ or H;
$R_4$ is $NH(C_1-C_3)$alkyl, $N((C_1-C_3)$alkyl$)_2$, $(C_1-C_3)$alkyl, $NH_2$ or OH;
$R_5$ $(C_1-C_3)$alkyl or H;
m is 1 or 2; and
n is 1, 2 or 3;
or a pharmaceutically acceptable salt thereof.

3. The compound or pharmaceutically acceptable salt according to claim 1 wherein A is

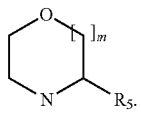

4. The compound or pharmaceutically acceptable salt according to claim 1 wherein X is O.

5. The compound or pharmaceutically acceptable salt according to claim 1, wherein L is methandiyl, propan-2,2-diyl, cyclopropan-1,1-diyl, difluoromethandiyl, tetrahydro-2H-pyran-4,4-diyl or piperidin-4,4-diyl.

6. The compound or pharmaceutically acceptable salt according to claim 5 wherein L is tetrahydro-2H-pyran-4,4-diyl.

7. The compound or pharmaceutically acceptable salt according to claim 1, wherein $R_1$ is $(C_1-C_3)$alkyl, cyclopropyl or $NR_2R_3$.

8. The compound or pharmaceutically acceptable salt according to claim 7, wherein $R_1$ is methyl, ethyl, cyclopropyl or $N(CH_3)_2$.

9. The compound or pharmaceutically acceptable salt according to claim 1, wherein $R_4$ is $NHCH_3$.

10. The compound or pharmaceutically acceptable salt according to claim 1, wherein $R_5$ is ethyl.

11. The compound or pharmaceutically acceptable salt according to claim 1 wherein m is 1.

12. A compound which is (S)-1-(5-(6-(3-ethylmorpholino)-4-(4-(methylsulfonyl)tetrahydro-2H-pyran-4-yl)pyridin-2-yl)-1H-pyrrolo[3,2-b]pyridin-2-yl)-N-methylmethanamine,

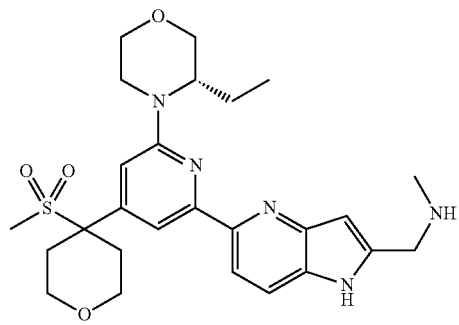

or a pharmaceutically acceptable salt thereof.

13. A compound which is (S)-1-(5-(6-(3-ethylmorpholino)-4-(4-(methylsulfonyl)tetrahydro-2H-pyran-4-yl)pyridin-2-yl)-1H-pyrrolo[3,2-b]pyridin-2-yl)-N-methylmethanamine,

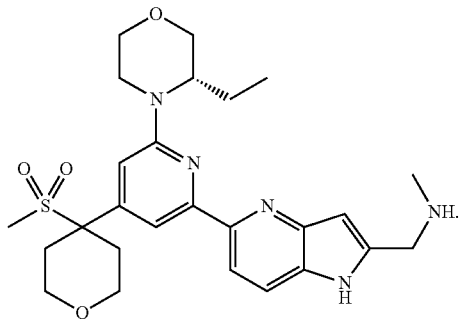

14. A pharmaceutical composition comprising a) a compound or pharmaceutically acceptable salt thereof as defined in claim 1, and b) a pharmaceutically acceptable excipient.

15. The pharmaceutical composition according to claim 14 wherein said compound is (S)-1-(5-(6-(3-ethylmorpholino)-4-(4-(methylsulfonyl)tetrahydro-2H-pyran-4-yl)pyridin-2-yl)-1H-pyrrolo[3,2-b]pyridin-2-yl)-N-methylmethanamine

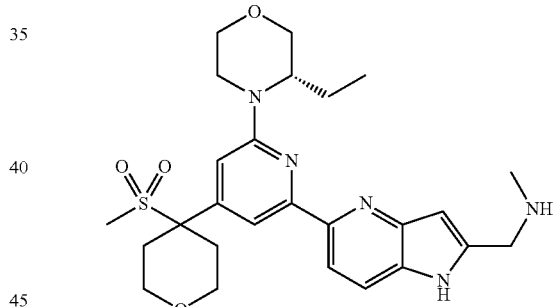

or a pharmaceutically acceptable salt thereof.

* * * * *